(12) United States Patent
Zhang et al.

(10) Patent No.: US 12,024,715 B2
(45) Date of Patent: Jul. 2, 2024

(54) COMPOSITIONS AND METHODS FOR IMPROVED T CELLS

(71) Applicant: Temple University-Of The Commonwealth System of Higher Education, Philadelphia, PA (US)

(72) Inventors: Yi Zhang, Wallingford, PA (US); Shan He, Blue Bell, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 435 days.

(21) Appl. No.: 16/761,599

(22) PCT Filed: Nov. 7, 2018

(86) PCT No.: PCT/US2018/059531
§ 371 (c)(1),
(2) Date: May 5, 2020

(87) PCT Pub. No.: WO2019/094404
PCT Pub. Date: May 16, 2019

(65) Prior Publication Data
US 2020/0270573 A1 Aug. 27, 2020

Related U.S. Application Data

(60) Provisional application No. 62/582,439, filed on Nov. 7, 2017.

(51) Int. Cl.
| | | |
|---|---|---|
| *A61P 35/00* | (2006.01) | |
| *A61K 35/17* | (2015.01) | |
| *C07K 16/28* | (2006.01) | |
| *C12N 5/0783* | (2010.01) | |
| *C12N 9/10* | (2006.01) | |
| *C12N 15/85* | (2006.01) | |

(52) U.S. Cl.
CPC ............ *C12N 5/0636* (2013.01); *A61K 35/17* (2013.01); *A61P 35/00* (2018.01); *C07K 16/2803* (2013.01); *C12N 9/1007* (2013.01); *C12N 15/85* (2013.01); *C12Y 201/01043* (2013.01); *C07K 2317/24* (2013.01); *C07K 2319/02* (2013.01); *C07K 2319/03* (2013.01); *C07K 2319/33* (2013.01); *C12N 2510/00* (2013.01)

(58) Field of Classification Search
CPC .... C12N 5/0636; C12N 9/1007; C12N 15/85; C12N 2510/00; A61K 35/17; A61P 35/00; C07K 16/2803; C07K 2317/24; C07K 2319/02; C07K 2319/03; C07K 2319/33
USPC ..................................................... 424/93.21
See application file for complete search history.

(56) References Cited

U.S. PATENT DOCUMENTS

| | | | |
|---|---|---|---|
| 9,057,054 B2 * | 6/2015 | Zhang | ................ A61K 38/2013 |
| 2005/0222163 A1 | 10/2005 | Eck | |
| 2009/0012031 A1 | 1/2009 | Chinnaiyan | |
| 2010/0021420 A1 | 1/2010 | Lyons | |
| 2012/0071418 A1 | 3/2012 | Copeland | |
| 2014/0271635 A1 | 9/2014 | Brogdon | |
| 2014/0378470 A1 | 12/2014 | Creasy | |
| 2015/0183799 A1 | 7/2015 | Nakamura | |
| 2017/0267739 A1 * | 9/2017 | Berger | ................ C07K 14/7051 |

FOREIGN PATENT DOCUMENTS

| | | | |
|---|---|---|---|
| WO | 2013067302 A1 | 5/2013 | |
| WO | 2014077784 A1 | 5/2014 | |
| WO | WO 2014197826 | * 12/2014 | ........... C12N 15/113 |

OTHER PUBLICATIONS

Zhang et al. (FEBS Lett. Dec. 21, 2015, vol. 589, No. 24, pp. 4106-4111).*
Onea, et al., "CD19 chimeric antigen receptor (CD19 CAR)-redirected adoptive T-cell immunotherapy for the treatment of relapsed or refractory B-cell Non-Hodgkin's Lymphomas", American Journal of Cancer Research, vol. 6, No. 2 (2016), pp. 403-424.
Overwijk, et al., "Tumor regression and autoimmunity after reversal of a functionally tolerant state of self-reactive CD8+ T cells", Journal of Experimental Medicine, vol. 198, No. (2003), pp. 569-580.
Paley et al., "Progenitor and Terminal Subsets of CD8+ T Cells Cooperate to Contain Chronic Viral Infection", Science, vol. 338, No. 6111 (2012), pp. 1220-1225.
Pear, et al., "Efficient and rapid induction of a chronic myelogenous leukemia-like myeloproliferative disease in mice receiving P210 bcr/abl-transduced bone marrow", Blood, vol. 92, No. 10 (1998), pp. 3780-3792.
Pearce, et al., "Control of effector CD8+ T cell function by the transcription factor Eomesodermin", Science, vol. 302, No. 5647 (2003), pp. 1041-1043.
Porter, et al., "Chimeric antigen receptor-modified T cells in chronic lymphoid leukemia", New England Journal of Medicine, vol. 465, No. 8 (2011), pp. 725-733.
Restifo et al., "Adoptive immunotherapy for cancer: harnessing the T cell response," Nat Rev Immunol, 2012, 12:269-281.
Ringrose, L. & Paro, R. "Polycomb/Trithorax response elements and epigenetic memory of cell identity", Development 134, 223-232 (2007).
Rosenberg, et al., "Adoptive cell transfer as personalized immunotherapy for human cancer", Science, vol. 348, No. 6230 (2015), pp. 62-68.
Russ, et al., "Distinct epigenetic signatures delineate transcriptional programs during virus-specific CD8(+) T cell differentiation", Immunity, vol. 41, No. 5 (2014), pp. 853-865.
Sadelain, "T-cell engineering for cancer immunotherapy", Cancer Journal, vol. 15, No. 6(2009), pp. 451-455.
Savoldo, et al., "CD28 costimulation improves epansion and persistence of chimeric antigen receptor-modified T cells in lymphoma patients", Journal of Clinical Investigations, vol. 121, No. 5 (2011), pp. 1822-1826.

(Continued)

*Primary Examiner* — Yan Xiao
(74) *Attorney, Agent, or Firm* — Riverside Law LLP

(57) ABSTRACT

The invention provides compositions and methods for generating improved T cells having increased Ezh2 activity and methods of use thereof in the treatment of cancer and chronic infection.

9 Claims, 28 Drawing Sheets

(56) References Cited

OTHER PUBLICATIONS

Scholler, et al., "Decade-long safety and function of retroviral-modified chimeric antigen receptor T cells", Science Translational Medicine, vol. 4, No. 132 (2012), 132ra153.

Shchegolevataya O.O. et al., "Development of acute myeloid leukemia from donor cells after allogeneic peripheral blood stem cell transplantation in a female patient with acute monoblastic leukemia", Ter Arkh. 2011;83(3):57-62.

Su, I. H. et al., "Ezh2 controls B cell development through histone H3 methylation and Igh rearrangement", Nat Immunol 4, 124-131 (2003).

Tong, et al., "Ezh2 Regulates Transcriptional and Posttranslational Expression of T-bet and Promotes Th1 Cell Responses Mediating Aplastic Anemia in Mice", Journal of Immunology, vol. 192, No. 11 (2014), pp. 5012-5022.

Turtle, et al., "CD19 Car-T cells of defined CD4+: CD8+ composition in adult B cell ALL patients", Journal of Clinical Investigations, vol. 126, No. 6 (2016), pp. 2123-2338.

Turtle, et al., "Immunotherapy of non-Hodgkin's lymphoma with a defined ratio of CD8+ and CD4+ CD19-specific chimeric antigen receptor-modified T cells", Science Translational Medicine, vol. 8, No. 355 (2016), 355ra116.

Van Der Waart, et al., "Inhibition of Akt signaling promotes the generation of superior tumor-reactive T cells for adoptive immunotherapy", Blood, vol. 124, No. 23 (2014), pp. 3490-3500.

Verykokakis, et al., "SAP protein-dependent natural killer T-like cells regulat the development of CD8(+) T cells with innate lymphocyte characteristics", Immunity, vol. 33, No. 2 (2010), pp. 203-215.

Vonderheide, et al., "Engineering T cells for cancer: our synthetic future", Immunological Reviews, vol. 257 (2013), pp. 7-13.

Wang, et al., "Phase 1 studies of central memory-derived CD19 Car T-cell therapy following autologous HSCT in patients with B-cell NHL", Blood, vol. 127, No. 24 (2016), pp. 2980-2990.

Wei, et al., "Global mapping of H3K3me3 and K3K27me3 reveals specificity and plasticity in lineage fate determination of differentiating CD4+ T cells", Immunity, vol. 30, No. 1 (2009), pp. 155-167.

Wherry, E. J. & Ahmed, R. "Memory CD8 T-cell differentiation during viral infection", J Virol 78, 5535-5545 (2004).

Wherry, et al., "Molecular Signature of CD8+ T Cell exhaustion during Chronic Viral Infection", Immunity, vol. 27 (2007), pp. 670-684.

Wu, et al., "Understanding the words of chromatin regulation", Cell, vol. 136, No. 2 (2009), pp. 200-206.

Xu, et al., "EZH2 Oncogenic Activity in Castration-Resistant Prostate Cancer Cells is Polycomb-Independent", Science, vol. 338, No. 6113 (2012), pp. 1465-1469.

Yan, J. et al., "EZH2 phosphorylation by JAK3 mediates a switch to noncanonical function in natural killer/T-cell lymphoma", Blood 128, 948-958 (2016).

Yang, et al., "The transcriptional regulators Id2 and Id3 control the formation of distinct memory CD8+ T cell subsets", Nature Immunology, vol. 12 (2011), pp. 1221-1229.

Youngblood, B., Hale, J. S. & Ahmed, R. "Memory CD8 T cell transcriptional plasticity", F1000Prime Rep 7, 38, (2015).

Zhang et al., "EZH2 phosphorylation regulates Tat-induced HIV-1 transactivation via ROS/Akt signaling pathway", FEBS Letters, (Dec. 21, 2015), vol. 589, No. 24, pp. 4106-4111.

Zhang et al., "Host-reactive CD8+ memory stem cells in graft-versus-host disease," Nat Med, 2005, 11:1299-1305.

Zhang et al., "Notch signaling is a critical regulator of allogeneic CD4+ T-cell responses mediating graft-versus-host disease," Blood, 2011, 117:299-308.

Zhang, et al., "APCs in the Liver and Spleen Recruit Activated Allogeneic CD8+ T Cells to Elicit Hepatic Graft- Versus-Host Disease", Journal of Immunology, vol. 169, No. 12 (2002), pp. 7111-7118.

Zhang, et al., "Preterminal host dendritic cells in irradiated mice prime CD8+ T cell-mediated acute graft-versus-host disease", Journal of Clinical Investigations, vol. 109, No. 10 (2002), pp. 1335-1344.

Zhang, N. & Bevan, M. J. "CD8(+) T cells: foot soldiers of the immune system", Immunity 35, 161-168, (2011).

Zhang, Y., Joe, G., Hexner, E., Zhu, J. & Emerson, S.G. "Alloreactive memory T cells are responsible for the persistence of graft ---versus ---host disease", J Immunol 174, 3051---3058 (2005).

Zhao, E., Maj, T., Kryczek, I. et al. "Cancer mediates effector T cell dysfunction by targeting microRNAs and EZH2 via glycolysis restriction", Nat Immunol 17, 95-103 (2016).

Ahmed, et al., "The precursors of memory: models and controversies", Nature Reviews Immunology, vol. 9 (2009), pp. 662-668.

Ali, et al., "T cells expressing an anti-B-cell maturation antigen chimeric antigen receptor cause remissions of multiple myeloma", Blood, vol. 128, No. 13 (2016), pp. 1688-1700.

Araki, et al., "Genome-wide Analysis of Histone Methylation Reveals Chromatin State-Based Regulation of Gene Transcription and Function of Memory CD8+ T Cells", Immunity, vol. 302, No. 6 (2009), pp. 912-925.

Bantignies, et al., "Cellular memory and dynamic regulation of polycomb group proteins", Current Opinion in Cell Biology, vol. 18, No. 3 (2006), pp. 275-283.

Barrett, et al., "Chimeric antigen receptor therapy for cancer", Annual Review of Medicine, vol. 65 (2014), pp. 333-347.

Boyer, et al., "Polycomb complexes repress developmental regulators in murine embryonic stem cells", Nature, vol. 441, No. 7091 (2006), pp. 349-353.

Bracken, A.P. et al., "The Polycomb group proteins bind throughout the INK4A-ARF locus and are disassociated in senescent cells", Genes Dev 21, 525-530 (2007).

Brudno, et al., "Allogeneic T Cells That Express an Anti-CD19 Chimeric Antigen Receptor Induce Remissions of B-Cell Malignancies That Progress After Allogeneic Hematopoietic Stem-Cell Transplantation Without Causing Graft-Versus-Host Disease", Journal of Clinical Oncology, vol. 34 (2016), pp. 112-1121.

Buchholz, et al., "Disparate Individual Fates Compose Robust CD8+ T Cell Immunity", Science, vol. 340, No. 6132 (2013), pp. 630-635.

Cha, et al., "Akt-Mediated Phosphorylation of EZH2 Suppresses Methylation of Lysine 27 in Histone H3", Science, vol. 310, No. 5746 (2005), pp. 306-310.

Chang et al., "Molecular regulation of effector and memory T cell differentiation", Nature Immunology, vol. 15 (2014), pp. 1104-1115.

Chang, et al., "Asymmetric T lymphocyte division in the initiation of adaptive immune responses", Science, vol. 315, No. 5819 (2007), pp. 1687-1691.

Cho et al., "Cyclosporine A inhibits IL-15-induced IL-17 production in CD 4+ T cells via down- regulation of PI3K/Akt and NF-KB", Immunology Letters, (Jan. 15, 2007), vol. 108, No. 1, pp. 88-96.

Coomes, S. M., Wilke, C. A., Moore, T. A. & Moore, B. B. "Induction of TGF-beta 1, not regulatory T cells, impairs antiviral immunity in the lung following bone marrow transplant", J Immunol 184, 5130-5140, (2010).

Crompton, et al., "Akt Inhibition Enhances Expansion of Potent Tumor-Specific Lymphocytes with Memory Cell Characteristics", Cancer Research, vol. 75, No. 2 (2015), pp. 296-305.

Crompton, et al., "Uncoupling T-cell expansion from effector differentiation in cell-based immunotherapy", Immunological Reviews, vol. 257, No. 1 (2013), pp. 264-276.

Cui, Y. et al., "Harnessing the physiology of lymphopenia to support adoptive immunotherapy in lymphoreplete hosts", Blood 114, 3831-3840 (2009).

Davila, et al., "Efficacy and toxicity management of 19-28z Car T cell therapy in B cell acute lymphoblastic leukemia", Science Translational Medicine, vol. 6, No. 224 (2014), 224ra25.

Fearon, "The Expansion and Maintenance of Antigen-Selected CD8+ T Cell Clones", Advances in Immunology, vol. 96 (2007), pp. 103-139.

Gattinoni, et al., "A human memory T cell subset with stem cell-like properties", Nature Medicine, vol. 17 (2011), pp. 1290-1297.

Gattinoni, et al., "Wnt signaling arrests effector T cell differentiation and generates CD8+ memory stem cells", Nature Medicine, vol. 15, No. 7 (2009), pp. 808-813.

(56) References Cited

OTHER PUBLICATIONS

Gattinoni, L., Klebanoff, C.A. & Restifo, N.P. "Paths to stemness: building the ultimate antitumour T cell", Nature reviews. Cancer 12, 671-684 (2012).
Gerlach, et al., "Heterogeneous Differentiation Patterns of Individual CD8+ T Cells", Science, vol. 340, No. 6132 (2013), pp. 635-639.
Grupp, et al., "Chimeric Antigen Receptor-Modified T Cells for Acute Lymphoid Leukemia", New England Journal of Medicine, vol. 368 (2013), pp. 1509-1518.
He et al., "Inhibition of histone methylation arrests ongoing graft-versus-host disease in mice by selectively inducing apoptosis of alloreactive effector T cells," Blood, 2012, 119:1274-1282.
He, et al., "The histone methyltransferase Ezh2 is a crucial epigenetic regulator of allogeneic T-cell responses mediating graft-versus-host disease", Blood, vol. 122, No. 25 (2013), pp. 4119-4128.
He, S. et al., "Inhibition of histone methylation arrests ongoing graft-versus-host disease in mice by selectively inducing apoptosis of alloreactive effector T cells", Blood 119, 1274-1282 (2012).
Hinrichs, et al., "Molecular Pathways: Breaking the Epithelial Cancer Barrier for Chimeric Antigen Receptor and T-cell Receptor Gene Therapy", Clinical Cancer Research, vol. 22, No. 7 (2016), pp. 1559-1564.
Huang et al., "Hsp90 inhibition destabilizes Ezh2 protein in alloreactive T cells and reduces graft-versus-host disease in mice," Blood, May 18, 2017;129(20):2737-2748.
Inoki, et al., "TSC2 Integrates Wnt and Energy Signals via a Coordinated Phosphorylation by AMPK and GSK3 to Regulate Cell Growth", Cell, vol. 126, No. 5 (2006), pp. 955-968.
Jensen et al., "Design and implementation of adoptive therapy with chimeric antigen receptor-modified T cells", Immunological Reviews, vol. 257, No. 1 (2013), pp. 127-144.
Jensen, et al., "Designing chimeric antigen receptors to effectively and safely targe tumors", Current Opinion in Immunology, vol. 33 (2015), pp. 9-15.
Ji, et al., "Repression of the DNA-binding inhibitor ID3 by Blimp-1 limits CD8+ T cell memory", Nature Immunology, vol. 12 (2011), pp. 1230-1237.
Joshi, N.S. et al., "Inflammation directs memory precursor and short-lived effector CD8(+) T cell fates via the graded expression of T-bet transcription factor", Immunity 27, 281-295 (2007).
Kaech, et al., "Effector and memory T-cell differentiation: implications for vaccine development", Nature Reviews Immunology, vol. 2 (2002), pp. 251-262.
Kaech, et al., "Transcriptional control of effector and memory CD8+ T cell differentiation", Nature Reviews Immunology, vol. 12 (2012), pp. 749-761.
Kakaradov, et al., "Early transcriptional and epigenetic regulation of CD8+ T cell differentiation revealed by single-cell RNA sequencing", Nature Immunology, vol. 18 (2017), pp. 422-432.
Karantanos T, Chistofides A, Barhdan K, Li L, Boussiotis VA. "Regulation of T Cell Differentiation and Function by EZH2", Front Immunol. May 3, 2016;7:172.
Kim E, Kim M, Woo DH, Shin Y, Shin J, Chang N, Oh YT, Kim H, Rheey J, Nakano I, Lee C, Joo KM, Rich JN, Nam DH, Lee J. "Phosphorylation of EZH2 activates STAT3 signaling via STAT3 methylation and promotes tumorigenicity of glioblastoma stem-like cells", Cancer Cell. Jun. 10, 2013;23(6):839-52.
Kim, E. et al., "Phosphorylation of EZH2 activates STAT3 signaling via STAT3 methylation and promotes tumorigenicity of glioblastoma stem-like cells", Cancer Cell 23, 839-852 (2013).
Kim, et al., "Role of PI3K/Akt signaling in memory CD8 T cell differentiation", Frontiers in Immunology, vol. 4 (2013), Article 20.
Klebanoff, et al., "Memory T cell-driven differentiation of naive cells impairs adoptive immunotherapy", Journal of Clinical Investigations, vol. 126, No. 1 (2016), pp. 318-334.
Kochenderfer, et al., "Adoptive transfer of syngeneic T cells transduced with a chimeric antigen receptor that recognizes murine CD19 can eradicate lymphoma and normal B cells", Blood, vol. 116, No. 19 (2010), pp. 3875-3886.
Kochenderfer, et al., "Chemotherapy-refractory diffuse large B-cell lymphoma and indolent B-cell malignancies can be effectively treated with autologous T cells expressing an anti-CD19 chimeric antigen receptor", Journal of Clinical Oncology, vol. 33, No. 6 (2015), pp. 540-549.
Kouzarides, "Chromatin Modifications and Their Function", Cell, vol. 128, No. 4 (2007), pp. 693-705.
Lee, S.T. et al., "Context-specific regulation of NF-kappaB target gene expression by EZH2 in breast cancers", Mol Cell 43, 798-810 (2011).
Leen, A. M., Heslop, H. E. & Brenner, M. K. "Antiviral T-cell therapy", Immunol Rev 258, 12-29, (2014).
Margueron et al., "The Polycomb complex PRC2 and its mark in life", Nature, vol. 469 (2011), pp. 343-349.
Masson, et al., "Id2-Mediated Inhibition of E2A Represses Memory CD8+ T Cell Differentiation ", Journal of Immunology, vol. 190 (2013), pp. 4585-4594.
Maude, et al., "Chimeric Antigen Receptor T Cells for Sustained Remissions in Leukemia", New England Journal of Medicine, vol. 371 (2014), pp. 1507-1517.

\* cited by examiner

COMPOSITIONS AND METHODS FOR IMPROVED T CELLS

CROSS-REFERENCE TO RELATED APPLICATIONS

This application is the U.S. national phase application filed under 35 U.S.C. § 371 claiming benefit to International Patent Application No. PCT/US18/059531, filed on Nov. 7, 2018, which is entitled to priority under 35 U.S.C. § 119(e) to U.S. provisional application No. 62/582,439, filed Nov. 7, 2017, the disclosures of which are incorporated herein by reference in their entirety.

STATEMENT REGARDING FEDERALLY SPONSORED RESEARCH OR DEVELOPMENT

This invention was made with government support under 1R01HL127351-01A1 awarded by the National Institutes of Health (NIH). The government has certain rights in the invention.

BACKGROUND OF THE INVENTION

Multipotent T memory stem cells ($T_{SCM}$) are a rare lymphocyte population that can self-renew and give rise to all subsets of effector and memory T cells (Chang et al., 2014, Nat Immunol, 15:1104-1115; Fearon, 2007, Adv Immunol, 96:103-139; Kaech and Cui, 2012, Nat Rev Immunol, 12:749-761; Rosenberg and Restifo, 2015, Science, 348:62-68). Regulation of the balance of $T_{SCM}$ between self-renewal and differentiation is central to maintaining effector cells and sustained tumor regression. However, chronic antigen stimulation within tumors drives T cells toward terminal differentiation, impairing their capacity to eradicate tumors (Paley et al., 2012, Science, 338:1220-1225; Restifo et al., 2012, Nat Rev Immunol, 12:269-281; Jensen and Riddell, 2014, Immunol Rev, 257:127-144; Sadelain, 2009, Cancer J, 15:451-455). One important clinical scenario requiring optimal memory potential is adoptive cell therapy (ACT), where complete destruction of malignant cells requires maintenance of effector cells ($T_{EFF}$) over weeks or months (Jensen and Riddell, 2014, Immunol Rev, 257:127-144; Sadelain, 2009, Cancer J, 15:451-455; Crompton et al., 2014, Immunol Rev, 257:264-276; Vonderheide and June, 2014, Immunol Rev, 257:7-13). It has been reported that Akt activation drives CD8+ T cells towards terminal differentiation and diminishes the memory potential (Kim and Suresh, 2014, Front Immunol, 4:20). Major transcription factors including Id3, Id2, T-bet and Prdm1 control the differentiation and function of effector and memory cells (Chang et al., 2014, Nat Immunol, 15:1104-1115; Kaech and Cui, 2012, Nat Rev Immunol, 12:749-761). How antigen-driven CD8+ T cells epigenetically integrate the intermediate Akt signaling and these major transcription factors (TFs) to regulate the balanced generation of effector and memory cells for controlling tumor growth remains poorly defined.

Histone methylation regulates gene transcription patterns involved in multiple cellular processes (Wu et al., 2009, Cell, 136:200-206; Kouzarides, 2007, Cell, 128:693-705; Margueron and Reinberg, 2011, Nature, 469:343-349). For example, in T cells, trimethylation of histone 3 at lysine 4 (H3K4me3) is typically enriched in gene promoters associated with active transcription. H3K27me3 is deposited within gene loci typically correlated with transcriptional repression that is primarily associated with T cell proliferation, differentiation and survival. Upon T cell activation, the majorities of these gene loci lose repressive H3K27me3 modifications, suggesting that removal of H3K27me3 represents an important mechanism for initiating gene transcription (Araki et al., 2009, Immunity, 30:912-925; Russ et al., 2014, Immunity, 41:853-865; Wei et al., 2009, Immunity, 30:155-167).

Transfer of T cells genetically modified to express a chimeric antigen receptor (CAR) specific for CD19 (CD19 CAR-T cells) cells has produced as high as 90% of complete response (CR) in refractory B-cell acute lymphoblastic leukemia (B-ALL) but only 20-50% of patients with advanced lymphoma experienced a CR (Sadelain, 2009, Kochenderfer et al., 2010, Blood, 116(19):3875-3886; Porter et al., 2011, Savoldo et al., 2011, J Clin Invest, 121: 1822-1826; N Engl J Med, 365(8):725-733; Grupp et al., 2013, N Engl J Med, 368:1509-1518; Cancer J. 15:451-455; Grupp et al., 2013, N Engl J Med, 368:1509-1518; Vonderheide et al., 2014, Immunol Rev. 257:7-13; Jensen et al., 2014, Immunol Rev, 257:127-144; Maude et al., 2014, N Engl J Med, 371:1507-1517; Barrett et al., 2014, Annu Rev Med, 65:333-347; Davila et al., 2014, Sci Transl Med, 6:224-225; Jensen et al., 2015, Curr Opin Immunol, 33:9-15; Turtle et al., 2015, Kochenderfer et al., 2015, J Clin Oncol, 33(6):540-549; J Clin Invest, 126:2123-2138; Onea et al., 2016, Am J Cancer Res, 6:403-424; Turtle et al., 2016, Sci Transl Med, 8:355ra116; Wang et al., 2016, Blood. 127: 2980-2990; Ali et al., 2016, Blood, 128:1688-1700; Brudno et al., 2016, J Clin Oncol, 34:1112-1121). Clinical studies have revealed that the number of CAR T cells in the blood of patients rose to a peak between seven and twenty days after infusion but rapidly decreased thereafter, suggesting an impaired capacity of CAR T cells to persist. Understanding the molecular regulators of CAR $T_{SCM}$ self-renewal and differentiation is essential for developing new strategies to improve the therapeutic efficacy of ACT.

Thus, there is a need in the art for compositions and methods for improved T cells. The present invention addresses this need.

SUMMARY OF THE INVENTION

In one embodiment, the invention relates to a composition comprising an improved T cell, wherein the T cell has increased Ezh2 activity.

In one embodiment, the T cell expresses an Ezh2S21A protein.

In one embodiment, the T cell has been contacted with an inhibitor of a regulator of at least one of the level and activity of Ezh2.

In one embodiment, the regulator of Ezh2 activity is selected from the group consisting of PI3K, calcinurin, JMJD3, AKT, AP-1, CDk1, CDK4/6, DNA-PK and a combination thereof.

In one embodiment, the inhibitor is selected from the group consisting of CsA, GSK-J4, MEK2206, TanIIA, and a combination thereof.

In one embodiment, the T cell is selected from the group consisting of a CART cell, a TCR-transgenic T cell, a Tumor infiltrating T cell (TIL), and an autologous T cell.

In one embodiment, the T cell is a CART cell comprising a chimeric antigen receptor (CAR) comprising at least one sequence selected from the group consisting of a binding domain, a co-stimulatory signaling domain, a cytoplasmic signaling sequence and a combination thereof.

In one embodiment, the CAR comprises a CD19 binding domain.

In one embodiment, the CAR comprises a 4-1BB co-stimulatory signaling domain.

In one embodiment, the CAR comprises a CD3ζ cytoplasmic signaling sequence.

In one embodiment, the invention relates to a composition comprising a combination of at least two inhibitors selected from the group consisting of a calcinurin inhibitor, an AKT inhibitor, a PI3K inhibitor, an AP-1 inhibitor, a CDk1 inhibitor, a CDK4/6 inhibitor and a DNA-PK inhibitor.

In one embodiment, the composition comprises a combination of at least three inhibitors selected from the group consisting of a calcinurin inhibitor, an AKT inhibitor, a PI3K inhibitor, an AP-1 inhibitor, a CDk1 inhibitor, a CDK4/6 inhibitor and a DNA-PK inhibitor.

In one embodiment, the composition comprises a combination of at least four inhibitors selected from the group consisting of a calcinurin inhibitor, an AKT inhibitor, a PI3K inhibitor, an AP-1 inhibitor, a CDk1 inhibitor, a CDK4/6 inhibitor and a DNA-PK inhibitor.

In one embodiment, the invention relates to a vector comprising a nucleic acid sequence encoding an Ezh2S21A protein.

In one embodiment, the vector is a lentivirus vector.

In one embodiment, the invention relates to a cell comprising a nucleic acid sequence encoding an Ezh2S21A protein.

In one embodiment, the cell is selected from the group consisting of a CART cell, a TCR-transgenic T cell, a TIL, and an autologous T cell.

In one embodiment, the invention relates to a method of generating an improved T cell having increased Ezh2 activity.

In one embodiment, the method comprises contacting a T cell with at least one inhibitor of a regulator of at least one of the level and activity of Ezh2.

In one embodiment, at least one inhibitor is selected from the group consisting of a calcinurin inhibitor, an AKT inhibitor, a PI3K inhibitor, an AP-1 inhibitor, a CDk1 inhibitor, a CDK4/6 inhibitor and a DNA-PK inhibitor.

In one embodiment, at least one inhibitor is selected from the group consisting of CsA, Tacrolimus, GSK-J4, 5-Carboxy-8-hydroxyquinoline, MEK2206, SB203580, MK2206, SC79, AZD5363, LM22B-10, GDC-0068, GSK-690693, Afuersertib, AKT inhibitor VIII, A-443654, TIC10, Honokiol, Triciribine, A-674563, Prifosine, Miltefosine, SR11302, SP100030, c-JUN peptide, TanIIA, E3330, NNGH, Sulfaphenoazole, U0126 monoethanolate, IQ-1S, SM-7368, NIN-43, MEK inhibitor VII, TNAP inhibitor, FR180204, APE1 inhibitor III, (S)-AR-TURMERONE, 4-O-METHYLHONOKIOL, 5-(9-ISOPROPYL-2-MORPHOLINO-9H-PURIN-6-YL)PYRIMIDIN-2-AMINE, A66, Arenobufagin, Bay80-6946, Benidipine Hydrochloride, BEX235, BK M120, BYL719, CAL-101, CH5132799, CUDC-907, GDC-0980, GSK-2126458, GSK-2334470, GSK-2636771, IPI-145, Ly-294002, PF-04691502 Dihydrate, Piceatanol, PKI-402, PP-121, PX-866, R547, Dinaciclib, BMS-265246, JNJ-7706621, AZD5438, Alvocidib, SU9516, PHA-793887, P276-00, AT7519, PHA-7677491, Milciclib (PHA-848125), SNS-032, NU6027, LDC000067, Palbociclib, Everolimus, Ly3023414, KU-57788, NU 7026, PIK-75, LTURM34, CC-115 and Compound 401 and a combination thereof and a combination thereof.

In one embodiment, the method comprises genetically modifying a T cell to express an Ezh2S21A protein.

In one embodiment, the invention relates to a method of treating or preventing a disease or disorder in a subject in need thereof, the method comprising administering to the mammal an effective amount of an improved T cell, wherein the T cell has increased Ezh2 activity.

In one embodiment, the T cell expresses an Ezh2S21A protein.

In one embodiment, the T cell has been contacted with an inhibitor of a regulator of at least one of the level and activity of Ezh2.

In one embodiment, the regulator of Ezh2 activity is selected from the group consisting of a calcinurin inhibitor, an AKT inhibitor, a PI3K inhibitor, an AP-1 inhibitor, a CDk1 inhibitor, a CDK4/6 inhibitor and a DNA-PK inhibitor.

In one embodiment, the inhibitor of a regulator of Ezh2 activity is selected from the group consisting of CsA, Tacrolimus, GSK-J4, 5-Carboxy-8-hydroxyquinoline, MEK2206, SB203580, MK2206, SC79, AZD5363, LM22B-10, GDC-0068, GSK-690693, Afuersertib, AKT inhibitor VIII, A-443654, TIC10, Honokiol, Triciribine, A-674563, Prifosine, Miltefosine, SR11302, SP100030, c-JUN peptide, Tanshinone IIA (TanIIA), E3330, NNGH, Sulfaphenoazole, U0126 monoethanolate, IQ-1S, SM-7368, NIN-43, MEK inhibitor VII, TNAP inhibitor, FR180204, APE1 inhibitor III, (S)-AR-TURMFRONE, 4-O-METHYL-HONOKIOL, 5-(9-ISOPROPYL-2-MORPHOLINO-9H-PURIN-6-YL)PYRIMIDIN-2-AMINE, A66, Arenobufagin, Bay80-6946, Benidipine Hydrochloride, BEX235, BKM120, BYL719, CAL-101, CH5132799, CUDC-907, GDC-0980, GSK-2126458, GSK-2334470, GSK-2636771, IPI-145, Ly-294002, PF-04691502 Dihydrate, Piceatanol, PKI-402, PP-121, PX-866, R547, Dinaciclib, BMS-265246, JNJ-7706621, AZD5438, Alvocidib, SU9516, PHA-793887, P276-00, AT7519, PHA-7677491, Milciclib (PHA-848125), SNS-032, NU6027, LDC000067, Palbociclib, Everolimus, Ly3023414, KU-57788, NU 7026, PIK-75, LTURM34, CC-115 and Compound 401 and a combination thereof.

In one embodiment, the T cell is selected from the group consisting of a CART cell, a TCR-transgenic T cell, a TIL, and an autologous T cell.

In one embodiment, the T cell is a CART cell comprising a chimeric antigen receptor (CAR) comprising at least one sequence selected from the group consisting of a binding domain, a co-stimulatory signaling domain, a cytoplasmic signaling sequence and a combination thereof.

In one embodiment, the CAR comprises a CD19 binding domain.

In one embodiment, the CAR comprises a 4-1BB co-stimulatory signaling domain.

In one embodiment, the CAR comprises a CD3ζ Cytoplasmic signaling sequence.

In one embodiment, the subject is a human.

In one embodiment, the the disease or disorder is cancer.

In one embodiment, the cancer is selected from the group consisting of primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, glioblastoma, neuroblastoma and any combination thereof.

In one embodiment, the disease or disorder is a chronic infection.

In one embodiment, the chronic infection is selected from the group consisting of HIV infection, hepatitis infection, CMV-infection and EBV infection.

BRIEF DESCRIPTION OF THE DRAWINGS

FIG. 1, comprising FIG. 1A depicts exemplary experimental results demonstrating WT and Ezh2$^{-/-}$ CD44$^{lo}$CD8$^+$ naïve (T$_N$) Pmel-1 cells (1×10$^6$, Thy1.1$^+$) were transferred into sublethally irradiated (5 Gy) B6 mice (Thy1.2$^+$) that had pre-established B16 melanoma, followed by immunization with IL-2 (1×10$^5$ IU/injection, i.p., twice a day) and gp100-pulsed DCs (gp100/DCs, 1×10$^6$) for 3 days. Tumor size was monitored over time. For FIG. 1B through FIG. 1F, WT and Ezh2$^{-/-}$ T$_N$ Pmel-1 cells (1×10$^6$, Thy1.1$^+$) were transferred into sublethally irradiated (5 Gy) non-tumor-bearing B6 mice (Thy1.2$^+$), followed by immunization with IL-2 (1×10$^5$ IU/injection, i.p., twice a day) and gp100-pulsed DCs (gp100/DCs, 1×10$^6$) for 3 days. FIG. 1B depicts exemplary experimental results demonstrating the cell percent and number of donor T cells in the spleen at 4 days, 7 days and 35 days after adoptive transfer. FIG. 1C depicts exemplary experimental results demonstrating IFN-γ-producing donor T cells at 7 days and 35 days after adoptive transfer. For FIG. 1D through FIG. 1F, equal number of memory Pmel-1 CD8$^+$ cells (4×10$^4$ cells/mouse), isolated from primary recipients of WT and Ezh2$^{-/-}$ naïve Pmel-1 cells 42 days after gp100/DC treatment, were transferred into sublethally irradiated secondary B6 recipients, followed by IL-2- and gp100/DC-treatment. Donor T cells were analyzed 7 days after adoptive transfer. FIG. 1D depicts exemplary experimental results demonstrating donor T cells were collected from the spleen of WT and Ezh2$^{-/-}$ Pmel-1 cell primary recipients 42 days after transfer, and separately transferred into sublethally irradiated secondary non-tumor-bearing B6 mice (4×10$^4$ cells/mouse), followed by treatment with IL-2 and gp100/DCs at 42 days, 43 days and 44 days. By 49 days, donor T cells were collected from the spleen of the secondary mice. Plots and graph show the percentage of donor Pmel-1 cells. FIG. 1E depicts exemplary experimental results demonstrating donor T cells derived from these secondary mice were activated with anti-CD3 Ab for 5 hours to measure their production of IFN-γ. The graph shows the number of IFN-γ$^+$ Pmel-1 cells in the spleen. FIG. 1F depicts exemplary experimental results demonstrating that donor T cells collected at 49 days from the secondary mice were cultured ex vivo with IL-7$^+$ IL-15 in the presence or absence of gp100 for additional 5 days. Plots and graphs show the percentage of donor T cells in cultures. p<0.05, and ***: p<0.001 (two-tailed unpaired t-test). Data are representatives of three independent experiments with n=5 mice per group in each.

FIG. 2, comprising FIG. 2A depicts exemplary experimental results demonstrating the cell percent and number of donor T cells in the LN at indicated time after adoptive transfer. FIG. 2B depicts exemplary experimental results demonstrating the cell percent and number of donor T cells in the PB at indicated time after adoptive transfer. Data are representatives of 2 independent experiments (n=3-9 mice per group in each, mean±SD). *: p<0.05, and **: p<0.01.

FIG. 3, comprising FIG. 3A depicts exemplary experimental plots and graphs showing the percentage of fraction of WT and Ezh2$^{-/-}$ T cells in the spleen. FIG. 3B depicts exemplary experimental graphs showing the percentage of Annexin-V$^+$ cells within WT and Ezh2$^{-/-}$ T cell population. FIG. 3C depicts exemplary experimental results demonstrating BrdU was administered to the recipient mice 16 hours before analysis. Graphs show the percentage of donor T cells with incorporated BrdU. FIG. 3D depicts exemplary experimental results demonstrating the percentage of IFN-γ-, IL-2-, and GzmB-expressing cells after gating on donor WT (Thy1.1$^+$CD45.2$^+$) and Ezh2$^{-/-}$ (Thy1.1$^-$CD45.2$^+$) CD8$^+$ T cells. For FIG. 3E and FIG. 3F, spleen mononuclear cells were recovered 35 days after adoptive transfer, cultured ex vivo for additional 5 days in the presence of IL-2 and IL-7, with or without addition of gp100. FIG. 3E depicts exemplary experimental plots and graphs showing the percentage of donor CD8$^+$ T cells (upper) and the percent of donor WT (Thy1.1$^+$) and Ezh2$^{-/-}$ (Thy1.1$^-$) cells after gating on donor CD8$^+$ T cells (C45.2$^+$). Graph shows the recovery rate of WT and Ezh2$^{-/-}$ T cell number after and before culture. FIG. 3F depicts exemplary experimental results demonstrating IFN-γ-producing Pmel-1 cells were measured using flow cytometric analysis. *: p<0.05, : p<0.01, and *: p<0.01 (two-tailed unpaired t-test). Data are representative of two independent experiments with n=3 mice per group in each experiment (mean±SD).

FIG. 4, comprising FIG. 4A depicts a schematic diagram of three characteristic phases of the T cell response and the possible role of Ezh2 in each phase. For FIG. 4B through FIG. 4G, WT and Ezh2$^{-/-}$ T$_N$ Pmel-1 cells (Thy1.1$^+$) were transferred into sublethally irradiated B6 mice (Thy1.2$^+$, n=3 for each group), followed by immunization with IL-2 and gp100/DCs for 3 days. FIG. 4B depicts exemplary experimental results demonstrating the fraction of KLRG1hi cells in donor T$_{CMP}$ (CD44$^-$CD62L$^{hi}$) and T$_{EFF}$ (CD44$^+$ CD62L$^{lo}$) T cells in the spleen. FIG. 4C depicts exemplary experimental results demonstrating the fraction of KLRG1hi cells in donor T$_{CMP}$ (CD44$^+$CD62L$^{hi}$) and T$_{EFF}$ (CD44$^+$ CD62L$^{lo}$) T cells in PB. FIG. 4D depicts exemplary experimental graphs showing the percentage of numbers of T$_{CMP}$ and T$_{EFF}$ (left panel) in the spleen at 4 days and 7 days after transfer. The right panel shows the percentage and numbers of MPCs and SLECs measured with KLRG-1 by CD127 at 4 days and 7 days after transfer. FIG. 4E depicts exemplary experimental results demonstrating the percentage of Annexin V-positive cells in the subpopulation of T$_{CMP}$ and T$_{EFF}$ derived from the spleen at 4 days and 7 days after transfer. FIG. 4F depicts exemplary experimental results demonstrating real-time RT-PCR measurement of p19$^{Arf}$ in the subset of T$_{CMP}$ and T$_{EFF}$ of 4 days and 7 days. FIG. 4G depicts exemplary experimental histograms show the expression of indicated surface markers on WT and Ezh2$^{-/-}$ Pmel-1 cells derived from the spleen at 4 days after transfer. For FIG. 4H and FIG. 4I, WT and Ezh2$^{-/-}$ naïve Pmel-1 cells (Thy1.1$^+$) were transferred into sublethally irradiated non-tumor-bearing B6 mice (Thy1.2$^+$), followed by immediate treatment with IL-2 and gp100/DCs for 3 days. By day 7 after transfer, donor Tc and T$_{EFF}$ were highly purified using FACS sorter, and transferred into sublethally irradiated secondary recipients that had been immunized with gp100/DCs 7 days earlier (described in FIG. 6). Forty-two days later, donor T cells were collected from the spleen of these secondary recipients (FIG. 4H), and further cultured ex vivo for additional 5 days (FIG. 4I). FIG. 4H and FIG. 4I depict exemplary experimental plots and graphs showing the frequency of donor T cells derived from the secondary recipients of WT and Ezh2$^{-/-}$ Tc and T$_{EFF}$. *: p<0.05, : p<0.01, and *: p<0.01 (two-tailed unpaired t-test). Data are representative of four independent experiments with n=3 mice per group in each (FIG. 4B through FIG. 4G; mean±SD) or two experiments with n=4 mice per group in each (FIG. 4H and FIG. 4I, mean±SD).

FIG. 5, comprising FIG. 5A depicts exemplary plots and graphs showing the percentage and number of T$_{CMP}$ and T$_{EFF}$. FIG. 5B depicts exemplary experimental results demonstrating the percentage and number of MPC and SLEC assessed by staining with KLRG-1 by CD127. FIG. 5C depicts exemplary histograms and graphs showing the expression of PD1 and CD122 on he surface of WT and Ezh2$^{-/-}$ CD8$^+$ T cells. *: p<0.05, : p<0.01, and *: p<0.001 (two-tailed unpaired t-test). Data are representative of two independent experiments with n=3 mice per group in each experiment (mean±SD).

FIG. 6, comprising FIG. 6A depicts exemplary dot plots showing the fraction of donor T cells in the spleen from mice at different days of infection. FIG. 6B depicts exemplary graphs showing the percentage of donor OVA$_{257-264}$ dimer-specific CD8$^+$ T cells in spleen, liver and PB. FIG. 6C depicts exemplary histograms and graphs showing the expression of Ki67 in donor-derived OVA$_{257-264}$ dimer-specific CD8$^+$ T cells. FIG. 6D and FIG. 6E depicts exemplary dot plots and graphs showing the frequency of KLRG1$^{hi}$ cells among donor OT-I-specific CD8$^+$ T cells. FIG. 6F depicts exemplary graphs showing the fraction of T$_{CMP}$ and T$_{EFF}$ among donor OVA$_{257-264}$ dimer-specific CD8$^+$ T cells. Data (mean±SD) are representatives of two independent experiments. *: p<0.05, : p<0.01, and *: p<0.001.

FIG. 7, comprising FIG. 7A depicts a schematic diagram of assessing the long-term impact of Ezh2 deficiency on the transition of memory precursor cells into mature memory T cells. WT and Ezh2$^{-/-}$ naïve Pmel-1 cells (1×10$^6$, Thy1.1$^+$) were transferred into sublethally irradiated B6 mice (Thy1.2$^+$), followed by treatment with IL-2 and gp100/DCs. T$_{CMP}$ and T$_{EFF}$ were highly purified using cell sorter from the spleen of these primary recipients 7 days after transfer and transferred into immunization-matched secondary lymphodepleted B6 mice. Forty-two d later, donor cells were isolated from the spleen of these secondary recipients to measure their memory cell properties. FIG. 7B depicts exemplary dot plots showing the fraction of WT and Ezh2$^{-/-}$ T$_{CMP}$ and T$_{EFF}$ before and after FACS sorting T cells pooled from 4 to 6 mice in each group.

FIG. 8, comprising FIG. 8A depicts a schematic experimental design. FIG. 8B depicts exemplary flow cytometric analysis showing gp100-specific CD8$^+$ T cells in the spleen 42 days after immunization. FIG. 8C depicts exemplary immunoblots of in vivo recovered CD8$^+$ cells that were treated with various concentration of TAT-Cre. FIG. 8D depicts exemplary plots and graphs showing the percentage and recovery rate of gp100-specific CD8$^+$ T cells in the culture with or without Ezh2 deletion by TAT-Cre. FIG. 8E depicts exemplary experimental results demonstrating IFN-γ production by gp100-specific CD8$^+$ T cells upon ex vivo deletion of Ezh2 and restimulation with gp100. *: p<0.05, and **: p<0.01 (two-tailed unpaired t-test). Data are representative of two independent experiments with n=3 mice per group in each experiment (mean±SD).

FIG. 9, comprising FIG. 9A depicts exemplary experimental results demonstrating a Venn diagram showing the number of differentially expressed genes. FIG. 9B depicts a table showing the signaling pathways most regulated by Ezh2 in activated Pmel-1 cells, which was identified by INGENUITY pathway analysis. FIG. 9C depicts a heat map showing the cluster of genes associated with Cell Function and Maintenance in activated WT and Ezh2$^{-/-}$ Pmel-1 cells, which was identified by INGENUITY pathway analysis. FIG. 9D and FIG. 9E depict exemplary experimental results demonstrating gene expression as assessed by real-time RT-PCR. *: p<0.05, and ***: p<0.001 (two-tailed unpaired t-test). Data are representative of four independent experiments (mean±SD).

FIG. 10, comprising FIG. 10A depicts exemplary graphs showing the change of selected transcripts for comparing paired groups by RNA-seq profiling analysis. FIG. 10B depicts exemplary experimental results demonstrating that WT and Ezh2$^{-/-}$ naïve Pmel-1 cells (Thy1.1$^+$) were transferred into sublethally irradiated B6 mice (Thy1.2$^+$, n=3 for each group), followed by treatment with IL-2 and gp100/DCs for 3 days as described in FIG. 1B. At day 7 of transfer, $T_{CMP}$ and $T_{EFF}$ were highly purified using FACS sorter to measure their expression of major TFs using real-time RT-PCR. For FIG. 10C and FIG. 10D, WT and Ezh2$^{-/-}$ naive Pmel-1 cells were cultured in the presence of anti-CD3/CD28 Abs and IL-2. Cells were collected 3 days latter for ChIP analysis. FIG. 10C depicts an exemplary ChIP analysis of the deposition of Ezh2 or IgG in WT T cells at the different regions of these major TF loci. FIG. 10D depicts an exemplary ChIP analysis of the deposition of Ezh2, H3K27me3 or IgG within WT and Ezh2$^{-/-}$ T cells at the promoter region of these major TF loci. *: p<0.05, : p<0.01, and *: p<0.001 (two tailed unpaired t-test). Data are representative of three independent experiments (mean±SD).

FIG. 11, comprising FIG. 11A depicts an exemplary immunoblot analysis of Pmel-1 cells before and after TCR-activation, probed with anti-Ezh2 Ab. FIG. 11B depicts an exemplary immunoblot analysis of Pmel-1 cells before and after TCR-activation, probed with anti-H3K27me3 Ab. FIG. 11C depicts an exemplary ChIP analysis of Ezh2 binding to the promoter regions of major TF loci. FIG. 11D depicts exemplary immunoblots of the expression of indicated proteins. *: p<0.05, and *: p<0.001 (two-tailed unpaired t-test). Data are representative of three independent experiments (FIG. 11A and FIG. 11D), or two experiments with T cells pooled from four mice in each (FIG. 11B and FIG. 11C**, mean±SD).

FIG. 12, comprising FIG. 12A depicts exemplary immunoblots using anti-Ezh2, anti-H3K27me3 and anti-H3. FIG. 12B depicts an exemplary real-time PCR analysis of major TF transcripts. FIG. 12C depicts an exemplary ChIP analysis of Ezh2 binding to the promoter regions of these major TF loci. FIG. 12D depicts exemplary immunoblots of the expression of indicated proteins. *: p<0.05, and *: p<0.001 (two-tailed unpaired t-test). Data are representative of three independent experiments (FIG. 12A and FIG. 12D), or two experiments with T cells pooled from four mice in each (FIG. 12B and FIG. 12C**, mean±SD).

FIG. 13, comprising FIG. 12A depicts exemplary experimental results demonstrating that WT Pmel-1 cells were stimulated with anti-CD3/CD28 Ab+IL-2. Immunoblot analysis of Pmel-1 cells stimulated in vitro for 3 days, 5 days and 7 days, probed with anti-Ezh2 and anti-phosphorylated Ezh2$_{2S1}$. Unstimulated $T_N$ were used as control. FIG. 13B through FIG. 13D depict exemplary immunoblot analysis of Pmel-1 CD8$^+$ T cells stimulated in vitro for 7 days, with or without treatment of MK2206, probed with indicated Abs. FIG. 13E through FIG. 13G depict exemplary experimental results demonstrating WT Pmel-1 cells were cultured with anti-CD3/CD28 Ab+IL-2, with or without treatment of PI103, MK2206 or rapamycin for 7 days. FIG. 13E depicts an exemplary real-time RT-PCR analysis of Ezh2-targeted genes. ChIP analysis of cultured Pmel-1 cells treated with PI103, or MK2206. FIG. 13F depicts an exemplary graph showing the deposition of Ezh2 at the promoter regions of Id3, Id2, Prdm1 and Eomes. FIG. 13G depicts an exemplary graph showing the deposition of H3K27me3 at the promoter regions of Id3, Id2, Prdm1 and Eomes. FIG. 13H through FIG. 13K depict exemplary experimental results demonstrating WT Pmel-1 cells were stimulated with anti-CD3/CD28 Ab for 36 hours, followed by infection with MigR1 retrovirus (GFP) or MigR1 retrovirus encoding flag-tagged Ezh2, or Ezh2$_{S21A}$. Pmel-1 cells were collected at day 7 after culture. FIG. 13H depicts an exemplary immunoblot analysis of GFP and Ezh2$_{S21A}$ Pmel-1 cells, probed with indicated Abs. FIG. 13I depicts an exemplary real-time RT-PCR analysis of their expression of major TFs. FIG. 13J depicts an exemplary ChIP analysis showing the deposition of Ezh2 at the promoter regions of major TF loci. FIG. 13K depicts an exemplary ChIP analysis showing the deposition of H3K27me3 at the promoter regions of major TF loci.*: p<0.05, : p<0.01, and *: p<0.001 (two-tailed unpaired t-test). Data are representatives of three independent experiments (FIG. 13A through FIG. 13D), or two experiments (FIG. 13E through FIG. 13K; mean±SD).

FIG. 14, comprising FIG. 14A depicts exemplary flow cytometric analysis of the expression of Ezh2 in WT and Ezh2$^{-/-}$ T cells at 0 days, 3 days and 5 days after transfer. FIG. 14B depicts exemplary flow cytometric analysis of the expression of H3K27me3 in WT and Ezh2$^{-/-}$ T cells at 0 days, 3 days and 5 days after transfer. FIG. 14C depicts exemplary flow cytometric analysis of the expression of pEzh2 in WT and Ezh2$^{-/-}$ T cells at 0 days, 3 days and 5 days after transfer. Histograms (left) show the representative flow cytometric analysis results from donor T cells collected at day 5 after transfer. Graphs (right) show the mean fluorescence intensity of tested molcules. Data are representative of two independent experiments with n=3 mice per group in each (mean±SD).

FIG. 15, comprising FIG. 15A depicts an exemplary experiment scheme. FIG. 15A depicts an exemplary immunoblot analysis of Pmel-1 cells transduced with GFP, Ezh2, Ezh2$_{S21D}$ and Ezh2$_{S21A}$, probed with Flag, H3K27me3 and H3. FIG. 15C depicts an exemplary RT-PCR analysis of gene expression in Pmel-1 cells transduced by indicated genes. For FIG. 15D and FIG. 15E, 7 day-Pmel-1 cells (Thy1.1$^+$) were transferred into sublethally irradiated B6 mice (Thy1.2$^+$), followed by treatment with IL-2 and gp100/DCs for 3 days after transfer. FIG. 15D depicts the results of an exemplary experiment demonstrating that donor T cells were collected from the spleen, PB and LN at 6 days after adoptive transfer, and measured by flow cytometric analysis. FIG. 15E depicts exemplary plots and graphs showing the percentage of Id3$^{hi}$, KLRG1$^{hi}$, CD62L$^+$ and IFN-γ$^+$ within donor T cells from the spleen. *: p<0.05, : p<0.01, and *: p<0.001 (two tailed unpaired t-test). Data are representatives of three experiments (FIG. 15B and FIG. 15C; mean±SD) or two experiments with n=4 mice per group in each (FIG. 15D and FIG. 15E; mean±SD).

FIG. 16, comprising FIG. 16A depicts the results of exemplary experiments demonstrating that tumor size was monitored over time. Some recipient mice were killed at day 9 to examine the presence of donor Pmel-1 cells in the spleen using flow cytomeric analysis. FIG. 16B depicts exemplary graphs showing the percentage of indicated total cells and cell subsets. For FIG. 16C through FIG. 16H, B6 mice with pre-established B16 melanoma cells received no adoptive transfer (Non-T cells), transfer of in vitro expanded 7 day Pmel-1 cells infected with MigR1 encoding GFP, Ezh2 or Ezh2$_{S21A}$ (5×10$^5$ T cells/mouse), followed by treatment with IL-2 and gp100/DCs from day 0-day 3 and repeated once more from day 18-day 20. FIG. 16C depicts the results of exemplary experiments demonstrating that tumor size was monitored over time. FIG. 16D depicts exemplary experimental results demonstrating the percentage of total donor Pmel-1 cells in circulating PB from each group of mice receiving GFP-, Ezh2- and Ezh2$_{S21A}$-7 day Pmel-1 cells over a period of 24 days after transfer. FIG. 16E depicts exemplary experimental results demonstrating the percentage of KLRG-1$^{hi}$ Pmel-1 cells in circulating PB from each group of mice receiving GFP-, Ezh2- and Ezh2$_{S21A}$-7 day Pmel-1 cells over a period of 24 days after transfer. For FIG. 16F through FIG. 16H, in separate experiments as described in FIG. 16C through FIG. 16E above, donor T cells were recovered from the spleen and tumor at 21 days after transfer. FIG. 16F depicts exemplary plots showing the percentage of transferred GFP$^+$ cells in tumor and spleen by gating on donor Thy1.1$^+$ Pmel-1 CD8$^+$ cells, with Pmel-1 cells prior to transfer as controls. FIG. 16G depicts exemplary graphs showing the number of total donor GFP$^+$ Thy1.1$^+$ Pmel-cells and IFN-γ$^+$ Pmel-1 cells in the spleen and tumor. FIG. 16H depicts exemplary plots showing the expression of CD62L on the surface of donor GFP$^+$Thy1.1$^+$ T cells derived from the spleen and tumor. *: p<0.05, : p<0.01, and *: p<0.001 (two-tailed unpaired t-test). Data are pooled from two experiments (FIG. 16A; .GFP, n=9; Ezh2, n=9; S21A, n=10; mean±SD) or are representative of two independent experiments (FIG. 16B; n=3-5 mice per group in each, mean±SD; FIG. 16C-FIG. 16H; n=5 mice per group in each, mean±SD).

FIG. 17, comprising FIG. 17A depicts exemplary plots show cells before and after sorting. FIG. 17B depicts exemplary real-time RT-PCR measurement of transduced genes. Data are representatives of two independent experiments.

FIG. 18, comprising FIG. 18A depicts exemplary experimental results demonstrating the percentage and numbers of donor T cells collected from the spleen 35 days after transfer. FIG. 18B depicts exemplary experimental results demonstrating the surface phenotype of donor T cells collected from the spleen 35 days after transfer. FIG. 18C depicts exemplary experimental results demonstrating the production of IFN-γ of donor T cells collected from the spleen 35 days after transfer. Dot plots and graphs in FIG. 18C show the percent of IFN-γ$^+$ cells within donor Thy1.1$^+$ T cells. For FIG. 18D, 3T3 cells were transduced with an Id3-specific pGL3 luciferase reporter (Id3-pGL), together with MigR1-GFP, MigR1-Ezh2$_{S21A}$ or MigR1-Ezh2$_{S21D}$. Id2-specific pGL3 luciferase reporter (Id2-pGL) was used as control. FIG. 18D depicts an exemplary graph showing the fold change of luciferase reporter activity. Data (mean±SD) are representatives of three independent experiments. For FIG. 18E through FIG. 18F, 3T3 cells were transduced with pL-CRISPR.EFS.GFP plasmid or pL-CRISPR.EFS.GFP plasmid encoding guide RNA targeting Ezh2. Three days later, GFP$^+$ cells were sorted into single cell using FACS sorter to select Ezh2-knockout cell clones. FIG. 18E depicts exemplary immunoloblots showing the loss of Ezh2 in 3T3 cells with Ezh2 knockout. These Ezh2-null 3T3 cells were reconstituted with MigR1-GFP vector and MigR1 encoding Ezh2, Ezh2$_{S21A}$ or Ezh2$_{H689A}$. Id3-pGL luciferase reporter was introduced to these cells for reporter assay. In some experiments, WT 3T3 cells were treated with DZNep to deplete Ezh2 protein. FIG. 18F depicts an exemplary graph showing the fold change of luciferase reporter activity. For FIG. 18G, WT Pmel-1 cells were stimulated with anti-CD3/CD28 Ab+IL-2 for 7 days for ChIP analysis. FIG. 18G depicts exemplary graphs showing the deposition of H3K4me3, H3K27me3 and Pol II at the promoter regions of Id3 and Id2. FIG. 18H depicts an exemplary ChIP analysis of WT and Ezh2$^{-/-}$ T$_N$ Pmel-1 cells (Thy1.1$^+$) stimulated with anti-CD3/CD28 Ab+IL-2 for 7 days. FIG. 18G depicts a graphic summary of Ezh2 effects on memory formation and function. *: p<0.05, : p<0.01, and *: p<0.001 (two-tailed unpaired t-test). Data are representatives of two experiments with n=3-4 mice per group in each (FIG. 18A through FIG. 18C, mean±SD), or three independent experiments (FIG. 18D through FIG. 18F, mean±SD).

FIG. 19, comprising FIG. 19A depicts exemplary experimental results demonstrating RAJITGL were injected (i.v.) into immune deficient NSG mice at day 0 to induced systemic leukemia, followed with or without injection (i.v.) of CD4+ and CD8+ CD19-BBζ-CAR T cells at day 3. In vivo imaging was used to monitor leukemia growth. FIG. 19B depicts exemplary western blot demonstrating the expression of EZH2 in BBζ-CAR and 2ζ-CAR CD8+ T cells at day 20 after incubation. FIG. 19C depicts exemplary experimental results of a flow cytometric analysis demonstrating the level of intracellular T-BET and ID2.

DETAILED DESCRIPTION

Figures 1A, 1B, 1C, 1D, 1E, 1F:
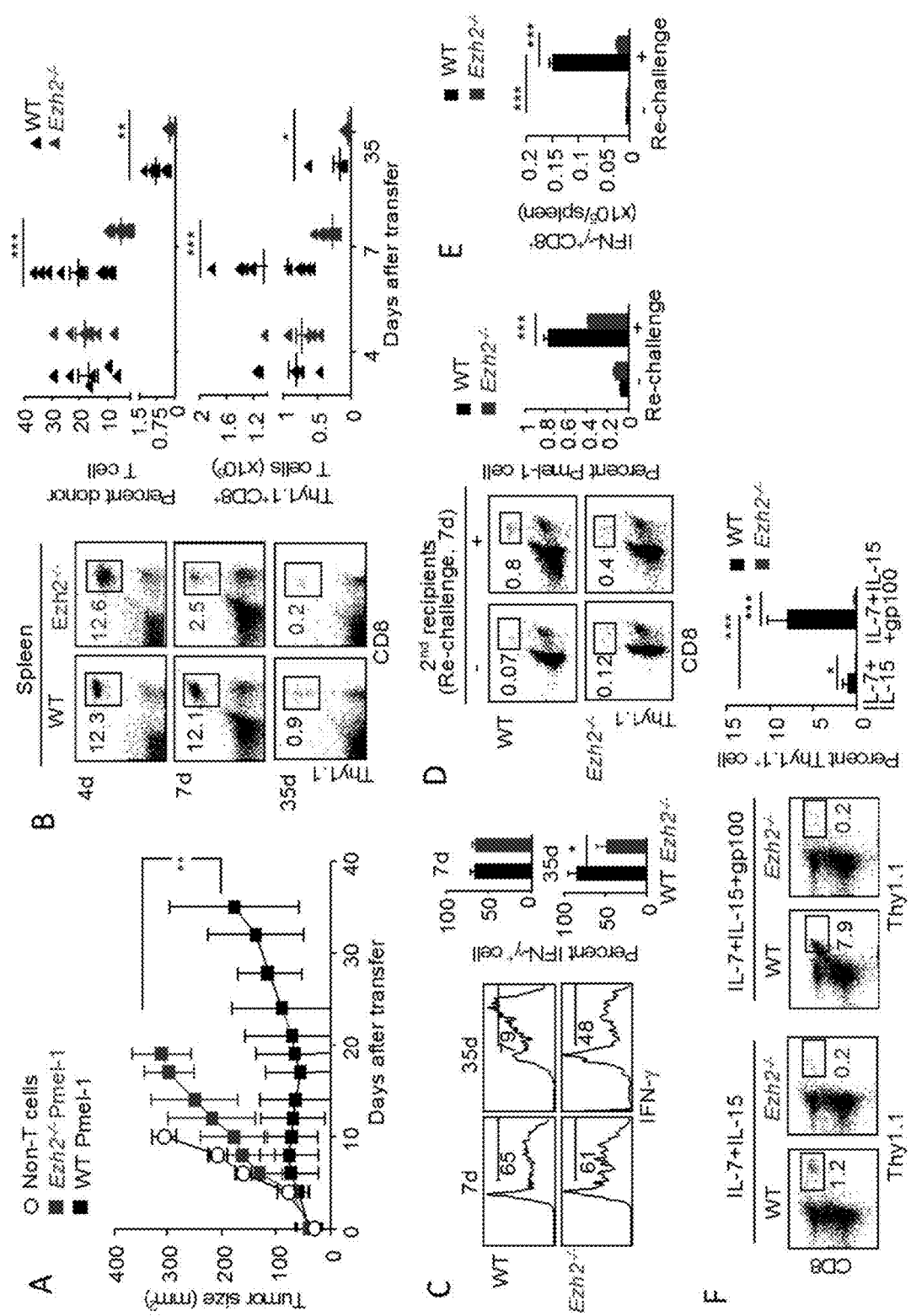
FIG. 1A through FIG. 1F, depicts exemplary experimental results demonstrating that Ezh2 is required for CD8+ T cells to control tumor growth and maintain memory formation.

In one embodiment, the invention provides methods and compositions for use in generating improved T cells for use in adoptive T cell therapy.

In one embodiment, the invention provides compositions and methods for modifying at least one of the level and activity of a gene regulated by Ezh2 in a T cell. In one embodiment, the invention relates compositions and methods for increasing at least one of the level and activity of a gene upregulated by Ezh2. In one embodiment, the invention relates to compositions and methods for increasing at least one of the level and activity of Id3 in a T cell. In one embodiment, the invention relates compositions and methods for decreasing at least one of the level and activity of a gene downregulated by Ezh2. In one embodiment, the invention relates to compositions and methods for decreasing at least one of the level and activity of at least one of Id2, Prdm1 and Eomes in a T cell.

In one embodiment, the invention provides compositions and methods for increasing at least one of the level and activity of Ezh2 in T cells. Ezh2 catalyzes H3K27me3. Therefore, in one embodiment, the invention provides compositions and methods for increasing H3K27me3 activity in cells. In one embodiment, the invention relates to compositions and methods that can selectively reduce Akt phosphorylation of Ezh2 in proliferating T cells without impairing effector differentiation.

In one embodiment, the methods and compositions of the invention reduce the level of Ezh2 phosphorylation by Akt. In one embodiment, a method of reducing the level of Ezh2 phosphorylation is through using a variant of Ezh2 that does not get phosphorylated by Akt.

In one embodiment, the invention provides vectors for expression of an Akt-insensitive Ezh2 protein. In one embodiment, the invention provides a vector encoding an Ezh2S21A protein. In one embodiment, the vector is a retroviral vector. In one embodiment, the vector is a self-inactivating lentiviral vector as described elsewhere herein. In one embodiment the vector is delivered (e.g., by transfecting or electroporating) to a T cell wherein the vector comprises an Ezh2S21A transgene, which is transcribed as an mRNA molecule. In one embodiment, the invention provides cells transformed with a vector comprising an Ezh2S21A transgene. Therefore, in various embodiments, the invention includes compositions comprising genetically improved T cells engineered to express Ezh2S21A and methods of using a genetically improved T cell engineered to express Ezh2S21A. In one embodiment, the T cell is a tumor-reactive T cell. In one embodiment, the T cell is a CART cell.

In one embodiment, a method of reducing the level of Ezh2 phosphorylation is through inhibiting Akt or inhibiting a protein or pathway that leads to Akt phosphorylation of Ezh2. Therefore, in one embodiment, the invention provides methods of generating T cells having increased Ezh2 activity through contacting the T cell with one or more inhibitor of Akt or an inhibitor of a protein or pathway that leads to Akt phosphorylation of Ezh2. In one embodiment, the T cell is contacted with at least one inhibitor of calcinurin, JMJD3, AKT and AP-1. In one embodiment, the T cell is contacted with a combination of at least four inhibitors to inhibit all of calcinurin, JMJD3, AKT and AP-1.

In one embodiment, the invention provides improved T cells generated according to the methods of the invention. In one embodiment, the improved T cell of the invention is a multipotent T memory stem cell ($T_{SCM}$). In one embodiment, the improved T cell of the invention is an induced multipotent T memory stem cell ($iT_{SCM}$).

In one embodiment, the T cell is a CART cell. In one embodiment, the CART cell expresses Ezh2S21A. Therefore, in one embodiment, the invention relates to methods and compositions for generating Ezh2S21A expressing CART cells and use thereof. In one embodiment, the CART cell is contacted with at least one inhibitor of calcinurin, JMJD3, AKT and AP-1. In one embodiment, the CART cell is contacted with a combination of at least four inhibitors to inhibit all of calcinurin, JMJD3, AKT and AP-1.

In one embodiment, the T cell of the invention is used for treatment of a disease or disorder. In one embodiment, the disease or disorder is cancer, including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, glioblasoma, neuroblasoma, and the like.

In one embodiment, the T cell of the invention is used for treatment of chronic infections, including but not limited to HIV infection, hepatitis infection, CMV-infection, EBV infection, and the like.

In one embodiment, the invention includes autologous cells from a subject having a cancer that are cultured in the presence of at least one agent that modulates Ezh2 or Akt function. In one embodiment, the autologous cells are cultured in the presence of at least one at least one inhibitor of calcinurin, JMJD3, AKT and AP-1. In one embodiment, the autologous cells are genetically modified (for example, by transfecting or electroporating an RNA molecule encoding a desired CAR into the T cell.)

In one embodiment, the T cell of the invention may be a TCR-transgenic T cell, a Tumor infiltrating T cell (TIL) or any T cell that can be used for treating a disease or disorder (for example, treating chronic infection or cancer.)

Definitions

Unless defined otherwise, all technical and scientific terms used herein have the same meaning as commonly understood by one of ordinary skill in the art to which the invention pertains. The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

As used herein, the term "Chimeric Antigen Receptor" or alternatively a "CAR" refers to a recombinant polypeptide construct comprising at least an extracellular antigen binding domain, a transmembrane domain and a cytoplasmic signaling domain comprising a functional signaling domain derived from a stimulatory molecule as defined herein. In one embodiment, the stimulatory molecule is the chain ζ associated with the T cell receptor complex. In one embodiment, the intracellular signaling domain further comprises one or more functional signaling domains derived from at least one costimulatory molecule as defined below. In one embodiment, the costimulatory molecule is 4-1BB (i.e., CD137). In one embodiment, the CAR comprises a chimeric fusion protein comprising an extracellular antigen recognition domain, a transmembrane domain and a cytoplasmic signaling domain comprising a functional signaling domain derived from a stimulatory molecule. In one embodiment, the CAR comprises a chimeric fusion protein comprising an extracellular antigen recognition domain, a transmembrane domain and a cytoplasmic signaling domain comprising a functional signaling domain derived from a co-stimulatory molecule and a functional signaling domain derived from a stimulatory molecule. In one embodiment, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one embodiment, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one embodiment the CAR comprises an optional leader sequence at the amino-terminus (N-ter) of the CAR fusion protein. In one embodiment, the CAR further comprises a leader sequence at the N-terminus of the extracellular antigen recognition domain, wherein the leader sequence is optionally cleaved from the scFv domain during cellular processing and localization of the CAR to the cellular membrane. As used herein, the terms intracellular and cytoplasmic are used interchangeably.

The term "antibody," as used herein, refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes, but is not limited to, monoclonal antibodies, human antibodies, humanized antibodies, camelid antibodies, and chimeric antibodies. The antibodies can be of any isotype/class (e.g., IgG, IgE, IgM, IgD, IgA and IgY), or subclass (e.g., IgG1, IgG2, IgG3, IgG4, IgA1 and IgA2).

The term "antibody fragment" refers to at least one portion of an intact antibody, or recombinant variants thereof, and refers to the antigen binding domain, e.g., an antigenic determining variable regions of an intact antibody that is sufficient to confer recognition and specific binding of the antibody fragment to a target, such as an antigen. Examples of antibody fragments include, but are not limited to, Fab, Fab', F(ab')2, and Fv fragments, single chain or "scFv" antibody fragments, linear antibodies, single domain antbodies such as sdAb (either $V_L$ or $V_H$), camelid $V_{HH}$ domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

The portion of the CAR composition of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426). In one embodiment, the antigen binding domain of a CAR composition of the invention comprises an antibody fragment. In a further embodiment, the CAR comprises an antibody fragment that comprises a scFv.

By the term "recombinant antibody" as used herein, is meant an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant or synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated, synthesized or can be derived from a biological sample, or it can be a macromolecule that is not necessarily a polypeptide. Such a biological sample can include, but is not limited to a tissue sample, a tumor sample, a cell or a fluid with other biological components.

The term "anti-tumor effect" as used herein, refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to whom it is later to be re-introduced.

"Allogeneic" refers to any material derived from a different animal of the same species as the individual to whom the material is introduced. Two or more individuals are said to be allogeneic to one another when the genes at one or more loci are not identical. In some embodiments, allogeneic material from individuals of the same species may be sufficiently unlike genetically to interact antigenically.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, primary or metastatic melanoma, thymoma, lymphoma, sarcoma, lung cancer, liver cancer, non-Hodgkin's lymphoma, Hodgkins lymphoma, leukemia, uterine cancer, cervical cancer, bladder cancer, kidney cancer and adenocarcinomas such as breast cancer, prostate cancer, ovarian cancer, pancreatic cancer, glioblastoma, neuroblastoma, and the like.

As used herein, the term "conservative sequence modifications" is intended to refer to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody or antibody fragment of the invention can be replaced with other amino acid residues from the same side chain family and the altered antibody or antibody fragment can be tested for the ability to bind the target using the functional assays described herein.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule expressed by a T cell that provide the primary cytoplasmic signaling sequence(s) that regulate primary activation of the TCR complex in a stimulatory way for at least some embodiment of the T cell signaling pathway. In one embodiment, the primary signal is initiated by, for instance, binding of a TCR/CD3 complex with an MHC molecule loaded with peptide, and which leads to mediation of a T cell response, including, but not limited to, proliferation, activation, differentiation, and the like. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the invention include those derived from TCR ζ, FcR gamma, FcR beta, CD3 gamma, CD3 delta, CD3 epsilon, CD5, CD22, CD79a, CD79b, CD278 (also known as "ICOS") and CD66d. In a specific CAR of the invention, the cytoplasmic signaling molecule in any one or more CARs of the invention comprises a cytoplasmic signaling sequence derived from CD3ζ. In a specific CAR of the invention, the cytoplasmic signaling sequence derived from CD3ζ is the human sequence, or the equivalent residues from a non-human species, e.g., mouse, rodent, monkey, ape and the like.

An "antigen presenting cell" or "APC" as used herein, means an immune system cell such as an accessory cell (e.g., a B-cell, a dendritic cell, and the like) that displays foreign antigens complexed with major histocompatibility complexes (MHC's) on their surfaces. T-cells may recognize these complexes using their T-cell receptors (TCRs). APCs process antigens and present them to T-cells.

As used herein "ζ" or alternatively "ζ chain", "CD3ζ" or "TCRζ" is defined as the protein provided as GenBank accession No. BAG36664.1, or the equivalent residues from a non-human species, e.g., mouse, rodent, monkey, ape and the like, and a "ζ stimulatory domain" or alternatively a "CD3ζ stimulatory domain" or a "TCRζ stimulatory domain" is defined as the amino acid residues from the cytoplasmic domain of the chain ζ that are sufficient to functionally transmit an initial signal necessary for T cell activation. In one embodiment the cytoplasmic domain of ζ comprises residues 52 through 164 of GenBank accession No. BAG36664.1 or the equivalent residues from a non-human species, e.g., mouse, rodent, monkey, ape and the like, that are functional orthologs thereof.

A "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to an MEW class I molecule, BTLA and a Toll ligand receptor, as well as OX40, CD27, CD28, CDS, ICAM-1, LFA-1 (CD11a/CD18) and 4-1BB (CD137).

As used herein "4-1BB" is defined as member of the TNFR superfamily with an amino acid sequence provided as GenBank accession No. AAA62478.2, or the equivalent residues from a non-human species, e.g., mouse, rodent, monkey, ape and the like; and a "4-1BB costimulatory domain" are defined amino acid residues 214-255 of GenBank accession No. AAA62478.2, or the equivalent residues from a non-human species, e.g., mouse, rodent, monkey, ape and the like. In one embodiment, the "4-1BB costimulatory domain" is the human sequence or the equivalent residues from a non-human species, e.g., mouse, rodent, monkey, ape and the like. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene, cDNA, or RNA encodes a protein if transcription and translation of mRNA corresponding to that gene, cDNA, or RNA produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins or a RNA may also include introns to the extent that the nucleotide sequence encoding the protein may in some version contain an intron(s).

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its regulatory sequences.

A "transfer vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, polylysine compounds, liposomes, and the like. Examples of viral transfer vectors include, but are not limited to, adenoviral vectors, adeno-associated virus vectors, retroviral vectors, lentiviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragments) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies or antibody fragments can comprise residues which are found neither in the recipient antibody or antibody fragment nor in the imported CDR or framework sequences. These modifications are made to further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody or fragment, where the whole molecule is of human origin or consists of an amino acid sequence identical to a human form of the antibody or immunoglobulin.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

A "lentiviral vector" is a vector derived from at least a portion of a lentivirus genome, including especially a self-inactivating lentiviral vector as provided in Milone et al., Mol. Ther. 17(8): 1453-1464 (2009). Other Examples or lentivirus vectors that may be used in the clinic as an alternative to the pELPS vector, include but not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "operably linked" or alternatively "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, where necessary to join two protein coding regions, are in the same reading frame.

"Parenteral" administration of an immunogenic composition includes, e.g., subcutaneous (s.c.), intravenous (i.v.), intramuscular (i.m.), or intrasternal injection, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "flexible polypeptide linker" as used in the context of an scFv refers to a peptide linker that consists of amino acids such as glycine and serine residues used alone or in combination, to link variable heavy and variable light chain regions together. In one embodiment, the flexible polypeptide linker is a Gly/Ser linker and comprises the amino acid sequence (Gly-Gly-Gly-Ser)n, where n is a positive integer equal to or greater than 1. For example, n-1, n-2, n-3. n-4, n-5 and n-6, n-7, n-8, n-9 and n-10. In one embodiment, the flexible polypeptide linkers include, but are not limited to, (Gly4 Ser)4 or (Gly4 Ser)3 In another embodiment, the linkers include multiple repeats of (Gly2Ser), (GlySer) or (Gly3Ser). Also included within the scope of the invention are linkers described in WO2012/138475, incorporated herein by reference in its entirety).

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals including human).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

By the term "synthetic" as it refers to a nucleic acid or polypeptide, including an antibody, is meant a nucleic acid, polypeptide, including an antibody, which has been generated by a mechanism not found naturally within a cell. In some instances, the term "synthetic" may include and therefore overlap with the term "recombinant" and in other instances, the term "synthetic" means that the nucleic acid, polypeptide, including an antibody, has been generated by purely chemical or other means.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses.

By the term "specifically binds," as used herein, is meant an antibody or antigen binding fragment thereof, or a ligand, which recognizes and binds with a cognate binding partner (e.g., a stimulatory and/or costimulatory molecule present on a T cell) protein present in a sample, but which antibody, antigen binding fragment thereof or ligand does not substantially recognize or bind other molecules in the sample.

Ranges: throughout this disclosure, various embodiments of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Provided herein are methods for generating T cells with increased EZH2 signaling, compositions of matter comprising the improved T cells and methods of use for the treatment of diseases.

In one embodiment, an improved T cell of the invention having increased EZH2 signaling expresses a construct comprising an EZH2 gene that is not responsive to Akt phosphorylation. In one embodiment, the T cells express EZH2S21A. Therefore, in one embodiment the present invention provides EZH2S21A expression constructs and methods for their use in generating recombinantly engineered T cells.

In one embodiment, the invention provides methods of generating improved T cells comprising contacting a T cell with at least one inhibitor of the Akt pathway and compositions comprising T cells that have been contacted with at least one inhibitor of the Akt pathway.

In one embodiment the invention provides an improved T cell generated according to a method of the invention. In one embodiment, the T cells may be CART cells, TCR-transgenic T cells, Tumor infiltrating T cells (TIL) or any T cell that can be used for treating a disease or disorder.

In one embodiment, the T cell is a CART cell. In one embodiment, the CART cells cultured in the presence of at least one inhibitor of the Akt pathway can be used in methods for treating a disease or disorder in a subject. In one embodiment, the CART cells are engineered to express a chimeric antigen receptor (CAR), wherein the CAR T cell exhibits an antitumor property. In one embodiment, the antigen is CD19 and the CAR T cell is a CD19-CART cell. In one embodiment, the CD19-CART comprises at least one intracellular domain selected from the group of a CD137 (4-1BB) signaling domain, a CD3ζ signal domain, and a combination thereof.

Furthermore, the present invention provides methods for use of the improved T cells of the invention for treating or preventing a disease or disorder in a subject. In various embodiments, the disease or disorder is a cancer or a malignancy or a chronic infection (for example, HIV infection, hepatitis infection, CMV-infection, EBV infection, and the like.)

Modulators of Ezh2 Activity

In one embodiment, an improved T cell of the invention has increased EZH2 expression. Therefore, in various embodiments, the invention relates to T cells that have been contacted with a modulator of at least one of the level and activity of Ezh2. In one embodiment, the present invention comprises a pharmaceutical composition comprising a modulator (e.g., activator or inhibitor) of Ezh2 or a target of Ezh2. In various embodiments, the present invention includes compositions for modulating at least one of the level and activity of Ezh2 in a subject, a cell, a tissue, or an organ in need thereof. In various embodiments, the compositions of the invention modulates the amount of polypeptide of Ezh2, the amount of mRNA of Ezh2, the activity of Ezh2, the phosphorylation state of Ezh2 or a combination thereof. In various embodiments, the present invention includes compositions for modulating at least one of the level and activity of at least one gene regulated by Ezh2 in a subject, a cell, a tissue, or an organ in need thereof. In various embodiments, the compositions of the invention modulates the amount of polypeptide of at least one gene regulated by Ezh2, the amount of mRNA of at least one gene regulated by Ezh2, the activity of at least one gene regulated by Ezh2 or a combination thereof.

The compositions of the invention include compositions for generating improved T cells for use in treating or preventing cancer.

Activators

In one embodiment, the composition comprising an improved T cell of the invention comprises a T cell that has been contacted with an activator of Ezh2 or an activator of a gene positively regulated by Ezh2. In one embodiment, the activator of the invention increases the amount of Ezh2 polypeptide, the amount of Ezh2 mRNA, the amount of Ezh2 activity, the amount of phosphorylated Ezh2 or a combination thereof.

In one embodiment, an activity of Ezh2 is to catalyze H3K27me3. Therefore, in one embodiment the invention relates to methods and compositions for use in activating H3K27me3.

In one embodiment, the activator of the invention increases the amount of polypeptide of at least one gene positively regulated by Ezh2, the amount of mRNA of at least one gene positively regulated by Ezh2, the activity of at least one gene positively regulated by Ezh2, or a combination thereof. Genes positively regulated by Ezh2 include, but are not limited to, genes listed in Table 3 in bold. In one embodiment, a gene positively regulated by Ezh2 is Id3.

It will be understood by one skilled in the art, based upon the disclosure provided herein, that an increase in the level of Ezh2 or a gene positively regulated by Ezh2 encompasses the increase in gene expression, including transcription, translation, or both. The skilled artisan will also appreciate, once armed with the teachings of the present invention, that an increase in the level of Ezh2 or a gene positively regulated by Ezh2 includes an increase in protein activity. Thus, increasing at least one of the level and activity of Ezh2 or a gene positively regulated by Ezh2 includes, but is not limited to, increasing the amount of polypeptide, increasing transcription, translation, or both, of a nucleic acid encoding Ezh2 or a gene positively regulated by Ezh2; and it also includes increasing any activity of a polypeptide of Ezh2 or a gene positively regulated by Ezh2 as well.

Thus, the present invention relates to the generation of improved T cells genetically engineered with a Ezh2 polypeptide, a recombinant Ezh2 polypeptide, an active Ezh2 polypeptide fragment, or an activator of Ezh2 expression or activity.

In one embodiment, the activator of an activity of Ezh2 comprises a modified Ezh2 protein that has a decreased level of phosphorylation at serine 21. Therefore, in one embodiment, the invention relates to improved T cells genetically engineered with a modified Ezh2 protein that is unable to be phosphorylated at serine 21. In one embodiment, a modified Ezh2 protein that is unable to be phosphorylated at serine 21 comprises an alanine residue at amino acid residue 21 (Ezh2S21A.)

Activation of Ezh2 or a gene positively regulated by Ezh2 can be assessed using a wide variety of methods, including those disclosed herein, as well as methods well-known in the art or to be developed in the future. That is, the routineer would appreciate, based upon the disclosure provided herein, that increasing at least one of the level and activity of Ezh2 or a gene positively regulated by Ezh2 can be readily assessed using methods that assess the level of a nucleic acid encoding Ezh2 or a gene positively regulated by Ezh2 (e.g., mRNA) and/or the level of polypeptide of Ezh2 or a gene positively regulated by Ezh2 in a biological sample obtained from a subject.

An activator of the invention can include, but should not be construed as being limited to, a chemical compound, a protein, a peptidomemetic, an antibody, a nucleic acid molecule. One of skill in the art would readily appreciate, based on the disclosure provided herein, that an activator encompasses a chemical compound that increases the level, enzymatic activity, or the like of Ezh2 or a gene positively regulated by Ezh2. Additionally, an activator encompasses a chemically modified compound, and derivatives, as is well known to one of skill in the chemical arts.

Further, one of skill in the art would, when equipped with this disclosure and the methods exemplified herein, appreciate that an activator includes such activators as discovered in the future, as can be identified by well-known criteria in the art of pharmacology, such as the physiological results of activation of Ezh2 or a gene positively regulated by Ezh2 as described in detail herein and/or as known in the art. Therefore, the present invention is not limited in any way to any particular activator as exemplified or disclosed herein; rather, the invention encompasses those activators that would be understood by the routineer to be useful as are known in the art and as are discovered in the future.

Further methods of identifying and producing an activator are well known to those of ordinary skill in the art, including, but not limited, obtaining an activator from a naturally occurring source. Alternatively, an activator can be synthesized chemically. Further, the routineer would appreciate, based upon the teachings provided herein, that an activator can be obtained from a recombinant organism. Compositions and methods for chemically synthesizing activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding protein to cells or tissues. Therefore, the invention includes a method of modifying a T cell to comprise a protein or a nucleic acid encoding a protein that is an activator of Ezh2 or a gene positively regulated by Ezh2.

One of skill in the art will realize that diminishing at least one of the level and activity of a molecule that itself diminishes at least one of the level and activity of Ezh2 or a gene positively regulated by Ezh2 can serve to increase at least one of the level and activity of Ezh2 or a gene positively regulated by Ezh2. Any inhibitor of a regulator of Ezh2 or a gene positively regulated by Ezh2 is encompassed in the invention. As a non-limiting example, antisense is described as a form of inhibiting a regulator of Ezh2 or a gene positively regulated by Ezh2 in order to increase at least one of the level and activity of Ezh2 or a gene positively regulated by Ezh2. Antisense oligonucleotides are DNA or RNA molecules that are complementary to some portion of a mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190, 931). The methods of the invention include the use of antisense oligonucleotide to diminish the amount of a molecule that causes a decrease at least one of the level and activity of Ezh2 or a gene positively regulated by Ezh2, thereby increasing at least one of the level and activity of Ezh2 or a gene positively regulated by Ezh2. Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

Similarly, the expression of a gene may be inhibited by the hybridization of an antisense molecule to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

Alternatively, inhibition of a gene expressing a protein that diminishes at least one of the level and activity of Ezh2 or a gene positively regulated by Ezh2 can be accomplished through the use of a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

Inhibitors

In various embodiments, the composition for generating an improved T cell of the invention comprises an inhibitor of a regulator of Ezh2 or an inhibitor of a gene negatively regulated by Ezh2. In one embodiment, the inhibitor of the invention decreases the amount of polypeptide, the amount of mRNA, the amount of activity, or a combination thereof of a regulator of Ezh2 or a gene negatively regulated by Ezh2. Genes negatively regulated by Ezh2 include, but are not limited to, genes listed in Table 3 which are not in bold. In one embodiment, a gene negatively regulated by Ezh2 is at least one of Id2, Eomes and Prdm1.

In one embodiment, regulators of Ezh2 signaling include, but are not limited to, PI3K, calcinurin, JMJD3, AKT and AP-1. In one embodiment, the invention provides a composition comprising at least one, at least two, at least three, at least four or more than four inhibitors of PI3K, calcinurin, JMJD3, AKT and AP-1 for use in a method of generating an improved T cell. Therefore, in one embodiment, the invention provides an improved T cell that has been contacted with at least one inhibitor of at least one of PI3K, calcinurin, JMJD3, AKT and AP-1. In one embodiment the improved T cell of the invention comprises a T cell that has been contacted with at least 1, at least 2, at least 3, at least 4, or more than 4 inhibitors of regulators of Ezh2. Exemplary inhibitors of calcinurin include, but are not limited to, CsA and Tacrolimus. Exemplary inhibitors of JMJD3 include, but are not limited to, GSK-J4 and 5-Carboxy-8-hydroxyquinoline. Exemplary inhibitors of AKT include, but are not limited to, MEK2206, SB203580, MK2206, SC79, AZD5363, LM22B-10, GDC-0068, GSK-690693, Afuersertib, AKT inhibitor VIII, A-443654, TIC10, Honokiol, Triciribine, A-674563, Prifosine, and Miltefosine. Exemplary inhibitors of AP-1 include, but are not limited to, SR11302, SP100030, c-JUN peptide, Tanshinone IIA (TanIIA), E3330, NNGH, Sulfaphenoazole, U0126 monoethanolate, IQ-1S, SM-7368, NIN-43, MEK inhibitor VII, TNAP inhibitor, FR180204, and APE1 inhibitor III. Exemplary inhibitors of PI3K include, but are not limited to, (S)-AR-TURMERONE, 4-O-METHYLHONOKIOL, 5-(9-ISOPROPYL-2-MORPHOLINO-9H-PURIN-6-YL)PYRIMIDIN-2-AMINE, A66, Arenobufagin, Bay80-6946, Benidipine Hydrochloride, BEX235, BKM120, BYL719, CAL-101, CH5132799, CUDC-907, GDC-0980, GSK-2126458, GSK-2334470, GSK-2636771, IPI-145, Ly-294002, PF-04691502 Dihydrate, Piceatanol, PKI-402, PP-121 and PX-866. Therefore, in one embodiment the improved T cell of the invention has been contacted with at least 1, at least 2, at least 3, at least 4 or all five types of inhibitors, including AKT inhibitors, PI3K inhibitors, AP-1 inhibitors, calcinurin inhibitors and JMJD3 inhibitors.

Other inhibitors that can potentially affect the phosphorylation of EZH2 include, but are not limited to, CDK1 inhibitors (e.g., R547, Dinaciclib, BMS-265246, JNJ-7706621, AZD5438, Alvocidib, SU9516, PHA-793887, P276-00, AT7519, PHA-7677491, Milciclib (PHA-848125), SNS-032, NU6027 and LDC000067), CDK4/6 inhibitors (Palbociclib and Everolimus), and DNA-PK inhibitors (e.g., Ly3023414, KU-57788, NU 7026, PIK-75, LTURM34, CC-115 and Compound 401).

Therefore, in one embodiment the improved T cell of the invention has been contacted with at least 1, at least 2, at least 3, at least 4, at least 5, at least 6, at least 7 or at least 8 types of inhibitors, including AKT inhibitors, PI3K inhibitors, AP-1 inhibitors, calcinurin inhibitors, JMJD3 inhibitors, CDK1 inhibitors, CDK4/6 inhibitors, and DNA-PK inhibitors.

It will be understood by one skilled in the art, based upon the disclosure provided herein, that a decrease in the level of a regulator of Ezh2 or a gene negatively regulated by Ezh2 encompasses the decrease in the expression, including transcription, translation, or both. The skilled artisan will also appreciate, once armed with the teachings of the present invention, that a decrease in the level of a regulator of Ezh2 or a gene negatively regulated by Ezh2 includes a decrease in at least one of the level and activity of a regulator of Ezh2 or a gene negatively regulated by Ezh2. Thus, decrease in at least one of the level and activity of a regulator of Ezh2 or a gene negatively regulated by Ezh2 includes, but is not limited to, decreasing the amount of polypeptide, and decreasing transcription, translation, or both, of a nucleic acid encoding a regulator of Ezh2 or a gene negatively regulated by Ezh2; and it also includes decreasing any activity of a regulator of Ezh2 or a gene negatively regulated by Ezh2 as well.

In one embodiment, the composition of the invention comprises an inhibitor of a regulator of Ezh2 or a gene negatively regulated by Ezh2. In one embodiment, the inhibitor is selected from the group consisting of a small interfering RNA (siRNA), a microRNA, an antisense nucleic acid, a ribozyme, an expression vector encoding a transdominant negative mutant, an intracellular antibody, a peptide and a small molecule.

One skilled in the art will appreciate, based on the disclosure provided herein, that one way to decrease the mRNA and/or protein levels of a regulator of Ezh2 or a gene negatively regulated by Ezh2 in a cell is by reducing or inhibiting expression of the nucleic acid encoding a regulator of Ezh2 or a gene negatively regulated by Ezh2. Thus, the protein level of a regulator of Ezh2 or a gene negatively regulated by Ezh2 in a cell can also be decreased using a molecule or compound that inhibits or reduces gene expression such as, for example, siRNA, an antisense molecule or a ribozyme. However, the invention should not be limited to these examples.

In one embodiment, siRNA is used to decrease the level of a regulator of Ezh2 or a gene negatively regulated by Ezh2. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19):306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, PA (2003); and Gregory J. Hannon, Ed., RNAi A Guide to Gene Silencing, Cold Spring Harbor Laboratory Press, Cold Spring Harbor, NY (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of the protein using RNAi technology.

In other related aspects, the invention includes an isolated nucleic acid encoding an inhibitor, wherein an inhibitor such as an siRNA or antisense molecule, inhibits a regulator of Ezh2 or a gene negatively regulated by Ezh2, a derivative thereof, a regulator thereof, or a downstream effector, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, N.Y.) and as described elsewhere herein. In another aspect of the invention, a regulator of Ezh2 or a gene negatively regulated by Ezh2, can be inhibited by way of inactivating and/or sequestering one or more of a regulator of Ezh2 or a gene negatively regulated by Ezh2. As such, inhibiting the effects of a regulator of Ezh2 or a gene negatively regulated by Ezh2 can be accomplished by using a transdominant negative mutant.

In another aspect, the invention includes a vector comprising a siRNA or antisense polynucleotide. Preferably, the siRNA or antisense polynucleotide is capable of inhibiting the expression of a regulator of Ezh2 or a gene negatively regulated by Ezh2. The incorporation of a desired polynucleotide into a vector and the choice of vectors is well-known in the art as described in, for example, Sambrook et al., supra.

The siRNA or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA or antisense polynucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

In one embodiment of the invention, an antisense nucleic acid sequence which is expressed by a plasmid vector is used to inhibit a regulator of Ezh2 or a gene negatively regulated by Ezh2. The antisense expressing vector is used to transfect a mammalian cell or the mammal itself, thereby causing reduced endogenous expression of a regulator of Ezh2 or a gene negatively regulated by Ezh2.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit a regulator of Ezh2 or a gene negatively regulated by Ezh2. Ribozymes useful for inhibiting the expression of a target molecule may be designed by incorporating target sequences into the basic ribozyme structure which are complementary, for example, to the mRNA sequence of a regulator of Ezh2 or a gene negatively regulated by Ezh2 of the present invention. Ribozymes targeting a regulator of Ezh2 or a gene negatively regulated by Ezh2 may be synthesized using commercially available reagents (Applied Biosystems, Inc., Foster City, CA) or they may be genetically expressed from DNA encoding them.

When the inhibitor of the invention is a small molecule, a small molecule antagonist may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

In another aspect of the invention, an antibody specific for a regulator of Ezh2 or a gene negatively regulated by Ezh2 (e.g., an antagonist to a regulator of Ezh2 or a gene negatively regulated by Ezh2) may be used. As will be understood by one skilled in the art, any antibody that can recognize and bind to an antigen of interest is useful in the present invention. Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, NY). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magnetic affinity cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, NY).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, NY) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the $F(ab')_2$ fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

Improved T Cells

In one embodiment, the invention provides an improved T cell for use in immunotherapy. Therefore, in various embodiments, the invention provides improved T cells and methods of generating the improved T cells of the invention. In one embodiment, the improved T cell of the invention is a CART cell, a TCR-transgenic T cell, or a TIL. In one embodiment, the improved T cell of the invention is a multipotent T memory stem cell ($T_{SCM}$). In one embodiment, the improved T cell of the invention is an induced multipotent T memory stem cell ($iT_{SCM}$). In one embodiment, the improved T cell of the invention has a decreased level of phosphorylated Ezh2 as compared to an unimproved T cell. In various embodiments, the level of phosphorylated Ezh2 may be decreased by at least 1.1 fold, 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 25 fold, 30 fold, 35 fold, 40 fold, 45 fold, 50 fold, 60 fold, 70 fold, 80 fold, 90 fold, 100 fold or greater than 100 fold as compared to an unimproved T cell.

In one embodiment, the improved T cell of the invention has increased H3K27me3 activity as compared to an unimproved T cell. In various embodiments, the level of H3K27me3 activity may be increased by at least 1.1 fold, 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 25 fold, 30 fold, 35 fold, 40 fold, 45 fold, 50 fold, 60 fold, 70 fold, 80 fold, 90 fold, 100 fold or greater than 100 fold as compared to an unimproved T cell.

In one embodiment, the improved T cell of the invention has increased Ezh2 signaling as compared to an unimproved T cell. In various embodiments, the level of Ezh2 signaling may be increased by at least 1.1 fold, 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 25 fold, 30 fold, 35 fold, 40 fold, 45 fold, 50 fold, 60 fold, 70 fold, 80 fold, 90 fold, 100 fold or greater than 100 fold as compared to an unimproved T cell.

In one embodiment, the improved T cell has been genetically modified to express an Akt insensitive Ezh2 protein. In one embodiment, the T cell is genetically modified to express Ezh2S21A. n one embodiment, the improved T cell is a T cell that has been contacted with at least one inhibitor of PI3K, calcinurin, JMJD3, AKT, AP-1, CDk1, CDK4/6, or DNA-PK or a combination thereof. In one embodiment, the T cell has been cultured with at least one inhibitor of PI3K, calcinurin, JMJD3, AKT, AP-1, CDk1, CDK4/6 or DNA-PK or a combination thereof for at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 48 hours, at least 72 hours or more than 72 hours. In one embodiment, the improved T cell is cultured with at least one inhibitor of PI3K, calcinurin, JMJD3, AKT, AP-1, CDk1, CDK4/6 or DNA-PK or a combination thereof. In one embodiment the T cell of the invention is cultured with at least 1, 2, 3, 4, 5, 6, 7, 8 or more than 8 inhibitors which inhibit at least one of PI3K, calcinurin, JMJD3, AKT, AP-1, CDk1, CDK4/6 or DNA-PK or a combination thereof.

Chimeric Antigen Receptor (CAR)

In one embodiment, the T cell of the invention comprises one or more cell receptor that has been genetically engineered. In one embodiment, a receptor is a T cell receptor (TCR). In one embodiment, a receptor is a chimeric antigen receptor (CAR), and the T cell of the invention is a CAR T cell. CAR T cells for use in the invention can be generated as described, for example, in U.S. Pat. No. 8,906,682. Therefore, in one embodiment, the invention provides a CART cell that has been cultured with at least one inhibitor of PI3K, calcinurin, JMJD3, AKT, AP-1, CDk1, CDK4/6 or DNA-PK or a combination thereof. In one embodiment the CART cell of the invention is cultured with at least 1, 2, 3, 4, 5, 6, 7, 8 or more than 8 inhibitors which inhibit at least one of PI3K, calcinurin, JMJD3, AKT, AP-1, CDk1, CDK4/6 or DNA-PK or a combination thereof.

Antigens

As contemplated herein, the improved T cells of the invention may target any antigen to elicit an immune response. In one embodiment, an antigen is a tumor antigen. Tumor antigens can be divided into two broad categories: shared tumor antigens; and unique tumor antigens. Shared antigens are expressed by many tumors, while unique tumor antigens can result from mutations induced through physical or chemical carcinogens, and are therefore expressed only by individual tumors.

In the context of the present invention, "tumor antigen" refer to antigens that are common to specific hyperproliferative disorders. In certain aspects, the hyperproliferative disorder antigens of the present invention are derived from cancers, including but not limited to, primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, glioblastoma, neuroblastoma, and the like. In one embodiment, the hyperproliferative disorder is an advanced B cell malignancy.

The type of tumor antigen referred to in the invention may be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

Malignant tumors express a number of proteins that can serve as target antigens for an immune attack. For example, in B cell lymphoma, the tumor-specific idiotype immunoglobulin constitutes a truly tumor-specific immunoglobulin antigen that is unique to the individual tumor. B cell differentiation antigens, such as CD19, CD20 and CD37, are other candidates for target antigens in B cell lymphoma. Some of these antigens (CEA, HER-2, CD19, CD20, idiotype) have been used as targets for passive immunotherapy with monoclonal antibodies with limited success.

The tumor antigen and the antigenic cancer epitopes thereof may be purified and isolated from natural sources such as from primary clinical isolates, cell lines and the like. The cancer peptides and their antigenic epitopes may also be obtained by chemical synthesis or by recombinant DNA techniques known in the arts. Techniques for chemical synthesis are described in Steward et al. (1969); Bodansky et al. (1976); Meienhofer (1983); and Schroder et al. (1965). Furthermore, as described in Renkvist et al. (2001), there are numerous antigens known in the art. Although analogs or artificially modified epitopes are not specifically described, a skilled artisan recognizes how to obtain or generate them by standard means in the art. Other antigens, identified by antibodies and as detected by the Serex technology (see Sahin et al. (1997) and Chen et al. (2000)), are identified in the database of the Ludwig Institute for Cancer Research.

In one embodiment, an antigen may be a viral antigen or a bacterial antigen. In one embodiment, the antigen is associated with an infectious organism. Viral antigens include, but are not limited to, HIV antigens, hepatitis antigens, CMV antigens, and EBV antigens.

Vectors

The present invention also provides vectors comprising a transgene encoding a EZH2S21A protein for use in generating improved T cells of the invention. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression of a nucleotide sequence encoding EZH2S21A is typically achieved by operably linking a nucleic acid encoding the EZH2S21A polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, N.Y.), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1a promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a EZH2S21A polypeptide or portions thereof, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In one embodiment, the vector comprises a suicide gene, where expression of the gene results in the death of the cell comprising the vector. For example, in some instances, prolonged expression of the EZH2S21A of the invention is not desirable. In one embodiment, inclusion of a suicide gene in the vector allows for finer control over EZH2S21A expression in a subject. In one embodiment, expression of the suicide gene is inducible, for example with the use of an inducible promoter regulating suicide gene expression.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, N.Y.).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another embodiment, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of T Cells

In one embodiment, the improved T cell can be autologous with respect to the recipient. In such an embodiment, a T cell may be isolated from a subject who is also to be the recipient and improved according to the methods of the invention prior to administration to the subject.

In an alternative embodiment, the improved T cells can be allogeneic, syngeneic or xenogeneic with respect to the recipient. In such an embodiment, a T cell may be isolated from a subject or obtained from a source and improved according to the methods of the invention prior to administration to the recipient, wherein the subject or source and the recipient are not the same.

Prior to expansion and genetic modification, the T cells to be improved according to the methods of the invention may be obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immune-adherence or flow cytometry that uses a cocktail of monoclonal antibodies directed to cell surface markers present on the cells negatively selected.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

Activation and Expansion of T Cells

In one embodiment, the T cells of the invention are improved prior to activation and expansion. For example, in one embodiment, a T cell of the invention is genetically modified prior to activation and expansion. In one embodiment, the T cells of the invention are improved during activation and expansion. For example, in one embodiment, a T cell of the invention is cultured in the presence of at least one inhibitor of a regulator of Ezh2 signaling during activation and/or expansion.

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents.

In one embodiment of the present invention, the mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

Methods of Treatment

In one embodiment, the present invention provides for compositions and methods for treating or preventing recurrence of cancer. Cancers that can be treated or prevented using the methods of the invention, include, but are not limited to, primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, glioblastoma, neuroblastoma, and the like. In one embodiment, the method comprises administering to a subject in need thereof a composition comprising an improved T cell of the invention.

The present invention also provides methods for inhibiting the proliferation of tumor cells, the methods comprising administering to a subject in need thereof a composition comprising an improved T cell of the invention. In certain embodiments, the improved T cell of the invention reduces the quantity, number, amount or percentage of cells and/or cancer cells by at least 5%, at least 10%, at least 15%, at least 20%, at least 25%, at least 30%, at least 40%, at least 50%, at least 65%, at least 75%, at least 85%, at least 95%, or at least 99% in a subject with or animal model for cancer relative to a negative control. In one embodiment, the subject is a human.

In one embodiment, the present invention provides for compositions and methods for treating or preventing a chronic infection. In various embodiments, a chronic infection may be HIV infection, hepatitis infection, CMV-infection, EBV infection, and the like. In certain embodiments, the improved T cell of the invention reduces the duration or severity of an infection by at least 5%, at least 10%, at least 15%, at least 20%, at least 25%, at least 30%, at least 40%, at least 50%, at least 65%, at least 75%, at least 85%, at least 95%, or at least 99% in a subject with or animal model for a chronic infection relative to a negative control. In one embodiment, the subject is a human.

In various embodiments, the improved T cells administered to the subject, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient. Wishing not to be bound by theory, the anti-tumor immunity response elicited by the improved T cells may be an active or a passive immune response.

In one embodiment, the composition comprising an improved T cell of the invention may be a type of vaccine for ex vivo immunization and/or in vivo therapy in a mammal. In one embodiment, the mammal is a human.

With respect to ex vivo immunization, at least one of the following occurs in vitro prior to administering the cell into a mammal: i) expansion of the cells, ii) introducing a nucleic acid to the cells or iii) cryopreservation of the cells.

Ex vivo procedures are well known in the art and are discussed more fully below. Briefly, in one embodiment, cells are isolated from a mammal (e.g., a human) and genetically modified (i.e., transduced or transfected in vitro) with at least one of a vector expressing Ezh2S21A and a CAR disclosed herein. In one embodiment, the cells are further contacted with at least one inhibitor of Akt mediated Ezh2 phosphorylation (e.g., at least one inhibitor of PI3K, calcinurin, JMJD3, AKT, AP-1, CDk1, CDK4/6 or DNA-PK or a combination thereof) The improved T cell is then administered to a mammalian recipient to provide a therapeutic benefit. The mammalian recipient may be a human and the improved T cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of cancer. Thus, the present invention provides methods for the treatment or prevention of cancer comprising administering to a subject in need thereof, a therapeutically effective amount of the improved T cells of the invention.

The improved T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one embodiment formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Wishing not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cyclophosphamide, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: The Phosphorylation State of Ezh2 Determines its Capacity to Maintain CD8+ Memory T Cells for Antitumor Immunity Ezh2 is the histone methyltransferase that specifically catalyzes H3K27me3 (Margueron and Reinberg, 2011, Nature, 469:343-349; Boyer et al., 2006, Nature, 441:349-353; Bantignies and Cavalli, 2006, Curr Opin Cell Biol, 18:275-283). Whether Ezh2 is crucial for establishing and maintaining memory properties in T cells, and if this Ezh2 activity might be modified during T cell response, have not previously been determined.

The results presented herein identify Ezh2 as an epigenetic regulator that is essential for the development and maintenance of memory T cells and associated antitumor immunity. Remarkably, the phosphorylation state of Ezh2 determines its capacity to regulate the generation and maintenance of memory T cells. Akt activation causes phosphorylation of Ezh2, leading to the dissociation of Ezh2 from the promoter regions of TFs Id3, Id2, Prdm1 (which encodes Blimp-1) and Eomes, enhanced effector differentiation at an expense of memory T cells. Thus, the phosphorylation state of Ezh2 determines its capacity to maintain CD8+ T cell memory for antitumor immunity.

The materials and methods are now described

Mice

C57BL/6 (B6, Thy1.2$^+$), and transgenic Pm el-1 (B6.Cg-Thy1$^a$/Cy Tg(TcraTcrb)8Rest/J, Thy1.1$^+$) mice were purchased from The Jackson Laboratories. Ezh2 was deleted in gp100-specific CD8$^+$ T cell receptor-transgenic Pmel-1 cells by backcrossing Ezh2$^{fl/fl}$ CD4-Cre B6 mice to Pmel-1 mice to produce T cell-specific Ezh2-knockout Pmel-1 mice (Ezh2$^{-/-}$ Pmel-1).

Cell Preparation and Culture

Splenic and LN CD44loCD8+ $T_N$ cells were prepared as previously described (Zhang et al., 2002, J Immunol, 169: 7111-7118; Zhang et al., 2005, Nat Med, 11:1299-1305). The purity was usually 90-95%. CD8+ T cell cultures were set up as previously described (He et al., 2013, Blood, 122:4119-4128; Tong et al., 2014, J Immunol, 192:5012-5022). In brief, CD44loCD8+ naive T cells (were cultured in the presence of anti-CD3 (2 µg/ml) and anti-CD28 (2.0 µg/ml) Abs together with recombinant human IL-2 (10 ng/ml; R&D Systems). In vivo sorted T cells and cultured T cells were restimulated with anti-CD3 Ab (1 µg/ml; BioLegend) or human gp100 (10$^{-6}$ M) for 5 hours before intracellular staining. Bone marrow-derived dendritic cells (DCs) were generated as previously described (Zhang et al., 2005, Nat Med, 11:1299-1305). For TAT-Cre experiments, 10$^6$ purified CD8+ T cells or splenocytes were incubated in 100 μL serum-free RPMI containing 90 to 100 μg/mL TAT-Cre fusion protein for 16 hours at 37° C. After extensive washing, treated cells were kept in vitro culture for another 5 days.

Retroviral Construction and T Cell Infection

The MigR1 retroviral vector system was described previously (Tong et al., 2014, J Immunol, 192:5012-5022; Pear et al., 1998, Blood, 92:3780-3792). Ezh2, Ezh2 mutants, and Id3 cDNA was cloned into Mig-R1 (GFP) vector. For retroviral infection, CD8+ T cells were prestimulated with anti-CD3/CD28 Ab for 24 hours, and then the retrovirus supernatant was added in the presence of 8 μg/ml polybrene (Sigma). Cells were spinoculated at 3000 rpm, 32° C. for 3 hours. The same retroviral infection procedure was repeated 24 hours later (Tong et al., 2014, J Immunol, 192:5012-5022).

Adoptive Cell Transfer, Infection and Tumor Challenge

Pmel-1 T cells ($1 \times 10^4$ to $1 \times 10^6$) were transferred into sublethally irradiated B6 mice (5.0 Gy). IL-2 (100,000 IU) was administered intraperitoneally twice a day, and BM-derived DCs which have been pulsed with gp100 (10 μg) were transferred via tail vein, for constitutively three days after adoptive transfer. C57BL/6 mice were injected subcutaneously with $5 \times 10^5$ B16 melanoma cells. In some experiments, $Ezh2^{fl/fl}$ mice were intravenously received VVA-gp100 or VVA-OVA.

Counting of Adoptively Transferred Cells

Mice were euthanized after infection. Samples were enriched for mononuclear cells or CD8+ T cells (MACS positive selection kit), and cells were counted by trypan blue exclusion. The frequency of transferred T cells was determined by measurement of the expression of CD8 and Thy-1.1 by flow cytometry. The absolute number of Pmel-1 cells was calculated by multiplication of the total cell count with the percentage of CD8+ Thy-1.1.

RNAseq Analysis

RNA sequencing was carried out at the sequencing core at University of Michigan Sequencing Core (Ann Arbor, Michigan). Transcriptome analysis was performed on RNA isolated from fresh naïve and cultured CD8+ T cells. Briefly, total RNA was isolated from T cells using an RNAeasy kit (QIAGEN) and RNA-seq libraries were prepared using SureSelect RNA Library Preparation kits (Agilent Technologies) according to the manufacturers' instructions. Samples were run on a HiSeq 2000 sequencing system (Illumina), and at least $37.5 \times 10^6$ single-end reads were obtained per sample. Expression was evaluated by determining the fragment per kilobase per million reads values. Using one-way ANOVA analysis, transcripts with $p<0.01$ and $q<0.01$ were selected for comparing paired groups and at least a 1.5-fold difference from the means for the paired groups. RNAseq data were deposited in the NCBI's Gene Expression Omnibus database (accession no. GSE76755).

Reverse Transcription Polymerase Chain Reaction (RT-PCR)

RNA was isolated with an RNeasy Mini kit (Qiagen) and cDNA was generated by reverse transcription (Applied Biosystems). Real-time RT-PCR was performed with a SYBR green PCR mix (ABI Biosystems) in the Realplex Eppendorf Real-time PCR instrument (Eppendorf AG). Gene expression levels were calculated relative to the 18s gene. Data were collected and quantitatively analyzed on a Realplex sequence detection system (Eppendorf AG), and Applied Biosystems StepOne Plus Real-time PCR systems (Applied Biosystems).

ChIP

A Millipore ChIP kit and Diagenode ChIP kit was used for ChIP assay as described by the manufacturer. DNA-protein complexes were crosslinked with formaldehyde at a final concentration of 1%. Sonicated extracts were precleared and incubated with Abs specific to Ezh2, H3K27me3, or non-specific anti-IgG. The immunoprecipitated DNA was quantified by real-time quantitative PCR.

Western Blot Analysis

Proteins were separated by 4-20% SDS-PAGE, followed by standard immunoblot analysis. Anti-Ezh2 (11), anti-β-actin (C4) and anti-Id3 (B72-1) Abs were purchased from BD Bioscience. Anti-Suz12 (D39F6), anti-Id2 (D39E8m), anti-Eomes, anti-H3K4me3 (C42D8), anti-H3K9me3 (D4W1U), anti-H3K36me3 (D5A7), anti-Akt (C67E7), anti-phospho-Akt (Thr308, D25E6), anti-phospho-Akt (Ser473, D9E), HRP-linked anti-rabbit IgG, HRP-linked anti-mouse IgG Abs were purchased from Cell Signaling Technology. Anti-Eed (AA19) and anti-M11 (9-12) Abs were purchased from Millipore. Anti-Blimp1 (6D3), anti-T-bet (4B10) and anti-H3K27me3 (6002) Abs were purchased from eBioscience, Santa Cruz Technology and Abcam, respectively.

Flow Cytometric Analysis and Cell Lines

The Abs used for flow cytometric analyses were purchased from eBioscience, BioLegend, or BD Biosciences. Flow cytometric analyses were performed with FACS LSRII (BD Biosciences) as described (Zhang et al., 2005, Nat Med, 11:1299-1305; Zhang et al., 2002, J Immunol, 169:7111-7118). B16 mouse melanoma cell line was from American Type Culture Collection.

Statistical Analyses

Unless otherwise specified, statistical tests were performed using unpaired two-tailed Student's t-test. Where necessary, the Shapiro-Wilk test was used to test for normality of the underlying sample distribution. No blinding was done, as objective quantitative assays such as flow cytometry, were used. Experimental sample sizes were chosen using power calculations with preliminary experiments and/or were based on previously described variability in similar experiments (Overwijk et al., 2003, J Exp Med, 198:569-580; He et al., 2012, Blood, 119:1274-1282; Gattinoni et al., 2009, Nat Med, 15:808-813; Zhang et al., 2002, The Journal of clinical investigation, 109:1335-1344; Zhang et al., 2005, Nat Med, 11:1299-1305; Zhang et al., 2011, Blood 117, 299-308). Samples that had undergone technical failure during processing were excluded from analyses. Where relevant, recipient mice were randomized before adoptive transfer. p values of 0.05 or less were considered significant.

The results are now described

Ezh2 is Essential to CD8+ T Cell Memory Recall Response and Antitumor Immunity

To evaluate the impact of Ezh2 in memory CD8+ T cell response against persistently expressed antigen, Ezh2 was deleted in melanoma-associated antigen gp100-specific CD8+ T cell receptor (TCR)-transgenic Pmel-1 cells by backcrossing Ezh2fl/fl CD4-Cre B6 mice21 to Pmel-1 mice (Overwijk et al., 2003, J Exp Med, 198:569-580, which gave rise to T cell-specific Ezh2-knockout Pmel-1 mice ($Ezh2^{-/-}$ Pmel-1). Transfer of wild-type (WT) but not $Ezh2^{-/-}$ Pmel-1 cells repressed the growth of pre-established B16 melanoma in sublethally irradiated lymphodepleted mice (FIG. 1A). In separate experiments using lymphopenic recipients without B16 tumor, the frequency and number of WT and $Ezh2^{-/-}$ Pmel-1 cells in the spleen was similar 4 days after transfer and immunization, while $Ezh2^{-/-}$ Pmel-1 cell numbers were greatly decreased 7 days and 35 days after transfer (FIG.

Figures 2A, 2B:
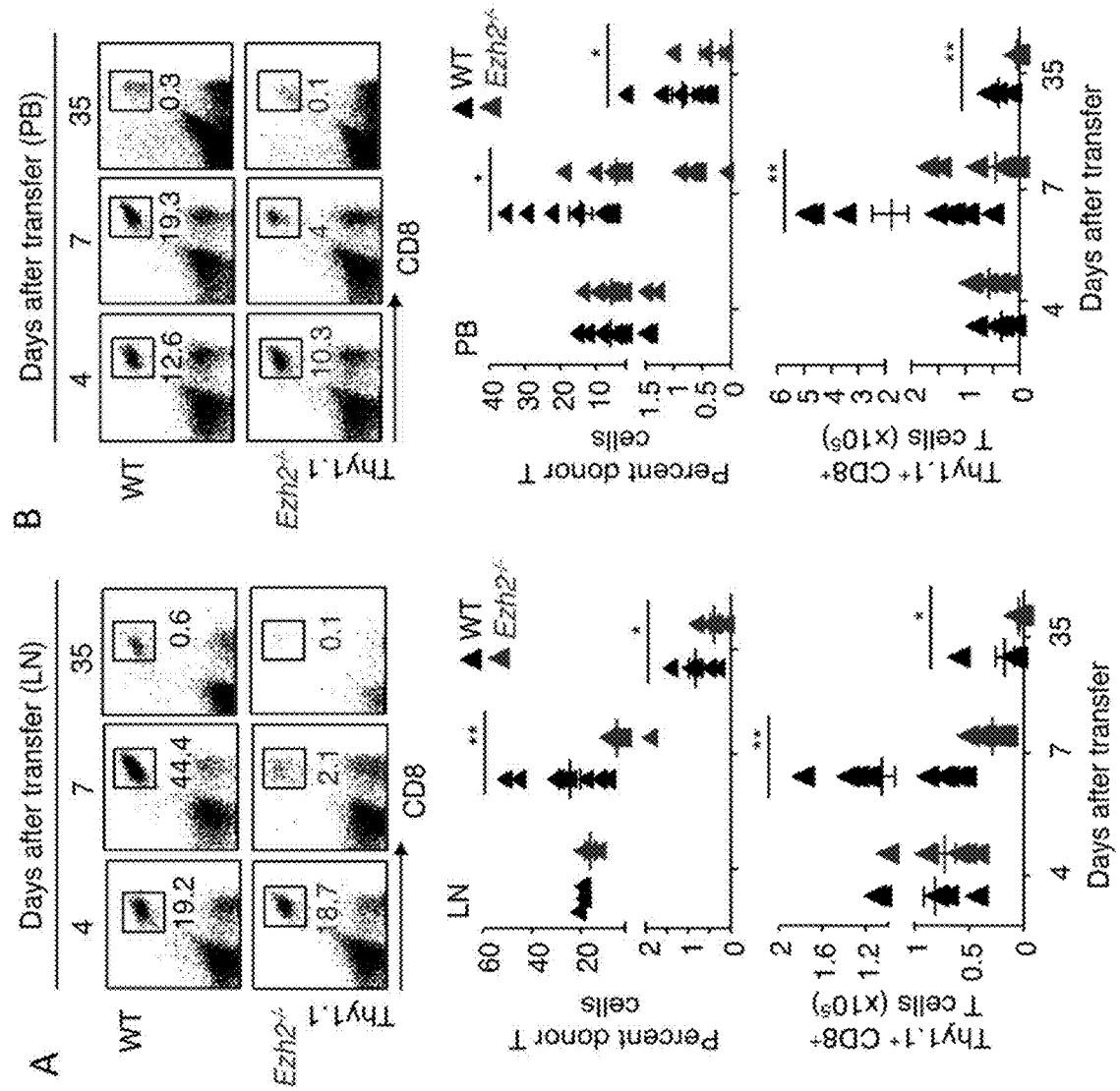
FIG. 2A through FIG. 2B, depicts exemplary experimental results demonstrating that Ezh2 promotes CD8$^+$ T cell anti-tumor immunity and memory formation. WT and Ezh2$^{-/-}$ naïve (T$_N$) Pmel-1 cells (1×10$^6$, Thy1.1$^+$) were transferred into sublethally irradiated (5 Gy) B6 mice (Thy1.2$^+$), followed by immunization with IL-2 (1×10$^5$ IU/injection, i.p., twice a day) and gp100-pulsed DCs (gp100/DCs, 1×10$^6$) for 3 days.

1B). The discrepancy was not due to differences in organ tropism, as fewer Ezh2$^{-/-}$ Pmel-1 cells were detected in both peripheral blood (PB) and lymph node (LN) (FIG. 2). Further, although Ezh2 deficiency did not affect the capacity of Pmel-1 cells to produce IFN-γ during the effector phase (day 7), it caused a significant reduction of IFN-γ-producing cells by 35 days after transfer (FIG. 1C), suggesting an impaired formation of memory T cells.

To test the impact of Ezh2 deficiency on memory recall upon antigen rechallenge, equal numbers of WT and Ezh2$^{-/-}$ memory Pmel-1 cells were transferred, which were recovered from primary recipients 42 days after gp100-immunization, into secondary recipients. Seven days after gp100-rechallenge, Ezh2$^{-/-}$ memory Pmel-1 cells produced about 2- and 6-fold fewer total CD8+ T cells and IFN-γ-secreting effectors, respectively, compared to their WT counterparts (FIG. 1D and FIG. 1E). In addition, when donor T cells derived from these secondary recipients were cultured with gp100 for 5 days, Ezh2$^{-/-}$ memory progeny were unable to expand compared to their WT counterparts (FIG. 1F). This suggests that decreased persistence of activated Ezh2-/- Pmel-1 cells may result from their impaired memory potential.

Figures 3A, 3B, 3C, 3D, 3E, 3F:
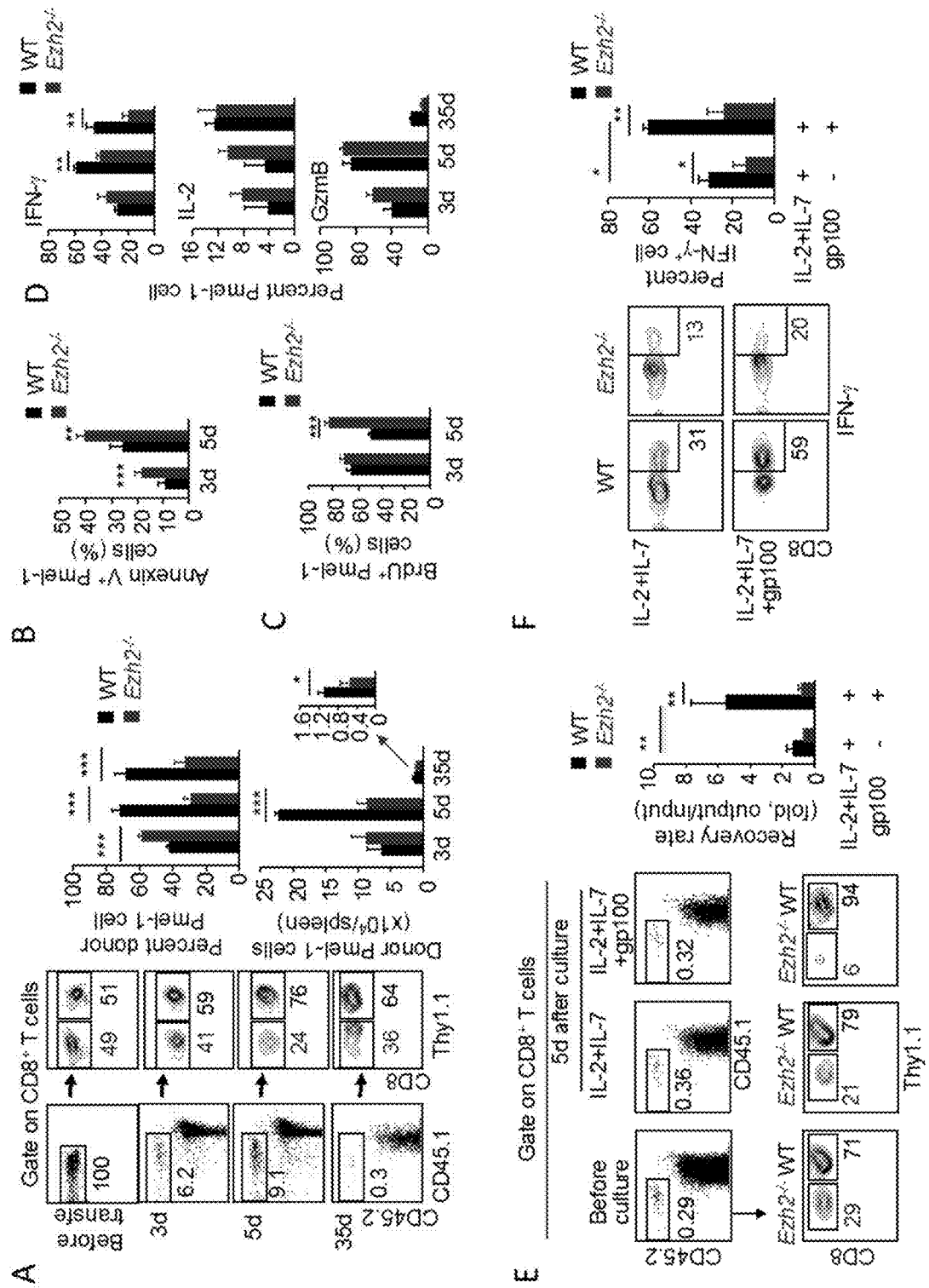
FIG. 3A through FIG. 3F, depicts exemplary experimental results demonstrating that Ezh2 is required for CD8+ T cells to form memory functionally intact memory cells in lymphoreplete mice infected with VVA-gp100 infection WT naïve Pmel-1 cells (Thy1.1$^+$ CD45.2$^+$, 5×10$^4$) and Ezh2−/− naïve Pmel-1 cells (Thy1.1$^-$ CD45.2$^+$, 5×10$^4$) were co-transferred into B6/SJL (CD45.1$^+$) mice, followed by infection with VVA-gp100 (1.25×10$^6$ PFU). Donor cells were recovered from the spleen at the indicated time points after infection.

To enable more general interpretation of these experimental findings, lymphoreplete mice were used for validation. Equal numbers of congenically labeled WT (CD45.2+, Thy1.1+) and Ezh2-/- (CD45.2+, Thy1.2+) Pmel-1 cells were co-injected into non-irradiated B6/SJL mice (CD45.1+, Thy1.2+), followed by infection with vaccinia virus encoding gp100 (VVA-gp100). This also allowed the testing of a cell-autonomous effect of Ezh2 deficiency in lymphoreplete hosts. Again, although loss of Ezh2 did not impair the initial proliferation in the spleen 3 d after immunization, it caused approximately 2-fold reduction in number by day 5 and day 35 (FIG. 3A). Impaired expansion of Ezh2-/- Pmel-1 cells in vivo was not the result of decreased proliferation but rather it was dependent on increased apoptosis (FIG. 3B and FIG. 3C). Loss of Ezh2 caused a significant decrease in the frequency of Pmel-1 producing high levels of IFN-γ day 5 and day 35 after immunization, without significant reduction of IL-2 and granzyme B (GzmB) (FIG. 3D). Ex vivo culture of day 35-memory T cells revealed that Ezh2 deficiency resulted in 5-fold less expansion of Pmel-1 cells upon rechallenging with gp100 (FIG. 3E). Furthermore, while gp100-restimulation induced a 2-fold higher frequency of IFN-γ-producing Pmel-1 cells in WT day 35-memory T cells compared to non-stimulation controls, it did not significantly increase IFN-γ production by Ezh2-/- memory T cells (FIG. 3F). Thus, Ezh2 is crucial for memory formation and function under either lymphopenic or lymphoreplete conditions.

Ezh2 Helps Memory T Cell Formation Throughout all Three Phases of the T Cell Responses.

Figures 4A, 4B, 4C, 4D, 4E, 4F, 4G, 4H, 4I:
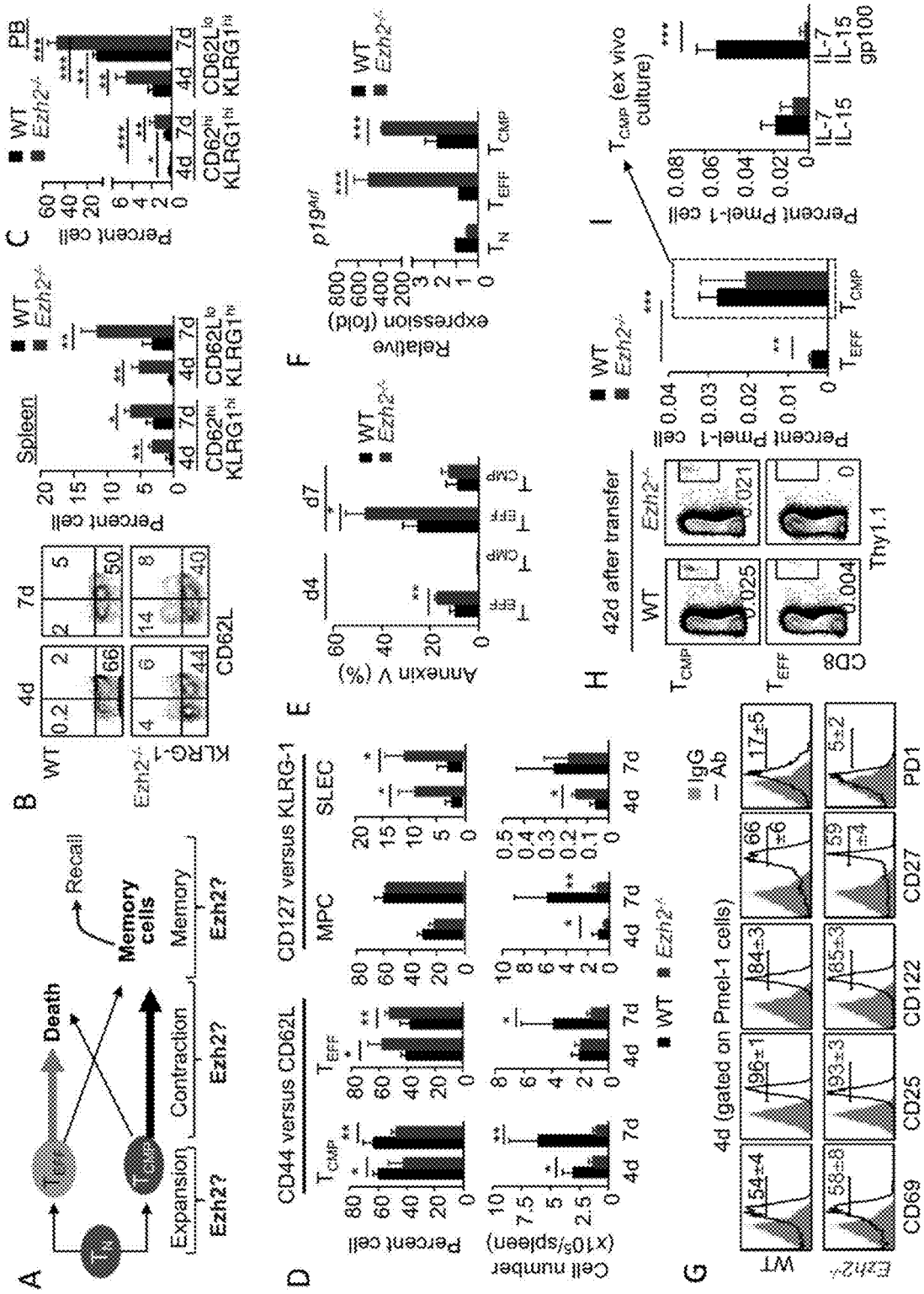
FIG. 4A through FIG. 4I, depicts exemplary experimental results demonstrating that Ezh2 helps establish memory properties in activated CD8$^+$ T cells early during expansion.

A typical T cell response contains three characteristic phases: clonal expansion, apoptotic contraction and memory phase (FIG. 4A). Three different strategies were used to determine at which T cell response phase(s) Ezh2 is required to support memory T cell formation and function. During the initial phase, antigen-activated CD8+ T cells generate two subsets of precursor memory T cells: CD44$^{hi}$CD62L$^{hi}$ central memory precursor CD8+ T cells (T$_{CMP}$) and CD44$^{hi}$CD62L$^{lo}$ T$_{EFF}$. T$_{CMP}$ are less differentiated and have greater ability than T$_{EFF}$ to replicate and generate memory cells (Fearon, 2007, Adv Immunol, 96:103-139; Kaech and Cui, 2012, Nat Rev Immunol, 12:749-761; Paley et al., 2012, Science, 338:1220-1225; Restifo et al., 2012, Nat Rev Immunol, 12:269-281; Jensen and Riddell, 2014, Immunol Rev, 257:127-144). T$_{CMP}$ and T$_{EFF}$ from WT and Ezh2-/- Pmel-1 cell recipients were characterized 4 days and 7 days after transfer into lymphodepleted mice. CD8+ T cells expressing high levels of KLRG1 (KLRG1$^{hi}$) represent a terminally differentiated proliferating cells (Kaech and Cui, 2012, Nat Rev Immunol, 12:749-761). Ezh2 deficiency caused significantly higher frequency of KLRG-1-expressing CD62L$^{hi}$- and CD62L$^{lo}$-T cells, which occurred as early as day 4 after immunization and further increased by day 7 (FIG. 4B). This difference was even greater in peripheral blood (PB) (FIG. 4C). The absence of Ezh2 caused a skewed differentiation of activated CD8+ T cells towards T$_{EFF}$, as evidenced by increased fraction of T$_{EFF}$ and a corresponding reduction of both T$_{CMP}$ frequency and numbers throughout the expansion phase (FIG. 4D). Similar results were observed when responding cells were segregated into memory potential cells (MPC) and short-lived effector cells (SLECs) on the basis of KLRG-1 and IL-7Rα expression, featured by significantly increased percentage and number of SLECs at day 4 (FIG. 4D). Notably, while loss of Ezh2 did not markedly affect the survival of TCMP both at 4 d and 7 d, it caused markedly enhanced apoptosis of T$_{EFF}$ early during expansion (day 4) (FIG. 4E). Without being bound by a particular theory, since KLRG-1 normally is expressed on the surface of CD62L+CD8+ T cells (Kaech and Cui, 2012, Nat Rev Immunol, 12:749-761; Joshi et al., 2007, Immunity, 27:670-684), ectopic expression of KLRG-1 on the surface of CD62L+CD8+ T cells probably indicates their precocious differentiation. Thus, Ezh2 is important for preserving the pool size of T$_{CMP}$, primarily through a mechanism of restraining differentiation into SLECs. This was supported by the observation that both Ezh2-/-T$_{CMP}$ and T$_{EFF}$ expressed 370- and 500-fold more transcripts, respectively, of the senescence gene p19$^{Arf}$ than their WT counterparts (FIG. 4F).

Figures 5A, 5B, 5C:
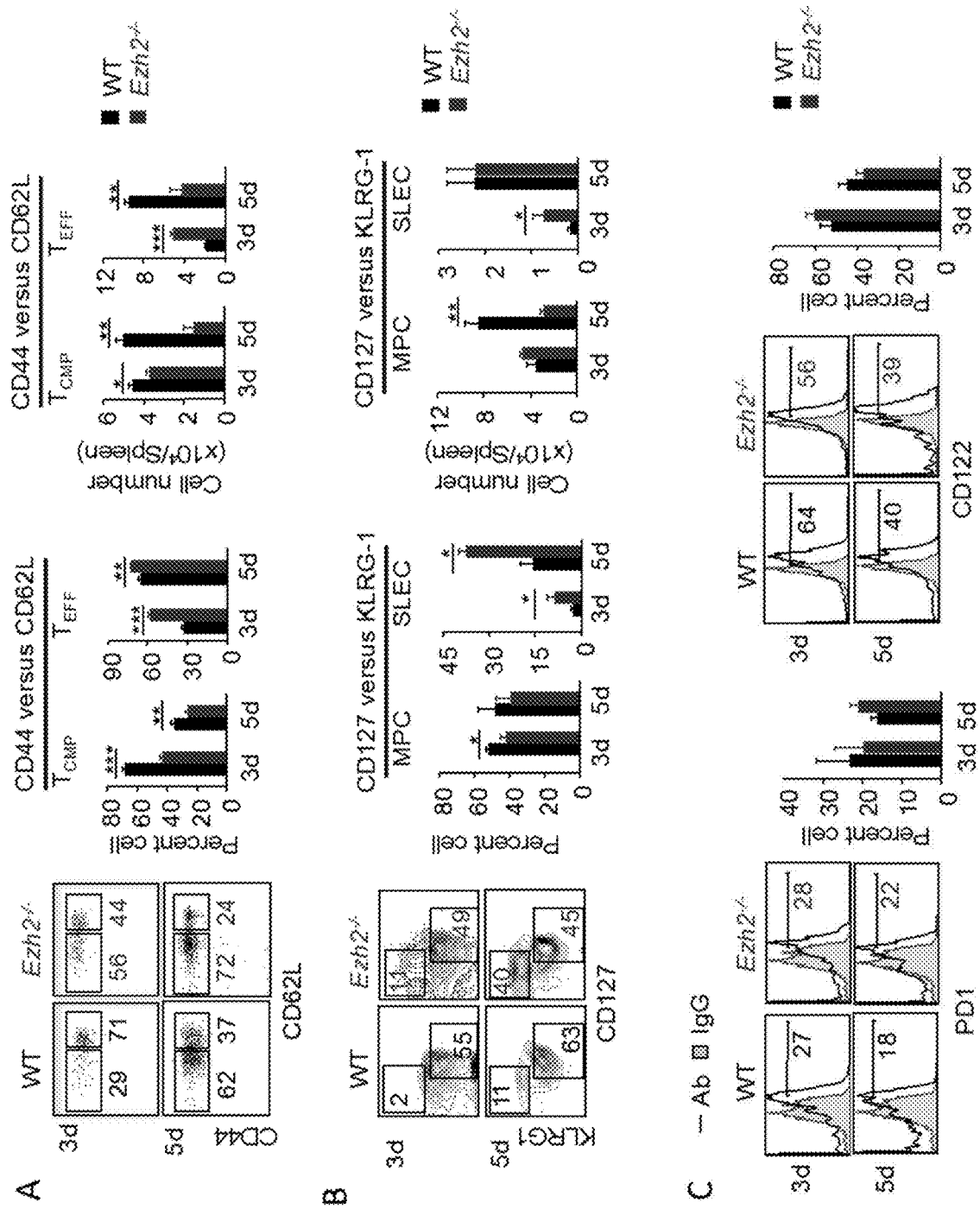
FIG. 5A through FIG. 5C, depicts exemplary experimental results demonstrating that Ezh2 inhibition promotes terminal differentiation at the expense of T$_{CMP}$. WT naïve Pmel-1 cells (Thy1.1$^+$CD45.2$^+$, 5×10$^4$) and Ezh2$^{-/-}$ naïve Pmel-1 cells (Thy1.1$^{-/-}$CD45.2$^+$, 5×10$^4$) were co-transferred into B6/SJL (CD45.1$^+$) mice, followed by infection with VVA-gp100 (1.25×10$^6$ PFU). Donor T cells were recovered from the spleen at day 3 and day 5 after infection to measure the presence of different subsets of CD8$^+$ T cells.
Figures 6A, 6B, 6C, 6D, 6E, 6F:
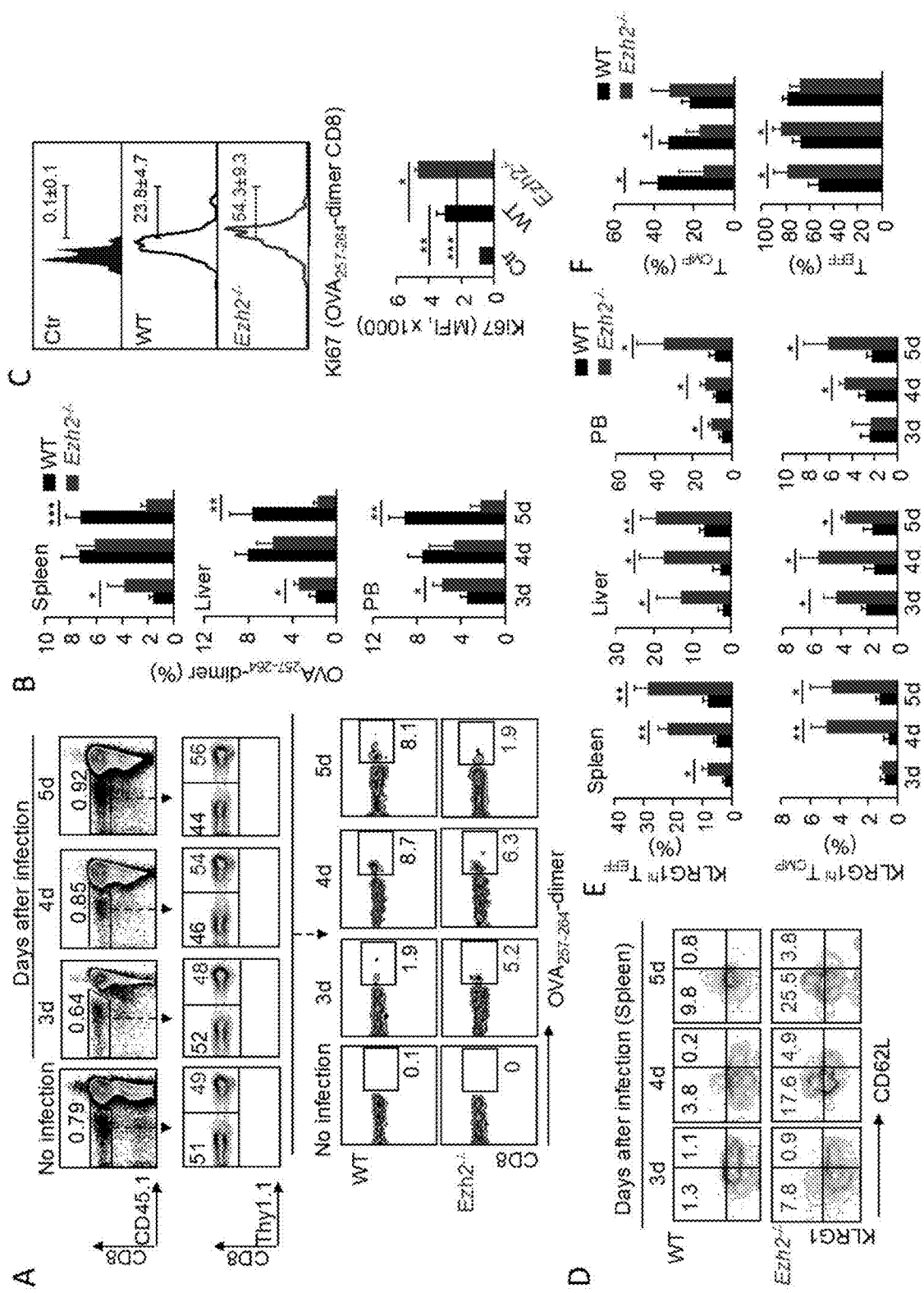
FIG. 6A through FIG. 6F, depicts exemplary experimental results demonstrating Ezh2 deficiency leads to preferential loss of endogenous memory precursors. Equal amounts of WT (Thy1.1$^+$CD45.2$^+$) and Ezh2$^{-/-}$ (Thy1.1$^-$CD45.2$^+$) splenocytes (2×10$^7$) were co-transferred into lymphoreplete B6/SJL mice (Thy1.1$^-$CD45.1$^+$, n=3 for each group), followed by infection with VVA-OVA. At indicated days after infection, donor T cells were isolated, stained with the dimer binding to OT-I specific CD8$^+$ T cells.

Notably, Ezh2-deficiency-mediated change in surface phenotype was largely associated with T cell differentiation rather than activation and exhaustion markers (e.g., CD69, CD25, CD122, and PD-1) in these lymphodepleted hosts (FIG. 4G). Using lymphoreplete mice immunized by VVA-gp100, the impact of Ezh2 deficiency on reducing T$_{CMP}$ and MPCs and increasing SLECs, without changing the expression of other surface markers such as CD122 and PD-1, was validated (FIG. 5). To stringently examine the cell autonomous effect of Ezh2 on endogenous CD8+ T cell responses, equal amounts of WT (Thy1.1+CD45.2+) and Ezh2-/- (Thy1.1-CD45.2+) splenocytes were transfected into lymphoreplete B6/SJL mice (Thy1.1-CD45.1+), followed by infection with vaccinia virus encoding OVA (VVA-OVA). As compared to WT CD8+ T cells, Ezh2-/-CD8+ T cells produced 1.5- to 2-fold more OVA$_{257-264}$-specific T cells 3 days after infection, maintained at day 4, and dramatically declined by day 5 (FIG. 6A and FIG. 6B). Notably, the increase of OVA$_{257-264}$-specific Ezh2-/- CD8 T cells 3 days after infection was associated significantly enhanced proliferation rates (FIG. 6C), increases of KLRG1$^{hi}$ cells (FIG. 6C and FIG. 6D) and selectively decreased ratio of T$_{CMP}$ versus T$_{EFF}$ (FIG. 6F). Thus, loss of Ezh2 leads to an earlier occurrence of the peak of T cell response, exaggerated terminal differentiation and preferential loss of memory precursors.

Figures 7A, 7B:
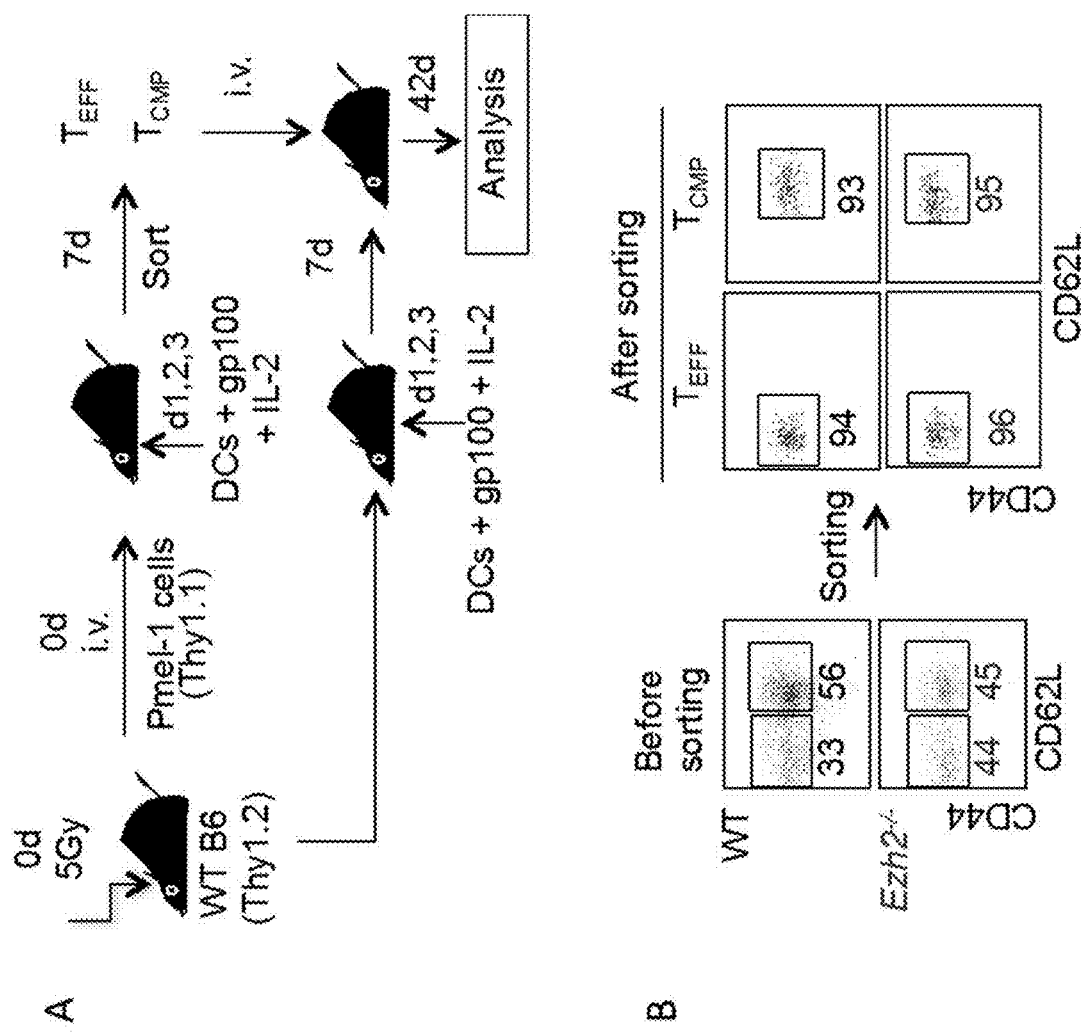
FIG. 7A through FIG. 7B, depicts exemplary experimental results demonstrating the purification and transfer of precursor memory T cells.

The second phase is featured by massive apoptosis of effector cells and the transition of memory precursors into mature memory cells. To evaluate the long-term effect Ezh2 deficiency on this transition, T$_{CMP}$ and T$_{EFF}$ were purified from primary lymphodepleted recipients 7 days after transfer of Pmel-1 cells and immunization, and then separately transferred them into gp100 immunization-matched secondary recipients (FIG. 7). WT $T_{CMP}$ produced 6-fold more memory cells than WT $T_{EFF}$ 42 d after transfer (FIG. 2h), confirming that $T_{CMP}$ have greater ability than $T_{EFF}$ to produce memory cells. 3, 32 Ezh2−/− $T_{EFF}$ failed to produce detectable memory T cells, suggesting the importance of Ezh2 for $T_{EFF}$ transition to be memory cells. Interestingly, Ezh2−/− $T_{CMP}$ produced similar percentages of memory cells like WT $T_{CMP}$ (FIG. 4H), but their progenies were incapable of expanding upon gp100 rechallenge, unlike those of WT $T_{CMP}$ (FIG. 2I). Thus Ezh2 is dispensable for the homeostatic survival of $T_{CMP}$ during contraction phase, but is important for the transition of both $T_{CMP}$ and $T_{EFF}$ into functionally mature memory T cells.

Figures 8A, 8B, 8C, 8D, 8E:
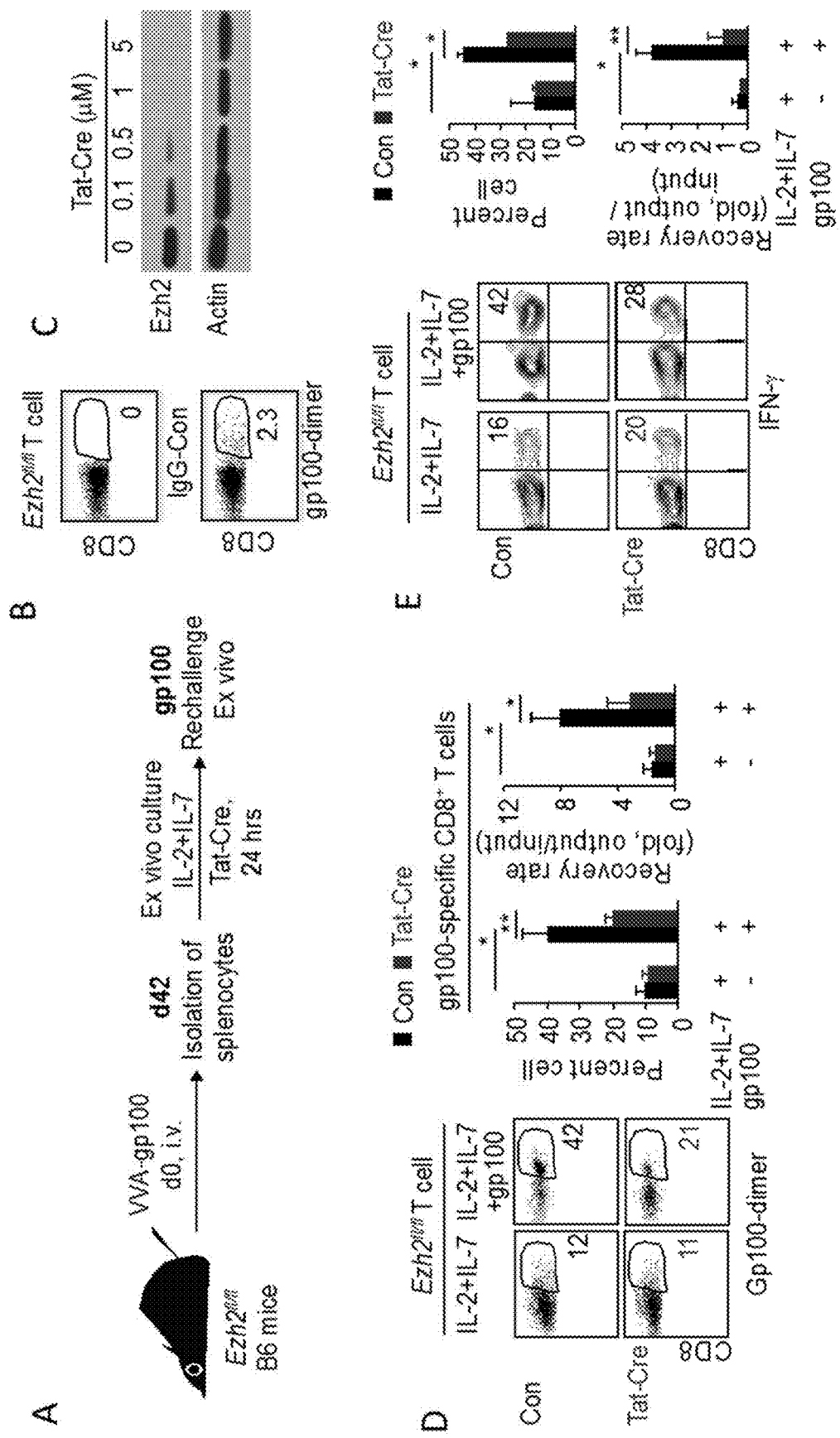
FIG. 8A through FIG. 8E, depicts exemplary experimental results demonstrating that selective deletion of Ezh2 in mature memory CD8$^+$ T cells impairs their memory recall responses. Ezh2$^{fl/fl}$ B6 mice were infected with VVA-gp100 (1.25×10$^6$ PFU). Splenocytes were recovered at 42 days after infection, cultured in the presence of IL-7 (5 ng/ml)+IL-15 (5 ng/ml) and treated with or without TAT-Cre for 24 hours. After extensive wash with PBS, cells were re-cultured ex vivo for additional 5 days in the presence of IL-2+IL-7 with or without gp100. H2db-gp100 specific dimer was used to stain gp100-specific CD8$^+$ T cells.

It is possible that increased apoptosis of Ezh2−/− T cells during the effector phase might result in long-term consequences on recall response capacity during the final memory phase. To test this concept, lymphoreplete Ezh2$^{fl/fl}$ mice were immunized with VVA-gp100 (FIG. 8A). Forty-two days later when gp100-specific memory CD8+ T cells were formed (FIG. 8B), splenocytes were isolated from these mice and treated them with TAT-Cre to delete Ezh2 (FIG. 8C), followed by culturing them ex vivo for 5 days, with or without gp100 addition. Deletion of Ezh2 by TAT-Cre dramatically decreased the capacity of these Ezh2$^{fl/fl}$ memory CD8+ T cells to expand and produce IFN-γ upon gp100 rechallenge (FIG. 8D and FIG. 8E). Collectively, Ezh2 is important for establishing memory properties in proliferating T cells during the initial expansion phase, helps the transition of memory cells from precursors to mature cells, and maintains the acquired recall capacity of both replicative and effector responses in developed memory T cells.

Figures 9A, 9B, 9C, 9D, 9E:
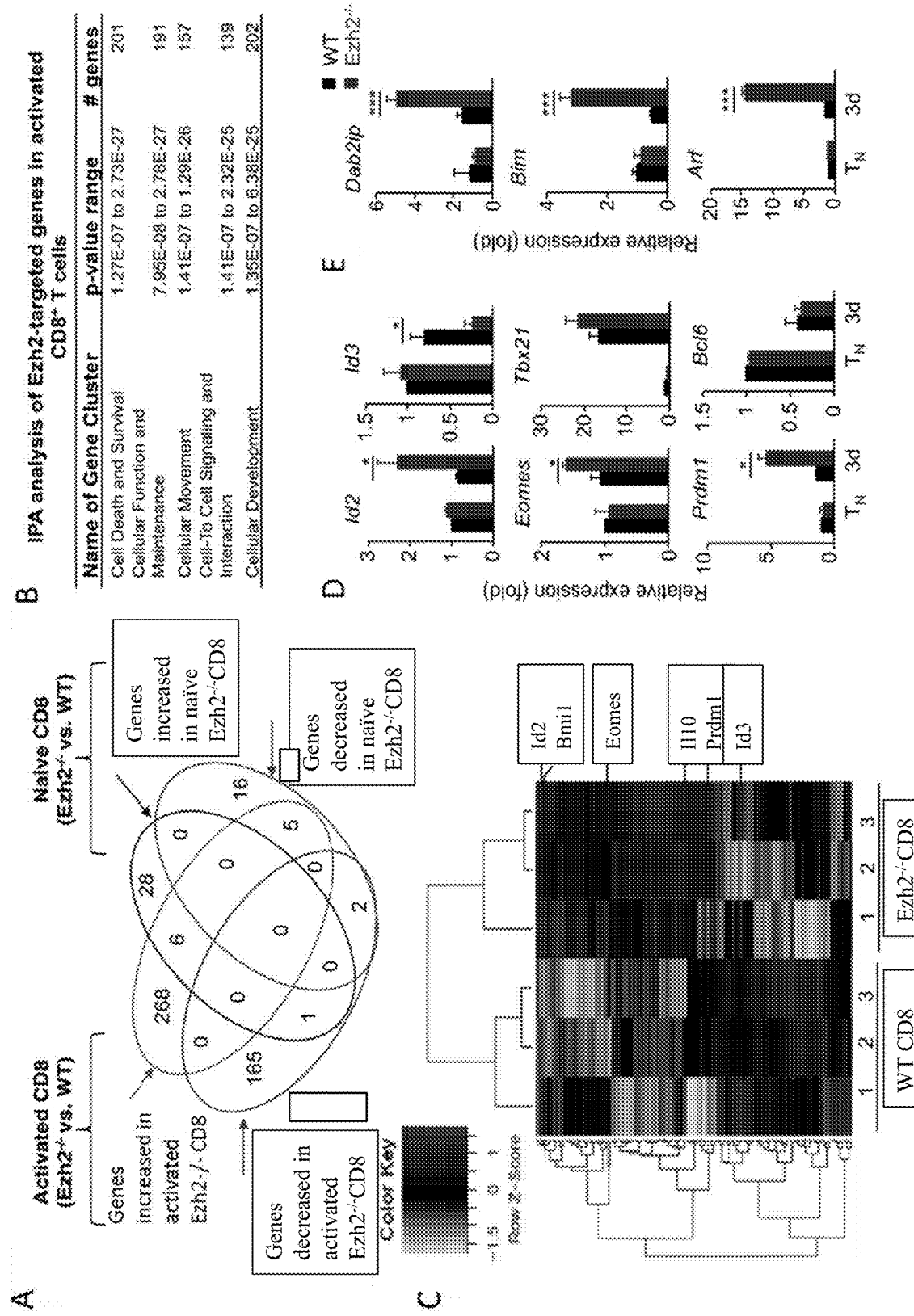
FIG. 9A through FIG. 9E, depicts exemplary experimental results demonstrating Ezh2 orchestrates the expression of genes critical for effector differentiation and memory formation. For FIG. 9A through FIG. 9C, WT and Ezh2$^{-/-}$ Pmel-1 cells were cultured in the presence of anti-CD3/CD28 antibodies (Abs) and IL-2 for 3 days. Cells were collected to extract RNA for sequencing. Using one-way ANOVA analysis, transcripts with p<0.01 and q<0.01 were selected for comparing paired groups and at least a 1.5-fold difference from the means for the paired groups.
Figures 10A, 10B, 10C, 10D:
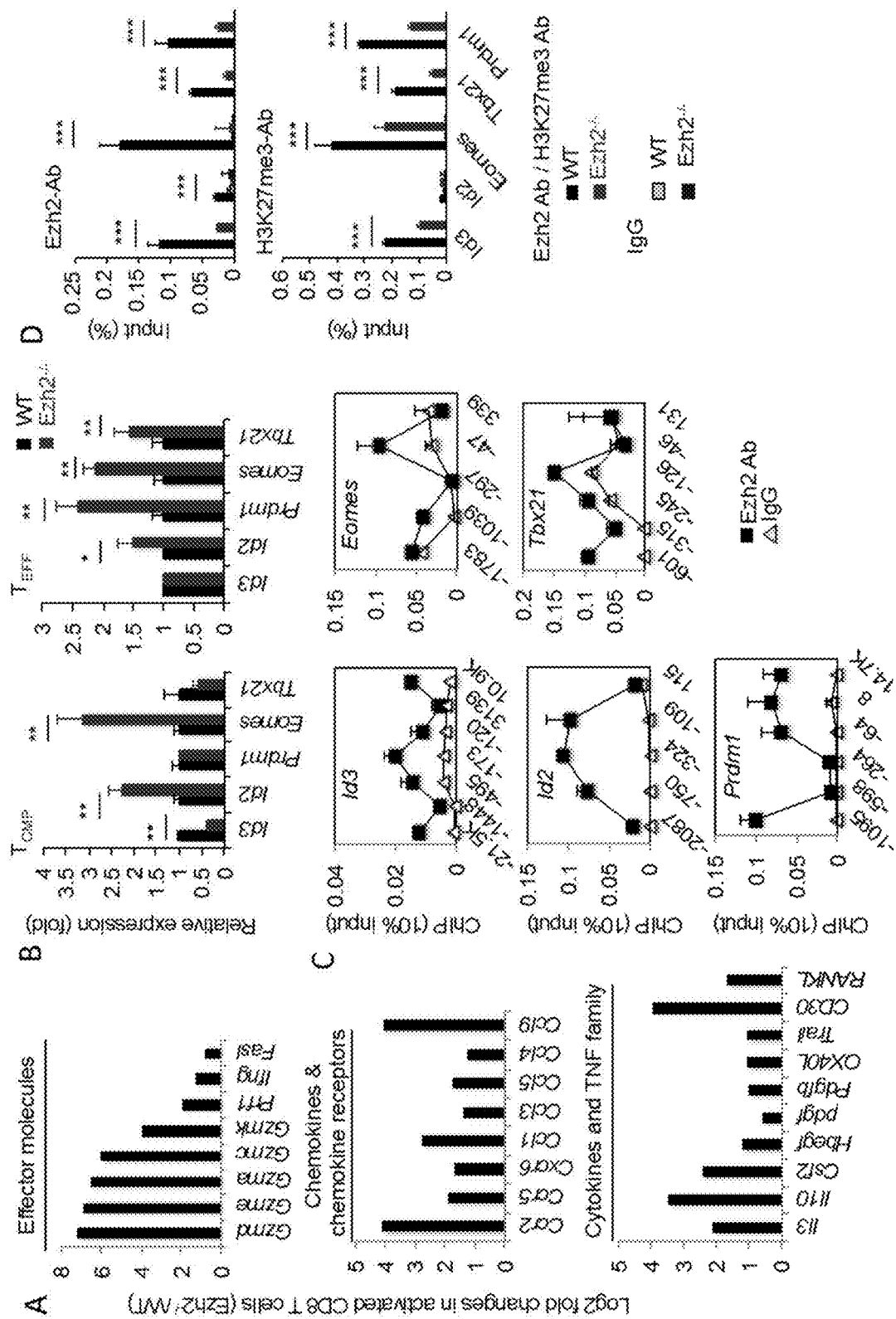
FIG. 10A through FIG. 10D, depicts exemplary experimental results demonstrating RNA-sequence profiling analysis identifies Ezh2-targeted genes in activated CD8+ T cells. WT and Ezh2$^{-/-}$ T$_N$ Pmel-1 cells were cultured in the presence of anti-CD3/CD28 Abs and IL-2. Three days later, cells were collected to extract RNA and chromatin. RNA sequencing was performed using freshly isolated WT TN, Ezh2$^{-/-}$ T$_N$, activated WT Pmel-1 cells, and activated Ezh2$^{-/-}$ Pmel-1 cells. Using one-way ANOVA analysis, transcripts with p<0.01 and q<0.01 were selected for comparing paired groups and at least a 1.5-fold difference from the means for the paired groups.

Ezh2 Orchestrates Expression of Genes Essential for Programming Memory Properties To identify the Ezh2-targeted genes associated with effector and memory differentiation, genome-wide RNA sequencing of WT and Ezh2$^{−/−}$ Pmel-1 cells was performed after TCR activation for 3 days. Ezh2 deficiency had minimal effect on gene expression in $T_N$ (FIG. 9A; Table 1). In contrast, TCR activation of Ezh2$^{−/−}$ Pmel-1 cells led to the up-regulation of 279 genes and down-regulation of 168 genes compared to their WT counterparts (FIG. 9A; Table 3). Ingenuity pathway analysis revealed that genes altered in activated Ezh2$^{−/−}$ Pmel-1 cells were associated with cellular proliferation, cell death and survival, and cell function and maintenance (FIG. 9B). Of note (FIG. 9C), Ezh2 deficiency upregulated Id2, Prdm1 and Eomes, all critical for effector differentiation and functionality (Chang et al., 2014, Nat Immunol, 15:1104-1115; Kaech and Cui, 2012, Nat Rev Immunol, 12:749-761), and decreased Id3, which controls memory formation (Ji et al., 2011, Nat Immunol, 12:1230-1237; Yang et al., 2011, Nat Immunol, 12:1221-1229; Verykokakis et al., 2010, Immunity, 33:203-215). RT-PCR analysis validated the alteration of these Ezh2 targeted genes in CD8+ T cells (FIG. 9D and FIG. 9E). RNA-seq gene profiling analysis confirmed the role of Ezh2 in restraining effector differentiation, as evidenced by dramatically upregulated effector molecules, chemokines, chemokine receptors and TNF receptor family members in TCR-activated Ezh2$^{−/−}$ CD8+ T cells (FIG. 10A).

TABLE 1

Genes differentially expressed in naïve Ezh2$^{−/−}$ CD8 T cells versus naïve WT T cells (Fold change >1.5, or <1.5)

| gene_id | locus | Naïve WT CD8 | Naïve Ezh2−/− CD8 | log2 (fold_change) | test_stat | status | p_value | q_value | significant | RNA_level |
|---|---|---|---|---|---|---|---|---|---|---|
| Ccl5 | chr11: 83525778-83530518 | 177.444 | 51.1744 | −1.79387 | −7.91254 | OK | 5.00E−05 | 0.000206 | yes | ok |
| Ccl3 | chr11: 83647842-83649378 | 6.51811 | 1.90123 | −1.77752 | −3.67457 | OK | 5.00E−05 | 0.000206 | yes | ok |
| Hist2h2bb | chr3: 96269699-96270192 | 6.57214 | 2.13454 | −1.62243 | −3.67977 | OK | 0.00045 | 0.001589 | yes | ok |
| Nin | chr12: 70011434-70111925 | 73.7714 | 24.5415 | −1.58784 | −4.40616 | OK | 5.00E−05 | 0.000206 | yes | ok |
| Ccl4 | chr11: 83662583-83664683 | 14.0633 | 4.90583 | −1.51937 | −3.96542 | OK | 5.00E−05 | 0.000206 | yes | ok |
| Eps8l1 | chr7: 4464741-4479242 | 17.5215 | 6.36759 | −1.46031 | −3.94616 | OK | 5.00E−05 | 0.000206 | yes | ok |
| Tigit | chr16: 43648860-43664184 | 7.53637 | 2.88364 | −1.38598 | −2.87733 | OK | 0.00025 | 0.000925 | yes | ok |
| Bhlhe40 | chr6: 108577038-108666925 | 9.23843 | 4.48681 | −1.04196 | −2.50642 | OK | 0.0001 | 0.000396 | yes | ok |
| Tpd52 | chr3: 8929435-9004515 | 52.1151 | 25.3762 | −1.03823 | −3.15744 | OK | 5.00E−05 | 0.000206 | yes | ok |
| Casp1 | chr9: 5298516-5307281 | 7.87819 | 3.95138 | −0.99551 | −2.38607 | OK | 0.0007 | 0.002375 | yes | ok |
| Irf4 | chr13: 30749257-30766927 | 16.5397 | 8.37344 | −0.98204 | −2.85602 | OK | 5.00E−05 | 0.000206 | yes | ok |
| Nr4a2 | chr2: 57107225-57124003 | 13.2125 | 6.76258 | −0.96625 | −2.28214 | OK | 0.0001 | 0.000396 | yes | ok |
| Ramp3 | chr11: 6650147-6677475 | 24.7116 | 12.8466 | −0.94381 | −2.10257 | OK | 0.00035 | 0.001262 | yes | ok |
| Coro2a | chr4: 46536936-46601929 | 6.25741 | 3.3306 | −0.90978 | −2.28583 | OK | 5.00E−05 | 0.000206 | yes | ok |
| Cd9 | chr6: 125460265-125494755 | 40.6082 | 22.8889 | −0.82712 | −2.87719 | OK | 0.00015 | 0.000577 | yes | ok |
| Ctla4 | chr1: 60909024-60915830 | 77.2275 | 43.5757 | −0.82559 | −2.61537 | OK | 0.0002 | 0.000753 | yes | ok |
| Rab4a | chr8: 123805995-123835291 | 9.25388 | 5.31495 | −0.8 | −2.00879 | OK | 0.0027 | 0.008051 | yes | ok |

TABLE 1-continued

Genes differentially expressed in naïve Ezh2$^{-/-}$ CD8 T cells versus naïve WT T cells (Fold change >1.5, or <1.5)

| gene_id | locus | Naïve WT CD8 | Naïve Ezh2-/- CD8 | log2 (fold_change) | test_stat | status | p_value | q_value | significant | RNA_level |
|---|---|---|---|---|---|---|---|---|---|---|
| Hist1h1c | chr13: 23738806-23740367 | 34.8786 | 20.2995 | −0.7809 | −2.56846 | OK | 0.00015 | 0.000577 | yes | ok |
| Slc6a19 | chr13: 73681156-73709856 | 74.2989 | 43.3502 | −0.7773 | −2.74686 | OK | 5.00E−05 | 0.000206 | yes | ok |
| Mgat5b | chr11: 116918862-116986944 | 12.1026 | 7.33401 | −0.72264 | −1.79018 | OK | 0.00265 | 0.007917 | yes | ok |
| Rgs2 | chr1: 143999337-144004149 | 96.206 | 59.9181 | −0.68313 | −2.09285 | OK | 0.00105 | 0.003422 | yes | ok |
| P2ry10 | chrX: 107089334-107104970 | 151.918 | 98.6038 | −0.62358 | −1.99669 | OK | 0.0028 | 0.00832 | yes | ok |
| 1700017B05Rik | chr9: 57252321-57262599 | 12.4067 | 8.22878 | −0.59236 | −1.80569 | OK | 0.0017 | 0.0053 | yes | ok |
| Ifi27l2a | chr12: 103442166-103443680 | 788 | 1186.64 | 0.590613 | 3.23723 | OK | 0.0019 | 0.00586 | yes | ok |
| Plac8 | chr5: 100553732-100572205 | 273.089 | 411.674 | 0.592129 | 2.63097 | OK | 0.00105 | 0.003422 | yes | ok |
| Ly6c2 | chr15: 75108160-75111949 | 291.992 | 443.618 | 0.603388 | 2.57358 | OK | 0.0015 | 0.004733 | yes | ok |
| Oas2 | chr5: 120730332-120749848 | 54.5233 | 83.315 | 0.611703 | 2.02334 | OK | 0.00075 | 0.002528 | yes | ok |
| Ifit3 | chr19: 34583528-34588982 | 36.0304 | 55.5065 | 0.623441 | 2.14075 | OK | 0.00045 | 0.001589 | yes | ok |
| Lyst | chr13: 13590408-13777440 | 20.5592 | 32.0504 | 0.64056 | 2.0861 | OK | 0.00055 | 0.001907 | yes | ok |
| Oasl2 | chr5: 114896933-114912245 | 19.2091 | 29.9971 | 0.643032 | 2.12529 | OK | 0.0006 | 0.002064 | yes | ok |
| Ggt1 | chr10: 75573592-75586182 | 32.9822 | 51.6865 | 0.6481 | 2.2042 | OK | 0.0006 | 0.002064 | yes | ok |
| Slfn5 | chr11: 82911252-82964850 | 29.3271 | 46.3573 | 0.660563 | 2.09837 | OK | 5.00E−05 | 0.000206 | yes | ok |
| Erdr1 | chrY: 90785441-90816465 | 214.865 | 342.444 | 0.672438 | 2.57477 | OK | 0.001 | 0.003276 | yes | ok |
| Ifit1 | chr19: 34640888-34650009 | 31.4782 | 50.9397 | 0.694437 | 2.39156 | OK | 0.00015 | 0.000577 | yes | ok |
| Isg15 | chr4: 156199423-156200818 | 88.1709 | 142.744 | 0.695059 | 2.84011 | OK | 0.0001 | 0.000396 | yes | ok |
| Baz2b | chr2: 59899362-60125740 | 7.54517 | 12.4577 | 0.723408 | 2.29167 | OK | 5.00E−05 | 0.000206 | yes | ok |
| Mx1 | chr16: 97447034-97462906 | 28.6372 | 47.7698 | 0.738209 | 2.29772 | OK | 5.00E−05 | 0.000206 | yes | ok |
| Ly6d | chr15: 74762055-74763567 | 18.8575 | 31.5612 | 0.743018 | 2.37906 | OK | 0.0033 | 0.009647 | yes | ok |
| Ctnna1 | chr18: 35118911-35254775 | 3.32225 | 5.58853 | 0.750309 | 1.84257 | OK | 0.0026 | 0.007782 | yes | ok |
| Ly6c1 | chr15: 75044017-75048837 | 21.2567 | 36.1645 | 0.766654 | 1.87141 | OK | 0.00225 | 0.006828 | yes | ok |
| B430306N03Rik | chr17: 48316161-48326511 | 3.9394 | 6.71447 | 0.769296 | 2.07626 | OK | 0.00105 | 0.003422 | yes | ok |
| Mx2 | chr16: 97536080-97560901 | 10.6858 | 18.2613 | 0.773093 | 2.16811 | OK | 0.00015 | 0.000577 | yes | ok |
| Ppic | chr18: 53406340-53418007 | 6.77981 | 11.6291 | 0.778424 | 2.09309 | OK | 0.00245 | 0.007377 | yes | ok |
| Cd163l1 | chr7: 140218266-140231145 | 13.7408 | 23.7645 | 0.79034 | 2.27749 | OK | 5.00E−05 | 0.000206 | yes | ok |
| I830012O16Rik | chr19: 34607956-34613401 | 5.15274 | 8.93211 | 0.79366 | 2.066 | OK | 0.00115 | 0.003718 | yes | ok |
| Rsad2 | chr12: 26442742-26456452 | 9.43614 | 17.2138 | 0.867295 | 2.86362 | OK | 5.00E−05 | 0.000206 | yes | ok |
| Tdgf1 | chr9: 110939607-110946158 | 2.7816 | 5.14692 | 0.887793 | 2.09312 | OK | 0.00195 | 0.005998 | yes | ok |
| Gadd45g | chr13: 51846674-51848474 | 8.16151 | 15.135 | 0.89098 | 2.44389 | OK | 0.00045 | 0.001589 | yes | ok |
| Gsto1 | chr19: 47854988-47864788 | 4.89655 | 9.26509 | 0.92004 | 2.30934 | OK | 0.00135 | 0.004299 | yes | ok |
| Ddit4 | chr10: 59949674-59951770 | 14.5796 | 27.6687 | 0.924299 | 2.87963 | OK | 5.00E−05 | 0.000206 | yes | ok |
| Vwa5a | chr9: 38718267-38743337 | 3.87167 | 7.46794 | 0.947755 | 2.58523 | OK | 5.00E−05 | 0.000206 | yes | ok |
| 1700097N02Rik | chr17: 30622440-30626905 | 4.50615 | 8.79491 | 0.964772 | 2.28857 | OK | 0.00265 | 0.007917 | yes | ok |
| Beta-s | chr7: 103826522-103827928 | 42.9388 | 89.2784 | 1.05603 | 4.15865 | OK | 5.00E−05 | 0.000206 | yes | ok |
| Stmn1 | chr4: 134468319-134473843 | 10.9678 | 25.4644 | 1.21521 | 3.57154 | OK | 5.00E−05 | 0.000206 | yes | ok |

TABLE 1-continued

Genes differentially expressed in naive Ezh2$^{-/-}$ CD8 T cells versus naïve WT T cells (Fold change >1.5, or <1.5)

| gene_id | locus | Naïve WT CD8 | Naïve Ezh2-/- CD8 | log2 (fold_change) | test_stat | status | p_value | q_value | significant | RNA_level |
|---|---|---|---|---|---|---|---|---|---|---|
| Top2a | chr11: 98992946-99024189 | 3.92345 | 9.79263 | 1.31957 | 3.66987 | OK | 5.00E-05 | 0.000206 | yes | ok |
| 5830411N06Rik | chr7: 140247300-140299791 | 9.77906 | 26.5075 | 1.43863 | 3.74004 | OK | 5.00E-05 | 0.000206 | yes | ok |
| Pxt1 | chr17: 28933985-28942262 | 0 | 35.311 | 20 | #NAME? | OK | 5.00E-05 | 0.000206 | yes | ok |
| Mir1932 | chr11: 119390471-119390561 | 0 | 82.2913 | 20 | #NAME? | OK | 0.0002 | 0.000753 | yes | ok |

TABLE 2

| gene_id | locus | Activated WT CD8 | Activated Ezh2-/- | log2 (fold_change) | test_stat |
|---|---|---|---|---|---|
| Ccl5 | chr11: 83525778-83530518 | 52.4865 | 175.015 | 1.73747 | 7.56866 |
| Ccl3 | chr11: 83647842-83649378 | 250.512 | 648.893 | 1.3731 | 4.50365 |
| Hist2h2bb | chr3: 96269699-96270192 | 2.59597 | 2.92983 | 0.174547 | 0.376093 |
| Nin | chr12: 70011434-70111925 | 22.1547 | 18.1026 | −0.29142 | −0.88202 |
| Ccl4 | chr11: 83662583-83664683 | 258.104 | 619.718 | 1.26366 | 4.71837 |
| Eps8l1 | chr7: 4464741-4479242 | 2.39868 | 1.02249 | −1.23015 | −2.20598 |
| Tigit | chr16: 43648860-43664184 | 89.5214 | 95.3887 | 0.091586 | 0.327446 |
| Bhlhe40 | chr6: 108577038-108666925 | 118.252 | 160.904 | 0.444338 | 1.22189 |
| Tpd52 | chr3: 8929435-9004515 | 44.3061 | 31.4849 | −0.49285 | −1.54141 |
| Casp1 | chr9: 5298516-5307281 | 5.93312 | 2.60335 | −1.18842 | −2.71242 |
| Irf4 | chr13: 30749257-30766927 | 81.7269 | 75.3077 | −0.11802 | −0.38452 |
| Nr4a2 | chr2: 57107225-57124003 | 27.3337 | 23.1734 | −0.23821 | −0.66282 |
| Ramp3 | chr11: 6650147-6677475 | 2.6432 | 4.82907 | 0.869457 | 1.40153 |
| Coro2a | chr4: 46536936-46601929 | 60.5208 | 69.9553 | 0.209003 | 0.634956 |
| Cd9 | chr6: 125460265-125494755 | 32.1545 | 57.1001 | 0.828474 | 3.11526 |
| Ctla4 | chr1: 60909024-60915830 | 265.086 | 227.398 | −0.22124 | −0.76084 |
| Rab4a | chr8: 123805995-123835291 | 5.09996 | 4.72029 | −0.11161 | −0.25957 |
| Hist1h1c | chr13: 23738806-23740367 | 4.17531 | 6.75436 | 0.693935 | 1.67523 |
| Slc6a19 | chr13: 73681156-73709856 | 4.53148 | 2.02788 | −1.16001 | −2.61914 |
| Mgat5b | chr11: 116918862-116986944 | 0.608261 | 0.334736 | −0.86167 | −1.21688 |
| Rgs2 | chr1: 143999337-144004149 | 8.68437 | 13.9715 | 0.685994 | 1.97598 |
| P2ry10 | chrX: 107089334-107104970 | 60.9674 | 35.0462 | −0.79878 | −2.99378 |
| 1700017B05Rik | chr9: 57252321-57262599 | 16.5123 | 18.8457 | 0.190694 | 0.620541 |
| Ifi27l2a | chr12: 103442166-103443680 | 1057.33 | 664.555 | −0.66997 | −3.27231 |
| Plac8 | chr5: 100553732-100572205 | 746.283 | 929.914 | 0.317375 | 1.27825 |
| Ly6c2 | chr15: 75108160-75111949 | 175.294 | 281.427 | 0.682984 | 2.86289 |
| Oas2 | chr5: 120730332-120749848 | 0.923124 | 1.05157 | 0.187947 | 0.351817 |
| Ifit3 | chr19: 34583528-34588982 | 2.5764 | 1.84752 | −0.47976 | −0.96645 |

TABLE 2-continued

| | | | | | |
|---|---|---|---|---|---|
| Lyst | chr13: 13590408-13777440 | 14.7823 | 12.4555 | −0.24708 | −0.80906 |
| Oasl2 | chr5: 114896933-114912245 | 1.48429 | 1.6983 | 0.194317 | 0.378914 |
| Ggt1 | chr10: 75573592-75586182 | 3.46413 | 6.21196 | 0.842557 | 1.98981 |
| Slfn5 | chr11: 82911252-82964850 | 2.08347 | 2.12826 | 0.03069 | 0.070671 |
| Erdr1 | chrY: 90785441-90816465 | 92.797 | 214.099 | 1.20613 | 4.91218 |
| Ifit1 | chr19: 34640888-34650009 | 3.28203 | 2.97265 | −0.14284 | −0.33053 |
| Isg15 | chr4: 156199423-156200818 | 38.3052 | 31.7783 | −0.2695 | −0.86948 |
| Baz2b | chr2: 59899362-60125740 | 2.2778 | 4.81612 | 1.08023 | 3.00839 |
| Mx1 | chr16: 97447034-97462906 | 6.4328 | 8.14191 | 0.339921 | 0.858622 |
| Ly6d | chr15: 74762055-74763567 | 0.919725 | 1.56058 | 0.762806 | 1.30384 |
| Ctnna1 | chr18: 35118911-35254775 | 25.4877 | 43.3358 | 0.765758 | 2.52378 |
| Ly6c1 | chr15: 75044017-75048837 | 9.7877 | 14.1628 | 0.533063 | 1.09506 |
| B430306N03Rik | chr17: 48316161-48326511 | 0.576105 | 1.37776 | 1.25792 | 2.25568 |
| Mx2 | chr16: 97536080-97560901 | 1.92411 | 1.78102 | −0.11149 | −0.18785 |
| Ppic | chr18: 53406340-53418007 | 6.98088 | 9.16521 | 0.392758 | 0.983796 |
| Cd163l1 | chr7: 140218266-140231145 | 0.403075 | 1.2321 | 1.612 | 2.45654 |
| I830012O16Rik | chr19: 34607956-34613401 | 0.564784 | 0.333019 | −0.76209 | −1.08108 |
| Rsad2 | chr12: 26442742-26456452 | 0.784511 | 0.596199 | −0.396 | −0.69746 |
| Tdgf1 | chr9: 110939607-110946158 | 0.413496 | 0.291862 | −0.50259 | −0.68905 |
| Gadd45g | chr13: 51846674-51848474 | 43.4029 | 127.932 | 1.55951 | 5.39775 |
| Gsto1 | chr19: 47854988-47864788 | 22.0163 | 40.8322 | 0.891135 | 3.04207 |
| Ddit4 | chr10: 59949674-59951770 | 152.318 | 113.12 | −0.42924 | −1.44543 |
| Vwa5a | chr9: 38718267-38743337 | 11.6137 | 8.13297 | −0.51397 | −1.52935 |
| 1700097N02Rik | chr17: 30622440-30626905 | 17.8083 | 13.7049 | −0.37786 | −1.073 |
| Beta-s | chr7: 103826522-103827928 | 0.047418 | 0.15611 | 1.71905 | 0 |
| Stmn1 | chr4: 134468319-134473843 | 435.214 | 404.33 | −0.10619 | −0.39549 |
| Top2a | chr11: 98992946-99024189 | 240.794 | 205.346 | −0.22975 | −0.65882 |
| 5830411N06Rik | chr7: 140247300-140299791 | 0.100796 | 0.319545 | 1.66458 | 1.58438 |
| Pxt1 | chr17: 28933985-28942262 | 0.050716 | 9.81045 | 7.59573 | 6.17196 |
| Mir1932 | chr11: 119390471-119390561 | 17.9759 | 15.3618 | −0.22671 | 0 |

| gene_id | status | p_value | q_value | significant | RNA_level |
|---|---|---|---|---|---|
| Ccl5 | OK | 5.00E−05 | 0.000206 | yes | ok |
| Ccl3 | OK | 5.00E−05 | 0.000206 | yes | ok |
| Hist2h2bb | OK | 0.6908 | 0.844261 | no | bad |
| Nin | OK | 0.1073 | 0.20893 | no | ok |
| Ccl4 | OK | 5.00E−05 | 0.000206 | yes | ok |
| Eps8l1 | OK | 0.0002 | 0.000753 | yes | bad |
| Tigit | OK | 0.6463 | 0.812903 | no | ok |
| Bhlhe40 | OK | 0.0342 | 0.077707 | no | ok |
| Tpd52 | OK | 0.011 | 0.028477 | yes | ok |
| Casp1 | OK | 0.00015 | 0.000577 | yes | ok |
| Irf4 | OK | 0.53465 | 0.723201 | no | ok |
| Nr4a2 | OK | 0.24935 | 0.414017 | no | ok |
| Ramp3 | OK | 0.0131 | 0.033286 | yes | bad |
| Coro2a | OK | 0.2595 | 0.426889 | no | ok |
| Cd9 | OK | 5.00E−05 | 0.000206 | yes | ok |
| Ctla4 | OK | 0.27855 | 0.451184 | no | ok |
| Rab4a | OK | 0.6846 | 0.839935 | no | ok |

TABLE 2-continued

| | | | | | |
|---|---|---|---|---|---|
| Hist1h1c | OK | 0.0098 | 0.025686 | yes | ok |
| Slc6a19 | OK | 0.00015 | 0.000577 | yes | bad |
| Mgat5b | OK | 0.0387 | 0.086647 | no | bad |
| Rgs2 | OK | 0.00225 | 0.006828 | yes | ok |
| P2ry10 | OK | 5.00E−05 | 0.000206 | yes | ok |
| 1700017B05Rik | OK | 0.28445 | 0.458438 | no | ok |
| Ifi27l2a | OK | 0.00115 | 0.003718 | yes | ok |
| Plac8 | OK | 0.1221 | 0.233026 | no | ok |
| Ly6c2 | OK | 0.0005 | 0.001749 | yes | ok |
| Oas2 | OK | 0.5585 | 0.743246 | no | bad |
| Ifit3 | OK | 0.12535 | 0.238128 | no | bad |
| Lyst | OK | 0.17335 | 0.311038 | no | ok |
| Oasl2 | OK | 0.52775 | 0.717004 | no | bad |
| Ggt1 | OK | 0.00255 | 0.007648 | yes | ok |
| Slfn5 | OK | 0.90495 | 0.961442 | no | bad |
| Erdr1 | OK | 5.00E−05 | 0.000206 | yes | ok |
| Ifit1 | OK | 0.58665 | 0.766747 | no | bad |
| Isg15 | OK | 0.23875 | 0.400989 | no | ok |
| Baz2b | OK | 5.00E−05 | 0.000206 | yes | bad |
| Mx1 | OK | 0.12935 | 0.244595 | no | ok |
| Ly6d | OK | 0.114 | 0.219981 | no | bad |
| Ctnna1 | OK | 5.00E−05 | 0.000206 | yes | ok |
| Ly6c1 | OK | 0.0601 | 0.127139 | no | ok |
| B430306N03Rik | OK | 0.0006 | 0.002064 | yes | bad |
| Mx2 | OK | 0.7287 | 0.868529 | no | bad |
| Ppic | OK | 0.14455 | 0.268161 | no | ok |
| Cd163l1 | OK | 0.0002 | 0.000753 | yes | bad |
| I830012O16Rik | OK | 0.0927 | 0.184646 | no | bad |
| Rsad2 | OK | 0.2729 | 0.444081 | no | bad |
| Tdgf1 | OK | 0.29915 | 0.476437 | no | bad |
| Gadd45g | OK | 5.00E−05 | 0.000206 | yes | ok |
| Gsto1 | OK | 5.00E−05 | 0.000206 | yes | ok |
| Ddit4 | OK | 0.0264 | 0.061887 | no | ok |
| Vwa5a | OK | 0.00995 | 0.026034 | yes | ok |
| 1700097N02Rik | OK | 0.15375 | 0.282115 | no | ok |
| Beta-s | NO TEST | 1 | 1 | no | bad |
| Stmn1 | OK | 0.5642 | 0.747904 | no | ok |
| Top2a | OK | 0.26455 | 0.433403 | no | ok |
| 5830411N06Rik | OK | 0.0064 | 0.017537 | yes | bad |
| Pxt1 | OK | 0.02205 | 0.052787 | no | ok |
| Mir1932 | NO TEST | 1 | 1 | no | ok |

TABLE 3

Genes differentially expressed in activated Ezh2−/− CD8 T cells versus WT CD8 T cells (fold changes >1.5, or <1.5)

| gene_id | locus | Activated WT CD8 | Activated Ezh2−/− CD8 | fold change | test_stat |
|---|---|---|---|---|---|
| Xist | chrX: 103431516-103484957 | 26.8128 | 0.0221 | 0.000824 | −13.6563 |
| Acvrl1 | chr15: 101128536-101145336 | 5.7217 | 1.45649 | 0.254557 | −4.22102 |
| Dntt | chr19: 41029274-41059525 | 11.7614 | 3.27165 | 0.27817 | −3.86352 |
| Tlr1 | chr5: 64924679-64933558 | 9.80037 | 2.8643 | 0.292265 | −4.27162 |
| Ccdc164 | chr5: 30341662-30366708 | 13.7634 | 4.12708 | 0.299858 | −3.84333 |
| Matk | chr10: 81257544-81262981 | 22.0966 | 7.77785 | 0.351993 | −4.05463 |
| Tespa1 | chr10: 130322851-130362642 | 23.8355 | 8.54216 | 0.358379 | −4.24969 |
| Dapl1 | chr2: 59484652-59505020 | 126.459 | 47.4318 | 0.375077 | −5.78612 |
| Id3 | chr4: 136143821-136145392 | 63.3329 | 24.4144 | 0.385494 | −4.73159 |
| St6gal1 | chr16: 23224739-23360350 | 39.9614 | 15.6625 | 0.391941 | −4.02221 |
| Cd101 | chr3: 100993528-101029495 | 7.58971 | 2.99384 | 0.39446 | −3.21875 |
| Lst1 | chr17: 35185094-35188440 | 28.1189 | 11.2901 | 0.401513 | −4.70168 |
| Fam183b | chr11: 58792801-58801960 | 14.0809 | 5.65756 | 0.401792 | −2.03605 |

TABLE 3-continued

Genes differentially expressed in activated Ezh2−/− CD8 T cells versus WT CD8 T cells (fold changes >1.5, or <1.5)

| Gene | Location | | | | |
|---|---|---|---|---|---|
| Tbxa2r | chr10: 81328730-81335172 | 20.8714 | 8.49938 | 0.407226 | −3.82905 |
| Ephx1 | chr1: 180989555-181017495 | 45.7984 | 18.7142 | 0.408622 | −3.96693 |
| Igfbp4 | chr11: 99041259-99052643 | 74.0214 | 32.0504 | 0.432988 | −3.59721 |
| Casp1 | chr9: 5298516-5307281 | 5.93312 | 2.60335 | 0.438783 | −2.71242 |
| Cd226 | chr18: 89197426-89270327 | 21.2687 | 9.39293 | 0.441633 | −3.27388 |
| Ifngr2 | chr16: 91547093-91564007 | 6.80989 | 3.07272 | 0.451213 | −2.80499 |
| Amz2 | chr11: 109425945-109438148 | 17.5616 | 8.05377 | 0.458604 | −3.25821 |
| Gbp10 | chr5: 105215698-105239533 | 6.22054 | 2.91952 | 0.469335 | −2.83066 |
| Ifi203 | chr1: 173920402-173942492 | 32.4039 | 15.3686 | 0.474283 | −3.59399 |
| Sh3bp5 | chr14: 31373963-31436033 | 28.4269 | 13.5145 | 0.475412 | −3.33857 |
| Arl5c | chr11: 97989579-97996173 | 27.0579 | 12.9065 | 0.476996 | −3.18114 |
| Trp53inp1 | chr4: 11156440-11174377 | 41.6773 | 20.0366 | 0.480757 | −3.5361 |
| N4bp2l1 | chr5: 150571642-150594525 | 8.19176 | 3.94537 | 0.481628 | −2.62387 |
| Slamf6 | chr1: 171917536-171943868 | 19.1223 | 9.27956 | 0.485274 | −3.24661 |
| Abcg1 | chr17: 31057693-31117981 | 7.9424 | 3.8716 | 0.487461 | −2.91507 |
| H2-Oa | chr17: 34083842-34095309 | 15.6575 | 7.64058 | 0.487979 | −2.21573 |
| Synpo | chr18: 60593989-60624305 | 6.0411 | 2.95647 | 0.489391 | −2.59004 |
| Iigp1 | chr18: 60376028-60392629 | 55.8167 | 27.3721 | 0.490393 | −3.25623 |
| Smpdl3a | chr10: 57794543-57811830 | 12.8627 | 6.34526 | 0.493308 | −2.84829 |
| Pbx4 | chr8: 69832703-69872292 | 9.05181 | 4.48091 | 0.495027 | −2.36801 |
| 4930417O13Rik | chr6: 125265524-125273777 | 25.2016 | 12.4778 | 0.495117 | −2.89143 |
| Arrdc3 | chr13: 80883421-80896043 | 11.2828 | 5.59091 | 0.495525 | −3.21841 |
| A430093F15Rik | chr19: 10740946-10786043 | 21.0268 | 10.4374 | 0.496385 | −3.01299 |
| Ltb | chr17: 35194506-35196305 | 350.01 | 173.791 | 0.496532 | −3.8411 |
| Kdm6b | chr11: 69398517-69413675 | 8.93597 | 4.44157 | 0.497046 | −2.92245 |
| Nr4a1 | chr15: 101266845-101274794 | 60.7444 | 30.6008 | 0.503763 | −2.96855 |
| Igflr1 | chr7: 30565426-30567962 | 27.3959 | 13.9354 | 0.508668 | −3.01332 |
| Bambi-ps1 | chr2: 122466582-122467797 | 5.80406 | 2.95341 | 0.508852 | −2.14009 |
| Cd68 | chr11: 69664370-69666062 | 7.23455 | 3.7192 | 0.514089 | −2.20753 |
| Sytl1 | chr4: 133253089-133263087 | 24.4842 | 12.9216 | 0.527752 | −2.75051 |
| Rasgef1a | chr6: 118066384-118091546 | 5.0176 | 2.65118 | 0.528375 | −2.13087 |
| Ipcef1 | chr10: 6788600-7038209 | 39.072 | 20.7888 | 0.532064 | −2.72394 |
| Aldoc | chr11: 78324197-78326760 | 53.4865 | 28.6425 | 0.535509 | −2.65134 |
| Mettl20 | chr6: 149141512-149151170 | 9.82863 | 5.29497 | 0.538729 | −2.03603 |
| Pvr | chr7: 19903577-19921143 | 13.1702 | 7.09726 | 0.538887 | −2.61951 |
| Btla | chr16: 45224336-45252895 | 21.5079 | 11.5985 | 0.539264 | −2.71756 |
| Gm14446 | chr19: 34592887-34601968 | 7.30804 | 3.9476 | 0.540172 | −2.05915 |
| I730030J21Rik | chr15: 100730504-100732737 | 36.9513 | 19.9735 | 0.540536 | −2.0674 |

TABLE 3-continued

Genes differentially expressed in activated Ezh2−/− CD8 T cells versus WT CD8 T cells (fold changes >1.5, or <1.5)

| Gene | Location | | | | |
|---|---|---|---|---|---|
| Ccr7 | chr11: 99144198-99155077 | 415.017 | 224.875 | 0.541846 | −2.88505 |
| Tox | chr4: 6687385-6990723 | 8.32052 | 4.53155 | 0.544623 | −2.42095 |
| Pacsin1 | chr17: 27655681-27711106 | 13.9847 | 7.63612 | 0.546033 | −2.15223 |
| Pecam1 | chr11: 106654217-106715281 | 26.0214 | 14.2983 | 0.549483 | −2.60043 |
| 2610019F03Rik | chr8: 13952007-13974777 | 5.49499 | 3.02221 | 0.549994 | −2.12343 |
| Tspan32 | chr7: 143005045-143019485 | 38.1264 | 20.9806 | 0.55029 | −2.53946 |
| Slamf1 | chr1: 171767131-171801184 | 17.9823 | 10.0225 | 0.557353 | −2.64965 |
| Ncf1 | chr5: 134220259-134229625 | 56.5338 | 31.6122 | 0.559174 | −2.65812 |
| Chd3 | chr11: 69343272-69369426 | 32.0566 | 17.9952 | 0.561356 | −2.53321 |
| A430107P09Rik | chr14: 53665939-53668335 | 8.11815 | 4.56342 | 0.562125 | −2.35453 |
| Ccng2 | chr5: 93267572-93276231 | 44.7678 | 25.231 | 0.563597 | −2.79351 |
| Adamts6 | chr13: 104287872-104494763 | 10.1634 | 5.73183 | 0.563969 | −2.45808 |
| Klf3 | chr5: 64803522-64830129 | 7.08401 | 3.99973 | 0.564614 | −2.1218 |
| Sfn | chr4: 133600555-133602168 | 21.4176 | 12.1044 | 0.56516 | −2.42766 |
| Fyb | chr15: 6579870-6663312 | 89.7224 | 51.0287 | 0.56874 | −2.55185 |
| Bcl11b | chr12: 107910402-108003414 | 16.8982 | 9.61098 | 0.568756 | −2.56449 |
| Arhgef18 | chr8: 3393007-3456600 | 16.3763 | 9.33476 | 0.570018 | −2.49437 |
| Zfp36 | chr7: 28376783-28379228 | 28.4037 | 16.2835 | 0.573288 | −2.59919 |
| Sertad3 | chr7: 27473839-27477364 | 13.5293 | 7.76889 | 0.574225 | −2.1988 |
| P2ry10 | chrX: 107089334-107104970 | 60.9674 | 35.0462 | 0.574835 | −2.99378 |
| Cpm | chr10: 117629499-117687352 | 5.42913 | 3.12669 | 0.575909 | −2.14945 |
| Fut7 | chr2: 25423693-25426373 | 13.8057 | 7.99901 | 0.5794 | −1.96196 |
| Serpine1 | chr5: 137061505-137072272 | 7.55716 | 4.38047 | 0.579644 | −2.03463 |
| Slfn1 | chr11: 83116844-83122659 | 62.1912 | 36.1695 | 0.581586 | −2.79286 |
| Per1 | chr11: 69098955-69109957 | 16.9178 | 9.84586 | 0.581983 | −2.14154 |
| Trib3 | chr2: 152337424-152344060 | 11.2776 | 6.5676 | 0.582359 | −2.10319 |
| Nr4a3 | chr4: 48051247-48083352 | 40.8464 | 24.0451 | 0.588672 | −2.27983 |
| Tnfsf14 | chr17: 57189491-57194186 | 14.6153 | 8.63551 | 0.590855 | −2.05461 |
| Slc35d3 | chr10: 19847916-19851459 | 6.96276 | 4.11528 | 0.591042 | −1.90249 |
| Ddb2 | chr2: 91202911-91237066 | 24.2494 | 14.3647 | 0.592375 | −1.71434 |
| Cbx4 | chr11: 119077570-119086237 | 17.4991 | 10.3816 | 0.593263 | −2.40502 |
| Cdkn1b | chr6: 134920400-134925525 | 41.0625 | 24.4032 | 0.594293 | −2.66753 |
| Gbp8 | chr5: 105014152-105053561 | 19.4071 | 11.5549 | 0.595394 | −2.32878 |
| Irgm2 | chr11: 58214976-58222783 | 32.9768 | 19.7659 | 0.599388 | −2.54205 |
| Il6st | chr13: 112464069-112506860 | 11.7091 | 7.03028 | 0.600411 | −2.3056 |
| Hivep2 | chr10: 13966378-14151378 | 6.32435 | 3.79954 | 0.600779 | −2.27123 |
| Slc43a2 | chr11: 75531693-75577572 | 11.2124 | 6.73955 | 0.601083 | −2.28204 |
| Socs2 | chr10: 95411489-95416857 | 40.1215 | 24.195 | 0.603043 | −2.07087 |

TABLE 3-continued

Genes differentially expressed in activated Ezh2−/− CD8 T cells versus WT CD8 T cells (fold changes >1.5, or <1.5)

| Gene | Location | | | | |
|---|---|---|---|---|---|
| Rab37 | chr11: 115091430-115162240 | 14.0946 | 8.50233 | 0.603234 | −1.83725 |
| Plcxd2 | chr16: 45959260-46010413 | 7.60021 | 4.58773 | 0.603632 | −2.34244 |
| Abhd8 | chr8: 71456699-71463657 | 39.9242 | 24.1173 | 0.604076 | −2.36373 |
| Rara | chr11: 98937695-98974942 | 18.4409 | 11.1462 | 0.604426 | −2.10711 |
| H2-DMa | chr17: 34122831-34139101 | 31.8286 | 19.2781 | 0.605684 | −2.35984 |
| Ms4a4c | chr19: 11407660-11427246 | 44.1784 | 26.817 | 0.607016 | −2.61765 |
| Klf2 | chr8: 72319061-72321654 | 30.5281 | 18.5362 | 0.607183 | −2.38207 |
| Slc35g1 | chr19: 38395979-38405607 | 27.5071 | 16.7432 | 0.608686 | −2.52292 |
| H2afv | chr11: 6427225-6444443 | 55.0864 | 33.6144 | 0.610211 | −2.55414 |
| Dhx58 | chr11: 100694883-100704271 | 22.2092 | 13.5611 | 0.610606 | −2.01669 |
| Inadl | chr4: 98395825-98719603 | 5.43573 | 3.33099 | 0.612797 | −1.76363 |
| Orai2 | chr5: 136147460-136170656 | 19.0761 | 11.6942 | 0.613028 | −2.23503 |
| Zfp36l1 | chr12: 80107759-80113013 | 44.5626 | 27.3272 | 0.613231 | −2.54889 |
| Gbp6 | chr5: 105270701-105293699 | 28.1942 | 17.3324 | 0.61475 | −2.30571 |
| Spry1 | chr3: 37639949-37644599 | 17.9025 | 11.0101 | 0.615006 | −2.09947 |
| Syt11 | chr3: 88744700-88772599 | 8.17066 | 5.03275 | 0.615954 | −2.04147 |
| Tgtp1 | chr11: 48985328-48992246 | 13.7508 | 8.48572 | 0.617108 | −2.17441 |
| Tecpr1 | chr5: 144195346-144223578 | 37.069 | 22.908 | 0.617984 | −2.23256 |
| A430078G23Rik | chr8: 3353414-3390299 | 10.347 | 6.40214 | 0.618745 | −2.0022 |
| Igtp | chr11: 58199555-58207592 | 287.776 | 178.094 | 0.618863 | −2.19267 |
| Plekhg2 | chr7: 28359603-28372662 | 14.5291 | 9.03047 | 0.621544 | −1.96741 |
| Itgb7 | chr15: 102215994-102231935 | 168.174 | 104.746 | 0.622842 | −2.21237 |
| Cd2 | chr3: 101275907-101287939 | 273.564 | 170.478 | 0.623176 | −2.56738 |
| Sh2b3 | chr5: 121817214-121836801 | 14.1339 | 8.81637 | 0.623774 | −1.99447 |
| Folr4 | chr9: 14885813-14903951 | 59.2334 | 36.9788 | 0.62429 | −2.04978 |
| Poldip3 | chr15: 83125977-83149336 | 42.5386 | 26.6307 | 0.626035 | −2.20794 |
| Gprin3 | chr6: 59352460-59426290 | 13.7482 | 8.62714 | 0.627509 | −1.89057 |
| Utrn | chr10: 12382187-12861735 | 17.1981 | 10.8008 | 0.628022 | −2.04827 |
| Ifi27l2a | chr12: 103442166-103443680 | 1057.33 | 664.555 | 0.62852 | −3.27231 |
| Itga6 | chr2: 71787082-71856758 | 17.1293 | 10.7703 | 0.628763 | −2.11924 |
| Plcg1 | chr2: 160731309-160872990 | 46.1988 | 29.1174 | 0.630264 | −2.11194 |
| Samhd1 | chr2: 157097528-157135222 | 200.104 | 126.192 | 0.630632 | −2.00425 |
| Ing2 | chr8: 47667177-47675159 | 10.9264 | 6.89415 | 0.630965 | −2.01829 |
| Mov10 | chr3: 104794833-104818563 | 29.734 | 18.7712 | 0.631302 | −1.95304 |
| Samd9l | chr6: 3372257-3399571 | 24.2586 | 15.4032 | 0.634958 | −2.1744 |
| Lbh | chr17: 72918304-72941946 | 44.8844 | 28.5321 | 0.63568 | −2.29748 |
| Setx | chr2: 29124991-29182471 | 33.7821 | 21.4827 | 0.635919 | −2.09918 |
| Elk4 | chr1: 132007604-132025684 | 12.9397 | 8.23066 | 0.63608 | −2.08021 |

TABLE 3-continued

Genes differentially expressed in activated Ezh2−/− CD8 T cells versus WT CD8 T cells (fold changes >1.5, or <1.5)

| | | | | | |
|---|---|---|---|---|---|
| BC021614 | chr19: 4057486-4059294 | 88.7244 | 56.4459 | 0.636193 | −2.63224 |
| Gm8369 | chr19: 11492037-11512577 | 39.1506 | 24.9472 | 0.637212 | −2.34139 |
| Fam189b | chr3: 89183224-89189289 | 21.8838 | 13.9761 | 0.638652 | −2.12633 |
| Tpcn1 | chr5: 120534156-120588613 | 29.6809 | 18.9567 | 0.638682 | −2.12959 |
| Ifi47 | chr11: 49037659-49135387 | 207.521 | 132.687 | 0.639392 | −2.13659 |
| Ccdc64 | chr5: 115649285-115731559 | 38.994 | 24.9939 | 0.640969 | −2.03094 |
| Gbp2 | chr3: 142620662-142638008 | 276.832 | 177.675 | 0.641815 | −1.93224 |
| Dlg4 | chr11: 70018604-70045531 | 21.5293 | 13.8399 | 0.642839 | −1.83776 |
| Bzrap1 | chr11: 87760540-87785928 | 7.39547 | 4.77492 | 0.645656 | −1.67045 |
| Rnf167 | chr11: 70647588-70651414 | 33.6504 | 21.7349 | 0.645902 | −2.08938 |
| Kbtbd11 | chr8: 15011024-15033332 | 43.5808 | 28.1491 | 0.645905 | −2.03415 |
| Rab3ip | chr10: 116905783-116950380 | 14.4626 | 9.35141 | 0.64659 | −1.95408 |
| Ikbke | chr1: 131254601-131279563 | 32.8494 | 21.2506 | 0.646909 | −1.97952 |
| Fam117a | chr11: 95337017-95381872 | 16.3142 | 10.5657 | 0.647636 | −1.898 |
| Inpp4b | chr8: 81715199-82122561 | 31.855 | 20.6541 | 0.64838 | −2.10628 |
| Irf1 | chr11: 53770013-53778374 | 116.768 | 75.8866 | 0.649893 | −1.92697 |
| Lrig1 | chr6: 94500313-94700145 | 12.2592 | 7.97305 | 0.650372 | −1.74419 |
| Rhoh | chr5: 65863568-65896700 | 28.6812 | 18.6966 | 0.651877 | −2.13345 |
| Ift80 | chr3: 68892498-69004570 | 21.4493 | 13.9901 | 0.652242 | −2.09083 |
| Entpd5 | chr12: 84373856-84409029 | 12.4169 | 8.11037 | 0.653171 | −1.93447 |
| Dpp4 | chr2: 62330072-62412231 | 43.4738 | 28.4219 | 0.653773 | −2.03036 |
| Nfatc1 | chr18: 80606204-80713071 | 50.749 | 33.2851 | 0.655876 | −1.9194 |
| Pou2f2 | chr7: 25091114-25132460 | 15.1923 | 9.96514 | 0.655935 | −1.70721 |
| Ndrg2 | chr14: 51905270-51913488 | 38.1583 | 25.0596 | 0.656726 | −1.72257 |
| Tob2 | chr15: 81848269-81858326 | 18.0119 | 11.8294 | 0.656757 | −1.97269 |
| Oas3 | chr5: 120753097-120777659 | 25.4059 | 16.6884 | 0.656872 | −1.88667 |
| Pink1 | chr4: 138313409-138326296 | 18.6235 | 12.2361 | 0.657027 | −1.84682 |
| Sbk1 | chr7: 126272618-126294999 | 10.3896 | 6.83189 | 0.65757 | −1.7857 |
| Tap1 | chr17: 34187555-34197225 | 201.064 | 132.34 | 0.658202 | −1.81972 |
| 2810474O19Rik | chr6: 149309413-149335663 | 11.2458 | 7.40256 | 0.658251 | −1.9478 |
| Amica1 | chr9: 45079182-45135606 | 30.2547 | 19.9287 | 0.658698 | −1.83515 |
| Gm12250 | chr11: 58183842-58190198 | 50.4354 | 33.2642 | 0.65954 | −1.97167 |
| 1600014C10Rik | chr7: 38183216-38197565 | 19.6014 | 12.9357 | 0.659935 | −1.89973 |
| Mib2 | chr4: 155654469-155669254 | 9.12179 | 6.03242 | 0.66132 | −1.61086 |
| Irgm1 | chr11: 48865248-48871346 | 93.2485 | 61.682 | 0.661479 | −2.06522 |
| Ptpn18 | chr1: 34459745-34473779 | 47.0495 | 31.1992 | 0.663115 | −2.00384 |
| Gbp9 | chr5: 105078393-105110292 | 26.6683 | 17.7046 | 0.663882 | −1.98214 |
| Mndal | chr1: 173857219-173880187 | 54.1633 | 35.9747 | 0.664189 | −1.99902 |

TABLE 3-continued

Genes differentially expressed in activated Ezh2−/− CD8 T cells versus WT CD8 T cells (fold changes >1.5, or <1.5)

| | | | | | |
|---|---|---|---|---|---|
| 2410006H16Rik | chr11: 62602876-62604806 | 392.404 | 260.795 | 0.664608 | −3.20568 |
| Map4k2 | chr19: 6341249-6353527 | 91.0205 | 60.6027 | 0.665813 | −1.98209 |
| Slc17a9 | chr2: 180725338-180742278 | 22.9225 | 15.2625 | 0.665828 | −1.94403 |
| Chd7 | chr4: 8690920-8866809 | 14.7703 | 22.211 | 1.503765 | 1.66579 |
| Agpat4 | chr17: 12119283-12219640 | 16.6713 | 25.123 | 1.506958 | 1.90163 |
| Pdia6 | chr12: 17266594-17324730 | 107.518 | 163.012 | 1.516135 | 1.9583 |
| Slc25a24 | chr3: 109123148-109168409 | 10.6296 | 16.2706 | 1.530678 | 2.06077 |
| Scd1 | chr19: 44394449-44407709 | 11.744 | 17.9825 | 1.531211 | 1.96681 |
| Smim3 | chr18: 60474190-60501983 | 12.4183 | 19.0471 | 1.533795 | 1.93415 |
| Ptprj | chr2: 90429755-90580647 | 4.2026 | 6.45077 | 1.534945 | 1.77672 |
| Gpr65 | chr12: 98268634-98276722 | 38.9042 | 59.7607 | 1.536099 | 2.2777 |
| Ctla2a | chr13: 60934154-60936625 | 38.4191 | 59.0806 | 1.537791 | 1.94518 |
| Phlpp1 | chr1: 106171868-106394245 | 3.32283 | 5.12474 | 1.542279 | 1.78313 |
| Nabp1 | chr1: 51469487-51478399 | 68.6757 | 106.025 | 1.54385 | 2.3354 |
| Bcl3 | chr7: 19808461-19822755 | 18.3651 | 28.4507 | 1.549171 | 2.00674 |
| Flot1 | chr17: 35823356-35832787 | 26.4843 | 41.1893 | 1.555233 | 2.06612 |
| Cldn25 | chr16: 58727909-58734247 | 21.5502 | 33.6494 | 1.561441 | 2.03186 |
| Ctsd | chr7: 142375915-142387870 | 117.559 | 184.481 | 1.569264 | 2.24616 |
| Myo5a | chr9: 75071205-75223687 | 5.68235 | 8.94302 | 1.573824 | 2.17027 |
| Bag2 | chr1: 33745483-33757750 | 9.02784 | 14.2099 | 1.574007 | 1.86395 |
| Kif1b | chr4: 149176320-149307698 | 4.85228 | 7.63767 | 1.574037 | 2.01582 |
| Mctp2 | chr7: 72077829-72306595 | 4.11933 | 6.48469 | 1.574212 | 1.91323 |
| Zfp608 | chr18: 54888044-54990180 | 3.87891 | 6.11051 | 1.575314 | 1.86375 |
| Dusp5 | chr19: 53529317-53541322 | 31.3183 | 49.34 | 1.575436 | 2.2228 |
| Itgb1 | chr8: 128685653-128733579 | 42.854 | 68.1988 | 1.59142 | 2.29666 |
| Inppl1 | chr7: 101818312-101838226 | 4.74242 | 7.55018 | 1.592051 | 1.79668 |
| Capn2 | chr1: 182467258-182517483 | 30.9555 | 49.5738 | 1.601455 | 2.1841 |
| Ly6c2 | chr15: 75108160-75111949 | 175.294 | 281.427 | 1.605457 | 2.86289 |
| Rgs2 | chr1: 143999337-144004149 | 8.68437 | 13.9715 | 1.60881 | 1.97598 |
| Rnh1 | chr7: 141160325-141172851 | 76.8756 | 124.114 | 1.614474 | 2.13301 |
| Fhl2 | chr1: 43123073-43163961 | 12.9542 | 21.0138 | 1.62216 | 2.16361 |
| Dmwd | chr7: 19076199-19082775 | 6.56466 | 10.6501 | 1.622334 | 1.86217 |
| Farp1 | chr14: 121035573-121283726 | 3.96594 | 6.44394 | 1.62482 | 1.91341 |
| Slc39a14 | chr14: 70303466-70351424 | 9.56639 | 15.5549 | 1.625994 | 2.23651 |
| P4ha2 | chr11: 54100923-54131667 | 8.39933 | 13.6795 | 1.628638 | 1.61648 |
| Tspan3 | chr9: 56135883-56161070 | 26.2001 | 42.7128 | 1.630254 | 2.56607 |
| Osgin2 | chr4: 15997120-16013877 | 9.09216 | 14.8275 | 1.630797 | 2.27681 |
| Mt1 | chr8: 94179088-94180327 | 401.703 | 655.694 | 1.632287 | 3.2458 |

TABLE 3-continued

Genes differentially expressed in activated Ezh2−/− CD8 T cells versus WT CD8 T cells (fold changes >1.5, or <1.5)

| Gstt1 | chr10: 75783812-75798584 | 13.7323 | 22.4645 | 1.635891 | 2.14778 |
|---|---|---|---|---|---|
| Pcyt1a | chr16: 32430920-32475065 | 11.6551 | 19.0817 | 1.637193 | 2.25729 |
| Cobll1 | chr2: 65088338-65238626 | 3.5294 | 5.77861 | 1.637281 | 1.92477 |
| Tec | chr5: 72755722-72868448 | 5.84722 | 9.60695 | 1.642995 | 1.84149 |
| Ero1lb | chr13: 12565882-12609528 | 3.38798 | 5.58087 | 1.647255 | 2.06642 |
| Klrc1 | chr6: 129674858-129678910 | 41.034 | 68.0485 | 1.658343 | 1.93116 |
| Cdc14b | chr13: 64192544-64274988 | 5.1598 | 8.56258 | 1.65948 | 2.22247 |
| Nln | chr13: 104023438-104109614 | 5.61253 | 9.33047 | 1.662437 | 2.19714 |
| Trerf1 | chr17: 47140941-47359458 | 3.30264 | 5.50909 | 1.668086 | 1.78906 |
| Sdf2l1 | chr16: 17130137-17132383 | 54.0271 | 90.2748 | 1.670916 | 2.7347 |
| Fkbp5 | chr17: 28399094-28486112 | 46.564 | 77.9946 | 1.674996 | 2.42306 |
| Osbpl3 | chr6: 50293326-50456170 | 9.22649 | 15.4632 | 1.675958 | 2.31895 |
| Fam129a | chr1: 151571372-151719347 | 11.9485 | 20.0435 | 1.677484 | 2.31551 |
| Gucy1a3 | chr3: 82092426-82145877 | 5.15219 | 8.66426 | 1.681666 | 2.17677 |
| Plxnd1 | chr6: 115954810-115995005 | 3.41602 | 5.74903 | 1.682961 | 2.11943 |
| Dennd1b | chr1: 138963708-139176042 | 4.82567 | 8.13485 | 1.685745 | 2.44437 |
| Ube2e3 | chr2: 78869046-78920583 | 19.0113 | 32.1628 | 1.691773 | 2.54713 |
| Chst12 | chr5: 140505608-140525238 | 21.0791 | 35.6835 | 1.692832 | 2.40647 |
| Srgap3 | chr6: 112717971-112947266 | 6.89024 | 11.7104 | 1.699557 | 2.12556 |
| Ctnna1 | chr18: 35118911-35254775 | 25.4877 | 43.3358 | 1.700263 | 2.52378 |
| Gmds | chr13: 31819585-32338544 | 14.4159 | 24.5238 | 1.70116 | 2.38696 |
| Nme4 | chr17: 26091744-26095470 | 10.8593 | 18.4947 | 1.703118 | 2.19529 |
| Nphp1 | chr2: 127740731-127788854 | 3.42866 | 5.88637 | 1.716817 | 1.86883 |
| Abcd3 | chr3: 121758909-121815215 | 12.8811 | 22.1511 | 1.719663 | 2.73416 |
| Fam20a | chr11: 109672925-109722256 | 7.38744 | 12.7349 | 1.723862 | 2.18714 |
| Scmh1 | chr4: 120405280-120530199 | 4.34688 | 7.51418 | 1.728636 | 2.03556 |
| Atp2b4 | chr1: 133702673-133753747 | 9.55719 | 16.5449 | 1.731146 | 2.52369 |
| Mt2 | chr8: 94172617-94173567 | 284.062 | 493.773 | 1.738258 | 3.82003 |
| Cdr2 | chr7: 120957036-120982312 | 5.34904 | 9.30363 | 1.73931 | 2.09423 |
| Dgat1 | chr15: 76502014-76511818 | 24.8378 | 43.3427 | 1.745025 | 2.59877 |
| Sec24d | chr3: 123267495-123365636 | 5.62744 | 9.82327 | 1.745602 | 2.35207 |
| Batf | chr12: 85686719-85709087 | 26.2455 | 45.8874 | 1.748389 | 2.71379 |
| Adk | chr14: 21052573-21448569 | 17.2605 | 30.249 | 1.752495 | 2.4386 |
| Ctsl | chr13: 64363213-64370306 | 3.74523 | 6.56525 | 1.752966 | 2.06795 |
| Podnl1 | chr8: 84125988-84132517 | 7.44807 | 13.092 | 1.757777 | 2.20742 |
| Slc16a13 | chr11: 70216791-70220994 | 3.89426 | 6.85213 | 1.759548 | 2.12616 |
| Fasl | chr1: 161780691-161788495 | 12.7103 | 22.4564 | 1.766782 | 2.34342 |
| Gnb5 | chr9: 75306287-75345923 | 4.27864 | 7.57499 | 1.77042 | 1.89903 |

TABLE 3-continued

Genes differentially expressed in activated Ezh2−/− CD8 T cells versus WT CD8 T cells (fold changes >1.5, or <1.5)

| | | | | | |
|---|---|---|---|---|---|
| Athl1 | chr7: 140941580-140947658 | 7.00262 | 12.4098 | 1.77217 | 2.41241 |
| Cd9 | chr6: 125460265-125494755 | 32.1545 | 57.1001 | 1.775806 | 3.11526 |
| Kctd11 | chr11: 69878263-69880985 | 3.43969 | 6.11343 | 1.777322 | 2.06033 |
| Irf5 | chr6: 29526624-29537320 | 4.64554 | 8.25699 | 1.777403 | 1.81066 |
| Nedd9 | chr13: 41309915-41487320 | 20.6483 | 36.8256 | 1.78347 | 2.63725 |
| Reep1 | chr6: 71707680-71810705 | 3.96192 | 7.06979 | 1.784437 | 2.36149 |
| Fgl2 | chr5: 21292960-21424677 | 10.0853 | 17.9972 | 1.784495 | 2.46158 |
| Arhgef25 | chr10: 127182520-127190054 | 5.36294 | 9.5744 | 1.785289 | 1.8832 |
| Prkd3 | chr17: 78949404-79020816 | 8.73737 | 15.6359 | 1.789543 | 2.73523 |
| Sypl | chr12: 32953944-32979502 | 5.09911 | 9.14031 | 1.79253 | 2.76305 |
| Ggt1 | chr10: 75573592-75586182 | 3.46413 | 6.21196 | 1.793226 | 1.98981 |
| Jdp2 | chr12: 85599104-85639878 | 4.22403 | 7.58506 | 1.795693 | 1.72542 |
| Neb | chr2: 52136646-52338798 | 3.46746 | 6.25304 | 1.803348 | 2.34709 |
| Fah | chr7: 84585158-84605942 | 6.24535 | 11.2867 | 1.80721 | 2.17012 |
| Cltb | chr13: 54592938-54611272 | 9.89955 | 17.918 | 1.809987 | 2.43277 |
| Snx10 | chr6: 51523902-51590670 | 5.91387 | 10.7138 | 1.811633 | 2.26874 |
| Tgm2 | chr2: 158116404-158146392 | 13.6661 | 24.8797 | 1.820544 | 2.47071 |
| Galnt10 | chr11: 57645441-57787500 | 3.04644 | 5.56587 | 1.827011 | 2.22321 |
| Tmem180 | chr19: 46356879-46375254 | 6.36308 | 11.6708 | 1.834145 | 2.47292 |
| Raph1 | chr1: 60483184-60566765 | 4.88375 | 8.98028 | 1.838808 | 2.81761 |
| Itga5 | chr15: 103344285-103366748 | 2.84999 | 5.25693 | 1.844545 | 2.24877 |
| Ckb | chr12: 111669354-111672338 | 20.5296 | 37.8886 | 1.845559 | 2.70664 |
| Emp1 | chr6: 135362930-135383173 | 11.2888 | 20.8748 | 1.849148 | 2.47666 |
| Hopx | chr5: 77086985-77115123 | 39.6767 | 73.3719 | 1.849243 | 2.76993 |
| Gsn | chr2: 35256358-35307902 | 23.3956 | 43.2951 | 1.850568 | 2.40042 |
| Erc1 | chr6: 119570795-119848150 | 2.91537 | 5.39742 | 1.85137 | 2.4224 |
| Gsto1 | chr19: 47854988-47864788 | 22.0163 | 40.8322 | 1.854635 | 3.04207 |
| Spry2 | chr14: 105891946-105896819 | 3.37564 | 6.27895 | 1.860078 | 2.18273 |
| Tspan6 | chrX: 133891069-133898429 | 3.55596 | 6.63057 | 1.864637 | 2.3644 |
| Rhob | chr12: 8497758-8499985 | 3.89781 | 7.28695 | 1.869501 | 2.30729 |
| Klhl5 | chr5: 65131230-65168142 | 7.58729 | 14.2097 | 1.872835 | 2.82009 |
| Slc16a10 | chr10: 40033534-40142254 | 7.36569 | 13.8214 | 1.876462 | 2.56802 |
| Gpr160 | chr3: 30855949-30897192 | 3.07493 | 5.77041 | 1.876596 | 1.90069 |
| 0610010F05Rik | chr11: 23573775-23633631 | 4.69774 | 8.84359 | 1.882522 | 2.78239 |
| Gcat | chr15: 79030873-79043558 | 11.8834 | 22.5486 | 1.897487 | 2.59256 |
| Tubb6 | chr18: 67390730-67402749 | 54.1231 | 102.735 | 1.89817 | 3.05572 |
| Kctd17 | chr15: 78428627-78439303 | 9.4774 | 18.0029 | 1.899564 | 2.6571 |
| Dstn | chr2: 143915330-143943324 | 16.3477 | 31.1156 | 1.903362 | 3.22736 |

TABLE 3-continued

Genes differentially expressed in activated Ezh2−/− CD8 T cells versus WT CD8 T cells (fold changes >1.5, or <1.5)

| Gene | Location | | | | |
|---|---|---|---|---|---|
| Skap2 | chr6: 51859164-52012549 | 8.21398 | 15.6473 | 1.904963 | 2.66026 |
| Ncs1 | chr2: 31245922-31295471 | 4.20489 | 8.03434 | 1.910713 | 2.62995 |
| Lysmd2 | chr9: 75625731-75637773 | 3.75403 | 7.22399 | 1.924331 | 2.2162 |
| Lgalsl | chr11: 20823354-20831108 | 3.88908 | 7.49705 | 1.927718 | 2.71928 |
| Axl | chr7: 25756499-25788733 | 8.22942 | 15.8814 | 1.929826 | 2.60229 |
| Ppfibp1 | chr6: 146888493-147032023 | 4.84964 | 9.36894 | 1.931886 | 2.66045 |
| Ctla2b | chr13: 60895350-60897447 | 9.89059 | 19.1807 | 1.939289 | 2.17814 |
| Nek6 | chr2: 38511696-38587490 | 14.4253 | 28.0404 | 1.943831 | 2.96254 |
| Dusp14 | chr11: 84048044-84068357 | 3.08742 | 6.02014 | 1.949892 | 2.18121 |
| Rab11fip4 | chr11: 79591211-79694012 | 3.41157 | 6.65258 | 1.950008 | 2.30509 |
| Ier3 | chr17: 35821712-35822911 | 23.0807 | 45.1091 | 1.954411 | 3.36098 |
| Ggt7 | chr2: 155490379-155514846 | 5.73512 | 11.231 | 1.958287 | 2.66498 |
| Abhd5 | chr9: 122351615-122381523 | 3.17359 | 6.27814 | 1.978245 | 2.61134 |
| Rnf130 | chr11: 50025330-50104733 | 16.8571 | 33.351 | 1.978452 | 2.84692 |
| Lilrb4 | chr10: 51490974-51496611 | 3.9617 | 7.87077 | 1.986716 | 2.32171 |
| Lama5 | chr2: 180176372-180225859 | 3.14139 | 6.26056 | 1.99293 | 2.95964 |
| Prnp | chr2: 131909927-131938431 | 9.33462 | 18.7267 | 2.006151 | 2.95325 |
| Pmaip1 | chr18: 66458603-66465558 | 9.0896 | 18.3585 | 2.019727 | 3.25256 |
| Cd44 | chr2: 102811141-102901665 | 32.2371 | 65.1427 | 2.020735 | 3.4343 |
| Ptpn3 | chr4: 57190840-57301837 | 2.97575 | 6.0319 | 2.02702 | 2.9043 |
| Serpinb9 | chr13: 33004540-33017955 | 52.562 | 106.615 | 2.028369 | 3.4584 |
| Prkar2b | chr12: 31958478-32061279 | 3.10405 | 6.29692 | 2.028608 | 2.64764 |
| Tsc22d1 | chr14: 76415820-76507766 | 2.47839 | 5.04549 | 2.035792 | 1.92602 |
| Pdgfb | chr15: 79995875-80014808 | 2.71451 | 5.53332 | 2.038432 | 2.45448 |
| Tubb2a | chr13: 34074279-34078008 | 13.6877 | 27.996 | 2.045339 | 3.04204 |
| 6720401G13Rik | chrX: 50555743-50635258 | 4.51046 | 9.22918 | 2.046176 | 2.83062 |
| Ptpla | chr2: 14026830-14056035 | 8.72474 | 17.8607 | 2.047126 | 2.35883 |
| Tnfsf11 | chr14: 78277445-78308043 | 8.11518 | 16.8125 | 2.071736 | 3.25459 |
| Tnfsf4 | chr1: 161395437-161418206 | 4.88034 | 10.1126 | 2.072124 | 2.70347 |
| H1f0 | chr15: 79028211-79030500 | 27.4108 | 57.1683 | 2.085611 | 3.47033 |
| Slc25a33 | chr4: 149744035-149774267 | 4.23268 | 8.83904 | 2.088287 | 2.76013 |
| Rhoc | chr3: 104789033-104794459 | 6.01402 | 12.5725 | 2.090532 | 2.6907 |
| Hip1 | chr5: 135406518-135545122 | 3.63899 | 7.60892 | 2.090938 | 3.12878 |
| Tdrkh | chr3: 94413317-94431499 | 3.66323 | 7.70964 | 2.104606 | 2.76504 |
| Tmbim1 | chr1: 74285033-74353692 | 6.18107 | 13.2187 | 2.138575 | 2.40472 |
| Napsa | chr7: 44572444-44586846 | 6.02195 | 12.8995 | 2.142091 | 2.90148 |
| Cyfip1 | chr7: 55842070-55962493 | 2.66988 | 5.72558 | 2.144498 | 2.13651 |
| Hmox1 | chr8: 75093617-75100593 | 4.77482 | 10.2442 | 2.145464 | 2.72707 |

TABLE 3-continued

Genes differentially expressed in activated Ezh2-/- CD8 T cells versus WT CD8 T cells (fold changes >1.5, or <1.5)

| | | | | | |
|---|---|---|---|---|---|
| Pros1 | chr16: 62854333-62929340 | 5.06057 | 10.8608 | 2.146149 | 3.13083 |
| Serpinb6a | chr13: 33917917-34002794 | 42.5435 | 91.3699 | 2.147681 | 3.40426 |
| Trim16 | chr11: 62820252-62842948 | 2.48985 | 5.37266 | 2.157828 | 2.69273 |
| Luzp1 | chr4: 136469760-136549318 | 2.93924 | 6.34363 | 2.158262 | 3.21933 |
| Fam213a | chr14: 40993739-41013775 | 8.78798 | 19.0233 | 2.164689 | 3.14175 |
| Ccbl2 | chr3: 142701079-142744910 | 3.04393 | 6.59984 | 2.168188 | 2.78194 |
| Smo | chr6: 29735496-29761366 | 3.31696 | 7.22013 | 2.176726 | 2.93639 |
| Spire1 | chr18: 67488208-67552721 | 3.00329 | 6.56944 | 2.18742 | 3.02716 |
| Sccpdh | chr1: 179668230-179687184 | 4.26003 | 9.4297 | 2.213532 | 2.90094 |
| Scamp1 | chr13: 94201432-94285281 | 3.23738 | 7.19263 | 2.22174 | 3.33055 |
| Adap1 | chr5: 139271875-139325464 | 10.9558 | 25.0504 | 2.286483 | 3.61951 |
| Bmi1 | chr2: 18677017-18686629 | 16.0747 | 36.7897 | 2.288671 | 4.33961 |
| Snx8 | chr5: 140340302-140389247 | 2.29558 | 5.27979 | 2.299978 | 2.79324 |
| Cenpv | chr11: 62524943-62539261 | 11.6688 | 26.8611 | 2.301956 | 3.5057 |
| Erdr1 | chrY: 90785441-90816465 | 92.797 | 214.099 | 2.307179 | 4.91218 |
| Eomes | chr9: 118478188-118486132 | 12.6459 | 29.2546 | 2.31336 | 3.2629 |
| Errfi1 | chr4: 150855090-150868880 | 5.01439 | 11.6143 | 2.3162 | 3.51602 |
| Hbegf | chr18: 36504926-36515805 | 3.49191 | 8.1076 | 2.321826 | 3.06217 |
| Serpinf1 | chr11: 75410028-75422623 | 6.42015 | 14.9286 | 2.325273 | 2.89742 |
| Abcg2 | chr6: 58596671-58692451 | 3.44092 | 8.05489 | 2.340911 | 3.29539 |
| Dapk2 | chr9: 66158225-66272242 | 3.02041 | 7.09597 | 2.349347 | 2.65609 |
| Spp1 | chr5: 104435110-104441053 | 28.8109 | 67.7179 | 2.350422 | 3.56009 |
| H2-Aa | chr17: 34282750-34287771 | 2.77585 | 6.59137 | 2.374543 | 2.80979 |
| Tmem40 | chr6: 115729136-115762466 | 2.31488 | 5.53297 | 2.390181 | 2.1129 |
| Ccl4 | chr11: 83662583-83664683 | 258.104 | 619.718 | 2.401041 | 4.71837 |
| Swap70 | chr7: 110221702-110283506 | 3.05215 | 7.35261 | 2.408993 | 3.37302 |
| Ifng | chr10: 118441046-118445892 | 319.393 | 772.319 | 2.418077 | 3.90623 |
| Scn1b | chr7: 31116523-31126945 | 2.34019 | 5.67268 | 2.424034 | 2.66519 |
| Apobr | chr7: 126585007-126589092 | 2.30775 | 5.59461 | 2.424269 | 2.88247 |
| Emilin2 | chr17: 71252175-71310965 | 8.50577 | 20.6249 | 2.424807 | 3.78357 |
| Vcl | chr14: 20929432-21033673 | 4.16254 | 10.2982 | 2.474025 | 3.87046 |
| Sgk1 | chr10: 21882183-21999902 | 3.73584 | 9.25241 | 2.476667 | 3.26218 |
| Tjp2 | chr19: 24094501-24225026 | 2.21591 | 5.49655 | 2.480498 | 3.06618 |
| Arsb | chr13: 93771678-93943016 | 9.48056 | 23.6322 | 2.492701 | 4.32173 |
| Dennd3 | chr15: 73512559-73572242 | 2.03118 | 5.10603 | 2.513818 | 3.2672 |
| Fam129b | chr2: 32876133-32961255 | 2.53589 | 6.37845 | 2.515264 | 2.09404 |
| Ceacam1 | chr7: 25376818-25566417 | 2.55418 | 6.554 | 2.565998 | 2.36757 |
| Itga3 | chr11: 95044481-95076714 | 2.46548 | 6.37386 | 2.585243 | 3.22523 |

TABLE 3-continued

Genes differentially expressed in activated Ezh2−/− CD8 T cells versus WT CD8 T cells (fold changes >1.5, or <1.5)

| Ccl3 | chr11: 83647842-83649378 | 250.512 | 648.893 | 2.590266 | 4.50365 |
|---|---|---|---|---|---|
| Stard10 | chr7: 101321318-101346312 | 8.47423 | 22.0998 | 2.607885 | 3.83894 |
| Entpd1 | chr19: 40659793-40741602 | 2.01219 | 5.24984 | 2.609024 | 3.56895 |
| Mid1 | chrX: 169685246-169990797 | 4.12376 | 11.1887 | 2.713227 | 3.54394 |
| Efemp2 | chr19: 5474689-5481854 | 1.84258 | 5.02967 | 2.729695 | 2.63386 |
| Prdm1 | chr10: 44437174-44458687 | 2.77051 | 7.57763 | 2.735093 | 3.85459 |
| Csrp2 | chr10: 110920175-110939514 | 5.68316 | 15.5727 | 2.740141 | 3.76563 |
| Spats2 | chr15: 99126844-99212466 | 3.53571 | 9.77594 | 2.764924 | 3.58286 |
| Myo1e | chr9: 70207349-70400067 | 3.82537 | 10.6416 | 2.781841 | 3.78239 |
| Ift43 | chr12: 86082560-86162459 | 2.65717 | 7.43115 | 2.796631 | 2.2847 |
| Nrgn | chr9: 37544492-37552745 | 24.104 | 68.0857 | 2.824665 | 4.88461 |
| Pctp | chr11: 89983416-90002894 | 2.61247 | 7.39146 | 2.82929 | 3.50806 |
| Bag3 | chr7: 128523582-128546979 | 2.07973 | 5.9825 | 2.876571 | 3.4665 |
| Ryk | chr9: 102834919-102908307 | 2.46276 | 7.18477 | 2.917373 | 3.71111 |
| Gadd45g | chr13: 51846674-51848474 | 43.4029 | 127.932 | 2.947537 | 5.39775 |
| Smpdl3b | chr4: 132732965-132757171 | 2.90604 | 8.70416 | 2.995195 | 3.80438 |
| Adam8 | chr7: 139978940-139992488 | 12.9773 | 40.2267 | 3.099767 | 4.76905 |
| Runx2 | chr17: 44495986-45119284 | 4.34811 | 13.7306 | 3.157822 | 4.1811 |
| Cth | chr3: 157894247-157925063 | 3.07432 | 9.73245 | 3.165712 | 3.96382 |
| Id2 | chr12: 25093798-25096092 | 63.0066 | 199.93 | 3.173159 | 6.50736 |
| Tnfsf10 | chr3: 27317076-27339665 | 6.94075 | 22.1575 | 3.192375 | 5.38444 |
| Cxcr6 | chr9: 123789509-123851899 | 12.1359 | 38.9543 | 3.209837 | 2.54777 |
| Crabp2 | chr3: 87948692-87953372 | 18.0116 | 58.0143 | 3.220958 | 5.01067 |
| S100a6 | chr3: 90612893-90614414 | 53.0816 | 171.446 | 3.229856 | 6.65053 |
| Map6 | chr7: 99267446-99337137 | 3.46948 | 11.3069 | 3.258956 | 3.74398 |
| Pde8a | chr7: 81213803-81333622 | 2.17636 | 7.18374 | 3.30081 | 4.14457 |
| Ell2 | chr13: 75707483-75772358 | 2.77676 | 9.19774 | 3.312407 | 4.56307 |
| Srxn1 | chr2: 152105523-152111376 | 3.31915 | 11.0287 | 3.322755 | 3.8982 |
| Ccl5 | chr11: 83525778-83530518 | 52.4865 | 175.015 | 3.334499 | 7.56866 |
| Gpx7 | chr4: 108400216-108406713 | 1.83837 | 6.17318 | 3.357972 | 3.65413 |
| Selp | chr1: 164115263-164220274 | 1.59363 | 5.49058 | 3.445325 | 3.78354 |
| Myo10 | chr15: 25622549-25813671 | 3.53444 | 12.468 | 3.527583 | 4.69374 |
| Ckap4 | chr10: 84526304-84533888 | 1.71625 | 6.08647 | 3.546362 | 4.19768 |
| Ifitm2 | chr7: 140954838-140955961 | 42.7743 | 157.797 | 3.689052 | 7.61179 |
| Ccr5 | chr9: 124121542-124127183 | 10.2945 | 38.3143 | 3.721799 | 6.30623 |
| Prf1 | chr10: 61297835-61304263 | 129.906 | 487.964 | 3.756294 | 5.05892 |
| Igf2bp3 | chr6: 49085217-49214954 | 1.44062 | 5.52608 | 3.835913 | 4.75033 |
| Lgals3 | chr14: 47373859-47386167 | 75.3478 | 315.005 | 4.180687 | 6.38291 |

TABLE 3-continued

Genes differentially expressed in activated Ezh2−/− CD8 T cells versus WT CD8 T cells (fold changes >1.5, or <1.5)

| Ttc39c | chr18: 12643532-12737052 | 4.70147 | 19.7382 | 4.198314 | 5.03647 |
|---|---|---|---|---|---|
| Il3 | chr11: 54265084-54267279 | 2.13122 | 9.11579 | 4.277269 | 4.12395 |
| AA467197 | chr2: 122637886-122641076 | 43.8157 | 187.769 | 4.28543 | 5.90123 |
| Myh10 | chr11: 68691914-68816624 | 1.33851 | 5.79402 | 4.328689 | 4.63453 |
| Lad1 | chr1: 135818597-135833341 | 2.48991 | 10.8046 | 4.339353 | 4.91941 |
| Havcr2 | chr11: 46454930-46481254 | 3.76472 | 16.4422 | 4.367446 | 5.43393 |
| Lat2 | chr5: 134600264-134615023 | 2.01795 | 8.81871 | 4.370142 | 3.94515 |
| S100a4 | chr3: 90603769-90606045 | 15.9347 | 70.0231 | 4.394381 | 7.73292 |
| H2-Q10 | chr17: 35470088-35474563 | 5.10764 | 22.8331 | 4.470388 | 5.02038 |
| Upp1 | chr11: 9118007-9136170 | 6.48824 | 29.5207 | 4.549885 | 4.74157 |
| Calcb | chr7: 114718642-114723365 | 1.38498 | 6.36413 | 4.59508 | 4.20872 |
| Plcg2 | chr8: 117498290-117635142 | 1.38826 | 6.43605 | 4.636062 | 5.16012 |
| Lmna | chr3: 88481148-88503332 | 2.43471 | 11.3255 | 4.651706 | 3.65595 |
| Chit1 | chr1: 134111241-134151436 | 2.06936 | 9.94087 | 4.803846 | 4.80329 |
| Tmem37 | chr1: 120067376-120073780 | 1.09256 | 5.25542 | 4.810177 | 4.38566 |
| Sytl2 | chr7: 90348698-90410439 | 2.39279 | 11.8286 | 4.943422 | 5.52709 |
| Adamts14 | chr10: 61197111-61273438 | 2.55895 | 12.7494 | 4.982293 | 5.50909 |
| Chst11 | chr10: 82985496-83195891 | 2.64222 | 13.6239 | 5.156242 | 6.61072 |
| Gem | chr4: 11704446-11714993 | 12.2011 | 63.3889 | 5.195311 | 7.51212 |
| 2900026A02Rik | chr5: 113086322-113163313 | 1.03929 | 5.54978 | 5.339964 | 5.76562 |
| Csf2 | chr11: 54247269-54249899 | 1.4989 | 8.15492 | 5.440616 | 4.47628 |
| Stk32c | chr7: 139103637-139242973 | 0.923139 | 5.11068 | 5.536177 | 3.54504 |
| Batf3 | chr1: 191098413-191108943 | 8.84974 | 49.3933 | 5.581334 | 6.33029 |
| Mt3 | chr8: 94152606-94154148 | 5.90125 | 33.4046 | 5.66058 | 7.17418 |
| Serpine2 | chr1: 79794320-79858665 | 17.4602 | 100.586 | 5.760883 | 7.8606 |
| Prr5 | chr15: 84680997-84703673 | 0.961404 | 5.67609 | 5.903948 | 5.05891 |
| Rgs8 | chr1: 153653036-153697665 | 0.929534 | 5.6 | 6.024535 | 5.69151 |
| Gatm | chr2: 122594472-122611277 | 1.27825 | 8.34666 | 6.52976 | 6.05789 |
| Ccl1 | chr11: 82176665-82179812 | 7.40731 | 49.7403 | 6.715012 | 7.98813 |
| Slc16a11 | chr11: 70213909-70216414 | 2.07066 | 15.4949 | 7.483069 | 6.61717 |
| Cd63 | chr10: 128908918-128912818 | 2.23541 | 17.0974 | 7.648464 | 5.0973 |
| Ifitm3 | chr7: 141009589-141010744 | 8.69548 | 67.1853 | 7.726473 | 9.25523 |
| Fkbp11 | chr15: 98724367-98728198 | 1.87125 | 14.6648 | 7.836883 | 6.22162 |
| Tmem163 | chr1: 127490341-127678021 | 1.38221 | 10.9741 | 7.93951 | 6.62558 |
| Prkcdbp | chr7: 105480615-105482197 | 2.57694 | 20.9413 | 8.12642 | 6.73589 |
| 2810025M15Rik | chr1: 157135182-157420236 | 0.697929 | 5.67704 | 8.134141 | 3.46419 |
| Nkain1 | chr4: 130530130-130574036 | 1.51265 | 13.0996 | 8.660018 | 6.81582 |
| Lrrk1 | chr7: 66258746-66388341 | 0.841171 | 8.08538 | 9.612022 | 7.89001 |

TABLE 3-continued

Genes differentially expressed in activated Ezh2−/− CD8 T cells versus WT CD8 T cells (fold changes >1.5, or <1.5)

| | | | | | |
|---|---|---|---|---|---|
| Sdc1 | chr12: 8771395-8793687 | 1.27189 | 13.3531 | 10.49864 | 7.19758 |
| Il10 | chr1: 131019844-131024970 | 0.755523 | 8.36882 | 11.07688 | 5.99925 |
| Tnfrsf8 | chr4: 145268975-145315147 | 1.78896 | 27.1958 | 15.20201 | 8.54566 |
| Gzmk | chr13: 113171873-113180897 | 0.394432 | 6.43821 | 16.32272 | 6.4391 |
| Ccl9 | chr11: 83572916-83578636 | 0.756583 | 12.8457 | 16.97853 | 9.37958 |
| Ccr2 | chr9: 124102182-124109140 | 0.711057 | 12.307 | 17.30803 | 9.08693 |
| Serpinb9b | chr13: 33027413-33040558 | 0.831403 | 15.3289 | 18.43749 | 7.82488 |
| Ifitm1 | chr7: 140967428-140969827 | 6.39798 | 143.439 | 22.41947 | 9.64438 |
| Filip1 | chr9: 79815561-79977882 | 0.418097 | 10.0961 | 24.14764 | 7.77259 |
| Atp6v0d2 | chr4: 19876837-19922566 | 0.174812 | 5.8094 | 33.23243 | 7.88156 |
| Cdkn2a | chr4: 89274472-89294619 | 0.468105 | 15.6505 | 33.43367 | 6.32084 |
| Gzmc | chr14: 56231400-56234656 | 6.07045 | 390.705 | 64.36168 | 15.6087 |
| Gzma | chr13: 113093826-113100981 | 1.86409 | 172.475 | 92.52556 | 15.2708 |
| Gzme | chr14: 56117618-56120625 | 0.114213 | 13.2098 | 115.6587 | 7.10335 |
| Gzmd | chr14: 56129567-56132593 | 0.098476 | 14.4692 | 146.9305 | 6.60812 |
| Mir1199 | chr8: 84011514-84011633 | 0 | 14.5971 | 1048576 | #NAME? |

| gene_id | status | p_value | q_value | significant | RNA_level |
|---|---|---|---|---|---|
| Xist | OK | 5.00E−05 | 0.000206 | yes | ok |
| Acvrl1 | OK | 5.00E−05 | 0.000206 | yes | ok |
| Dntt | OK | 5.00E−05 | 0.000206 | yes | ok |
| Tlr1 | OK | 5.00E−05 | 0.000206 | yes | ok |
| Ccdc164 | OK | 5.00E−05 | 0.000206 | yes | ok |
| Matk | OK | 5.00E−05 | 0.000206 | yes | ok |
| Tespa1 | OK | 5.00E−05 | 0.000206 | yes | ok |
| Dapl1 | OK | 5.00E−05 | 0.000206 | yes | ok |
| Id3 | OK | 5.00E−05 | 0.000206 | yes | ok |
| St6gal1 | OK | 5.00E−05 | 0.000206 | yes | ok |
| Cd101 | OK | 5.00E−05 | 0.000206 | yes | ok |
| Lst1 | OK | 0.00025 | 0.000925 | yes | ok |
| Fam183b | OK | 0.00045 | 0.001589 | yes | ok |
| Tbxa2r | OK | 5.00E−05 | 0.000206 | yes | ok |
| Ephx1 | OK | 5.00E−05 | 0.000206 | yes | ok |
| Igfbp4 | OK | 5.00E−05 | 0.000206 | yes | ok |
| Casp1 | OK | 0.00015 | 0.000577 | yes | ok |
| Cd226 | OK | 5.00E−05 | 0.000206 | yes | ok |
| Ifngr2 | OK | 0.0001 | 0.000396 | yes | ok |
| Amz2 | OK | 5.00E−05 | 0.000206 | yes | ok |
| Gbp10 | OK | 5.00E−05 | 0.000206 | yes | ok |
| Ifi203 | OK | 5.00E−05 | 0.000206 | yes | ok |
| Sh3bp5 | OK | 5.00E−05 | 0.000206 | yes | ok |
| Arl5c | OK | 5.00E−05 | 0.000206 | yes | ok |
| Trp53inp1 | OK | 5.00E−05 | 0.000206 | yes | ok |
| N4bp2l1 | OK | 5.00E−05 | 0.000206 | yes | ok |
| Slamf6 | OK | 5.00E−05 | 0.000206 | yes | ok |
| Abcg1 | OK | 5.00E−05 | 0.000206 | yes | ok |
| H2-Oa | OK | 0.0001 | 0.000396 | yes | ok |
| Synpo | OK | 5.00E−05 | 0.000206 | yes | ok |
| Iigp1 | OK | 5.00E−05 | 0.000206 | yes | ok |
| Smpdl3a | OK | 5.00E−05 | 0.000206 | yes | ok |
| Pbx4 | OK | 0.0005 | 0.001749 | yes | ok |
| 4930417O13Rik | OK | 0.0002 | 0.000753 | yes | ok |
| Arrdc3 | OK | 5.00E−05 | 0.000206 | yes | ok |
| A430093F15Rik | OK | 5.00E−05 | 0.000206 | yes | ok |
| Ltb | OK | 5.00E−05 | 0.000206 | yes | ok |
| Kdm6b | OK | 5.00E−05 | 0.000206 | yes | ok |
| Nr4a1 | OK | 5.00E−05 | 0.000206 | yes | ok |
| Igflr1 | OK | 5.00E−05 | 0.000206 | yes | ok |
| Bambi-ps1 | OK | 0.00215 | 0.006555 | yes | ok |
| Cd68 | OK | 0.0029 | 0.008584 | yes | ok |

TABLE 3-continued

Genes differentially expressed in activated Ezh2−/− CD8 T cells versus WT CD8 T cells (fold changes >1.5, or <1.5)

| Gene | Status | p-value | q-value | sig | status |
|---|---|---|---|---|---|
| Sytl1 | OK | 5.00E−05 | 0.000206 | yes | ok |
| Rasgef1a | OK | 0.00065 | 0.00222 | yes | ok |
| Ipcef1 | OK | 5.00E−05 | 0.000206 | yes | ok |
| Aldoc | OK | 5.00E−05 | 0.000206 | yes | ok |
| Mettl20 | OK | 0.00095 | 0.00313 | yes | ok |
| Pvr | OK | 5.00E−05 | 0.000206 | yes | ok |
| Btla | OK | 5.00E−05 | 0.000206 | yes | ok |
| Gm14446 | OK | 0.00025 | 0.000925 | yes | ok |
| I730030J21Rik | OK | 0.0005 | 0.001749 | yes | ok |
| Ccr7 | OK | 5.00E−05 | 0.000206 | yes | ok |
| Tox | OK | 5.00E−05 | 0.000206 | yes | ok |
| Pacsin1 | OK | 0.00015 | 0.000577 | yes | ok |
| Pecam1 | OK | 5.00E−05 | 0.000206 | yes | ok |
| 2610019F03Rik | OK | 0.0009 | 0.002983 | yes | ok |
| Tspan32 | OK | 5.00E−05 | 0.000206 | yes | ok |
| Slamf1 | OK | 0.0001 | 0.000396 | yes | ok |
| Ncf1 | OK | 5.00E−05 | 0.000206 | yes | ok |
| Chd3 | OK | 5.00E−05 | 0.000206 | yes | ok |
| A430107P09Rik | OK | 0.00065 | 0.00222 | yes | ok |
| Ccng2 | OK | 0.0001 | 0.000396 | yes | ok |
| Adamts6 | OK | 5.00E−05 | 0.000206 | yes | ok |
| Klf3 | OK | 0.00085 | 0.002831 | yes | ok |
| Sfn | OK | 0.00015 | 0.000577 | yes | ok |
| Fyb | OK | 5.00E−05 | 0.000206 | yes | ok |
| Bcl11b | OK | 5.00E−05 | 0.000206 | yes | ok |
| Arhgef18 | OK | 5.00E−05 | 0.000206 | yes | ok |
| Zfp36 | OK | 0.00015 | 0.000577 | yes | ok |
| Sertad3 | OK | 0.0014 | 0.004444 | yes | ok |
| P2ry10 | OK | 5.00E−05 | 0.000206 | yes | ok |
| Cpm | OK | 0.00065 | 0.00222 | yes | ok |
| Fut7 | OK | 0.0006 | 0.002064 | yes | ok |
| Serpine1 | OK | 0.00115 | 0.003718 | yes | ok |
| Slfn1 | OK | 5.00E−05 | 0.000206 | yes | ok |
| Per1 | OK | 0.0001 | 0.000396 | yes | ok |
| Trib3 | OK | 0.0006 | 0.002064 | yes | ok |
| Nr4a3 | OK | 0.00055 | 0.001907 | yes | ok |
| Tnfsf14 | OK | 0.0009 | 0.002983 | yes | ok |
| Slc35d3 | OK | 0.0032 | 0.009387 | yes | ok |
| Ddb2 | OK | 0.0024 | 0.007242 | yes | ok |
| Cbx4 | OK | 5.00E−05 | 0.000206 | yes | ok |
| Cdkn1b | OK | 5.00E−05 | 0.000206 | yes | ok |
| Gbp8 | OK | 0.0002 | 0.000753 | yes | ok |
| Irgm2 | OK | 0.00015 | 0.000577 | yes | ok |
| Il6st | OK | 0.0003 | 0.001095 | yes | ok |
| Hivep2 | OK | 0.0001 | 0.000396 | yes | ok |
| Slc43a2 | OK | 5.00E−05 | 0.000206 | yes | ok |
| Socs2 | OK | 0.00055 | 0.001907 | yes | ok |
| Rab37 | OK | 0.00215 | 0.006555 | yes | ok |
| Plcxd2 | OK | 0.00015 | 0.000577 | yes | ok |
| Abhd8 | OK | 0.0002 | 0.000753 | yes | ok |
| Rara | OK | 0.00015 | 0.000577 | yes | ok |
| H2-DMa | OK | 0.00015 | 0.000577 | yes | ok |
| Ms4a4c | OK | 0.00035 | 0.001262 | yes | ok |
| Klf2 | OK | 0.0005 | 0.001749 | yes | ok |
| Slc35g1 | OK | 0.0001 | 0.000396 | yes | ok |
| H2afv | OK | 0.0001 | 0.000396 | yes | ok |
| Dhx58 | OK | 0.001 | 0.003276 | yes | ok |
| Inadl | OK | 0.002 | 0.006139 | yes | ok |
| Orai2 | OK | 0.0003 | 0.001095 | yes | ok |
| Zfp36l1 | OK | 5.00E−05 | 0.000206 | yes | ok |
| Gbp6 | OK | 0.0003 | 0.001095 | yes | ok |
| Spry1 | OK | 0.00095 | 0.00313 | yes | ok |
| Syt11 | OK | 0.0008 | 0.002681 | yes | ok |
| Tgtp1 | OK | 0.00095 | 0.00313 | yes | ok |
| Tecpr1 | OK | 0.0001 | 0.000396 | yes | ok |
| A430078G23Rik | OK | 0.00145 | 0.004587 | yes | ok |
| Igtp | OK | 0.00035 | 0.001262 | yes | ok |
| Plekhg2 | OK | 0.0003 | 0.001095 | yes | ok |
| Itgb7 | OK | 0.0003 | 0.001095 | yes | ok |
| Cd2 | OK | 0.00025 | 0.000925 | yes | ok |
| Sh2b3 | OK | 0.0019 | 0.00586 | yes | ok |
| Folr4 | OK | 0.0002 | 0.000753 | yes | ok |
| Poldip3 | OK | 0.00065 | 0.00222 | yes | ok |
| Gprin3 | OK | 0.00185 | 0.005722 | yes | ok |
| Utrn | OK | 0.0002 | 0.000753 | yes | ok |
| Ifi27l2a | OK | 0.00115 | 0.003718 | yes | ok |
| Itga6 | OK | 0.00065 | 0.00222 | yes | ok |

TABLE 3-continued

Genes differentially expressed in activated Ezh2−/− CD8 T cells versus WT CD8 T cells (fold changes >1.5, or <1.5)

| | | | | | |
|---|---|---|---|---|---|
| Plcg1 | OK | 0.00035 | 0.001262 | yes | ok |
| Samhd1 | OK | 0.00095 | 0.00313 | yes | ok |
| Ing2 | OK | 0.00205 | 0.006278 | yes | ok |
| Mov10 | OK | 0.0006 | 0.002064 | yes | ok |
| Samd9l | OK | 0.0002 | 0.000753 | yes | ok |
| Lbh | OK | 0.00065 | 0.00222 | yes | ok |
| Setx | OK | 0.0008 | 0.002681 | yes | ok |
| Elk4 | OK | 0.001 | 0.003276 | yes | ok |
| BC021614 | OK | 0.00145 | 0.004587 | yes | ok |
| Gm8369 | OK | 0.00185 | 0.005722 | yes | ok |
| Fam189b | OK | 0.00125 | 0.00401 | yes | ok |
| Tpcn1 | OK | 0.0005 | 0.001749 | yes | ok |
| Ifi47 | OK | 0.00135 | 0.004299 | yes | ok |
| Ccdc64 | OK | 0.0009 | 0.002983 | yes | ok |
| Gbp2 | OK | 0.00195 | 0.005998 | yes | ok |
| Dlg4 | OK | 0.00135 | 0.004299 | yes | ok |
| Bzrap1 | OK | 0.00305 | 0.008984 | yes | ok |
| Rnf167 | OK | 0.00145 | 0.004587 | yes | ok |
| Kbtbd11 | OK | 0.001 | 0.003276 | yes | ok |
| Rab3ip | OK | 0.0022 | 0.006693 | yes | ok |
| Ikbke | OK | 0.00065 | 0.00222 | yes | ok |
| Fam117a | OK | 0.00255 | 0.007648 | yes | ok |
| Inpp4b | OK | 0.00065 | 0.00222 | yes | ok |
| Irf1 | OK | 0.0003 | 0.001095 | yes | ok |
| Lrig1 | OK | 0.00235 | 0.007104 | yes | ok |
| Rhoh | OK | 0.0004 | 0.001426 | yes | ok |
| Ift80 | OK | 0.001 | 0.003276 | yes | ok |
| Entpd5 | OK | 0.00095 | 0.00313 | yes | ok |
| Dpp4 | OK | 0.0007 | 0.002375 | yes | ok |
| Nfatc1 | OK | 0.00085 | 0.002831 | yes | ok |
| Pou2f2 | OK | 0.00225 | 0.006828 | yes | ok |
| Ndrg2 | OK | 0.0026 | 0.007782 | yes | ok |
| Tob2 | OK | 0.00115 | 0.003718 | yes | ok |
| Oas3 | OK | 0.0014 | 0.004444 | yes | ok |
| Pink1 | OK | 0.00265 | 0.007917 | yes | ok |
| Sbk1 | OK | 0.0031 | 0.009118 | yes | ok |
| Tap1 | OK | 0.0013 | 0.004153 | yes | ok |
| 2810474O19Rik | OK | 0.0012 | 0.003865 | yes | ok |
| Amica1 | OK | 0.00325 | 0.009517 | yes | ok |
| Gm12250 | OK | 0.0014 | 0.004444 | yes | ok |
| 1600014C10Rik | OK | 0.0016 | 0.005017 | yes | ok |
| Mib2 | OK | 0.0034 | 0.009909 | yes | ok |
| Irgm1 | OK | 0.00095 | 0.00313 | yes | ok |
| Ptpn18 | OK | 0.00205 | 0.006278 | yes | ok |
| Gbp9 | OK | 0.0013 | 0.004153 | yes | ok |
| Mndal | OK | 0.00095 | 0.00313 | yes | ok |
| 2410006H16Rik | OK | 0.0017 | 0.0053 | yes | ok |
| Map4k2 | OK | 0.00085 | 0.002831 | yes | ok |
| Slc17a9 | OK | 0.00305 | 0.008984 | yes | ok |
| Chd7 | OK | 0.0023 | 0.006967 | yes | ok |
| Agpat4 | OK | 0.00305 | 0.008984 | yes | ok |
| Pdia6 | OK | 0.00105 | 0.003422 | yes | ok |
| Slc25a24 | OK | 0.0017 | 0.0053 | yes | ok |
| Scd1 | OK | 0.00255 | 0.007648 | yes | ok |
| Smim3 | OK | 0.00305 | 0.008984 | yes | ok |
| Ptprj | OK | 0.00245 | 0.007377 | yes | ok |
| Gpr65 | OK | 0.0014 | 0.004444 | yes | ok |
| Ctla2a | OK | 0.0008 | 0.002681 | yes | ok |
| Phlpp1 | OK | 0.0032 | 0.009387 | yes | ok |
| Nabp1 | OK | 0.00045 | 0.001589 | yes | ok |
| Bcl3 | OK | 0.00145 | 0.004587 | yes | ok |
| Flot1 | OK | 0.001 | 0.003276 | yes | ok |
| Cldn25 | OK | 0.00075 | 0.002528 | yes | ok |
| Ctsd | OK | 0.00025 | 0.000925 | yes | ok |
| Myo5a | OK | 0.00015 | 0.000577 | yes | ok |
| Bag2 | OK | 0.0033 | 0.009647 | yes | ok |
| Kif1b | OK | 0.00065 | 0.00222 | yes | ok |
| Mctp2 | OK | 0.0024 | 0.007242 | yes | ok |
| Zfp608 | OK | 0.00195 | 0.005998 | yes | ok |
| Dusp5 | OK | 0.00185 | 0.005722 | yes | ok |
| Itgb1 | OK | 0.00015 | 0.000577 | yes | ok |
| Inppl1 | OK | 0.0016 | 0.005017 | yes | ok |
| Capn2 | OK | 0.00025 | 0.000925 | yes | ok |
| Ly6c2 | OK | 0.0005 | 0.001749 | yes | ok |
| Rgs2 | OK | 0.00225 | 0.006828 | yes | ok |
| Rnh1 | OK | 0.0003 | 0.001095 | yes | ok |
| Fhl2 | OK | 0.0013 | 0.004153 | yes | ok |

TABLE 3-continued

Genes differentially expressed in activated Ezh2−/− CD8 T cells
versus WT CD8 T cells (fold changes >1.5, or <1.5)

| Gene | | | | | |
|---|---|---|---|---|---|
| Dmwd | OK | 0.00255 | 0.007648 | yes | ok |
| Farp1 | OK | 0.00135 | 0.004299 | yes | ok |
| Slc39a14 | OK | 5.00E−05 | 0.000206 | yes | ok |
| P4ha2 | OK | 0.0026 | 0.007782 | yes | ok |
| Tspan3 | OK | 0.00025 | 0.000925 | yes | ok |
| Osgin2 | OK | 0.00085 | 0.002831 | yes | ok |
| Mt1 | OK | 0.00025 | 0.000925 | yes | ok |
| Gstt1 | OK | 0.0032 | 0.009387 | yes | ok |
| Pcyt1a | OK | 0.0001 | 0.000396 | yes | ok |
| Cobll1 | OK | 0.0007 | 0.002375 | yes | ok |
| Tec | OK | 0.0016 | 0.005017 | yes | ok |
| Ero1lb | OK | 0.00145 | 0.004587 | yes | ok |
| Klrc1 | OK | 0.0012 | 0.003865 | yes | ok |
| Cdc14b | OK | 0.0005 | 0.001749 | yes | ok |
| Nln | OK | 0.0005 | 0.001749 | yes | ok |
| Trerf1 | OK | 0.00095 | 0.00313 | yes | ok |
| Sdf2l1 | OK | 5.00E−05 | 0.000206 | yes | ok |
| Fkbp5 | OK | 0.0001 | 0.000396 | yes | ok |
| Osbpl3 | OK | 5.00E−05 | 0.000206 | yes | ok |
| Fam129a | OK | 5.00E−05 | 0.000206 | yes | ok |
| Gucy1a3 | OK | 0.00045 | 0.001589 | yes | ok |
| Plxnd1 | OK | 0.00035 | 0.001262 | yes | ok |
| Dennd1b | OK | 5.00E−05 | 0.000206 | yes | ok |
| Ube2e3 | OK | 0.0004 | 0.001426 | yes | ok |
| Chst12 | OK | 5.00E−05 | 0.000206 | yes | ok |
| Srgap3 | OK | 0.00015 | 0.000577 | yes | ok |
| Ctnna1 | OK | 5.00E−05 | 0.000206 | yes | ok |
| Gmds | OK | 0.00025 | 0.000925 | yes | ok |
| Nme4 | OK | 0.00255 | 0.007648 | yes | ok |
| Nphp1 | OK | 0.0019 | 0.00586 | yes | ok |
| Abcd3 | OK | 0.0001 | 0.000396 | yes | ok |
| Fam20a | OK | 0.0004 | 0.001426 | yes | ok |
| Scmh1 | OK | 0.0006 | 0.002064 | yes | ok |
| Atp2b4 | OK | 5.00E−05 | 0.000206 | yes | ok |
| Mt2 | OK | 5.00E−05 | 0.000206 | yes | ok |
| Cdr2 | OK | 0.0005 | 0.001749 | yes | ok |
| Dgat1 | OK | 5.00E−05 | 0.000206 | yes | ok |
| Sec24d | OK | 0.0001 | 0.000396 | yes | ok |
| Batf | OK | 0.00015 | 0.000577 | yes | ok |
| Adk | OK | 5.00E−05 | 0.000206 | yes | ok |
| Ctsl | OK | 0.0022 | 0.006693 | yes | ok |
| Podnl1 | OK | 0.0003 | 0.001095 | yes | ok |
| Slc16a13 | OK | 0.00115 | 0.003718 | yes | ok |
| Fasl | OK | 0.0001 | 0.000396 | yes | ok |
| Gnb5 | OK | 0.00145 | 0.004587 | yes | ok |
| Athl1 | OK | 0.0001 | 0.000396 | yes | ok |
| Cd9 | OK | 5.00E−05 | 0.000206 | yes | ok |
| Kctd11 | OK | 0.0013 | 0.004153 | yes | ok |
| Irf5 | OK | 0.001 | 0.003276 | yes | ok |
| Nedd9 | OK | 5.00E−05 | 0.000206 | yes | ok |
| Reep1 | OK | 0.0003 | 0.001095 | yes | ok |
| Fgl2 | OK | 0.0001 | 0.000396 | yes | ok |
| Arhgef25 | OK | 0.0006 | 0.002064 | yes | ok |
| Prkd3 | OK | 5.00E−05 | 0.000206 | yes | ok |
| Sypl | OK | 5.00E−05 | 0.000206 | yes | ok |
| Ggt1 | OK | 0.00255 | 0.007648 | yes | ok |
| Jdp2 | OK | 0.00215 | 0.006555 | yes | ok |
| Neb | OK | 5.00E−05 | 0.000206 | yes | ok |
| Fah | OK | 0.0006 | 0.002064 | yes | ok |
| Cltb | OK | 0.00015 | 0.000577 | yes | ok |
| Snx10 | OK | 0.0003 | 0.001095 | yes | ok |
| Tgm2 | OK | 5.00E−05 | 0.000206 | yes | ok |
| Galnt10 | OK | 0.0004 | 0.001426 | yes | ok |
| Tmem180 | OK | 0.00015 | 0.000577 | yes | ok |
| Raph1 | OK | 5.00E−05 | 0.000206 | yes | ok |
| Itga5 | OK | 0.00015 | 0.000577 | yes | ok |
| Ckb | OK | 5.00E−05 | 0.000206 | yes | ok |
| Emp1 | OK | 0.0006 | 0.002064 | yes | ok |
| Hopx | OK | 5.00E−05 | 0.000206 | yes | ok |
| Gsn | OK | 5.00E−05 | 0.000206 | yes | ok |
| Erc1 | OK | 5.00E−05 | 0.000206 | yes | ok |
| Gsto1 | OK | 5.00E−05 | 0.000206 | yes | ok |
| Spry2 | OK | 0.00125 | 0.00401 | yes | ok |
| Tspan6 | OK | 0.0017 | 0.0053 | yes | ok |
| Rhob | OK | 0.0003 | 0.001095 | yes | ok |
| Klhl5 | OK | 5.00E−05 | 0.000206 | yes | ok |
| Slc16a10 | OK | 5.00E−05 | 0.000206 | yes | ok |

TABLE 3-continued

Genes differentially expressed in activated Ezh2−/− CD8 T cells versus WT CD8 T cells (fold changes >1.5, or <1.5)

| Gene | | | | | |
|---|---|---|---|---|---|
| Gpr160 | OK | 0.0024 | 0.007242 | yes | ok |
| 0610010F05Rik | OK | 5.00E−05 | 0.000206 | yes | ok |
| Gcat | OK | 0.0001 | 0.000396 | yes | ok |
| Tubb6 | OK | 5.00E−05 | 0.000206 | yes | ok |
| Kctd17 | OK | 5.00E−05 | 0.000206 | yes | ok |
| Dstn | OK | 5.00E−05 | 0.000206 | yes | ok |
| Skap2 | OK | 0.00015 | 0.000577 | yes | ok |
| Ncs1 | OK | 5.00E−05 | 0.000206 | yes | ok |
| Lysmd2 | OK | 0.0012 | 0.003865 | yes | ok |
| Lgalsl | OK | 5.00E−05 | 0.000206 | yes | ok |
| Axl | OK | 5.00E−05 | 0.000206 | yes | ok |
| Ppfibp1 | OK | 5.00E−05 | 0.000206 | yes | ok |
| Ctla2b | OK | 0.00025 | 0.000925 | yes | ok |
| Nek6 | OK | 5.00E−05 | 0.000206 | yes | ok |
| Dusp14 | OK | 0.00175 | 0.005442 | yes | ok |
| Rab11fip4 | OK | 0.0001 | 0.000396 | yes | ok |
| Ier3 | OK | 5.00E−05 | 0.000206 | yes | ok |
| Ggt7 | OK | 5.00E−05 | 0.000206 | yes | ok |
| Abhd5 | OK | 5.00E−05 | 0.000206 | yes | ok |
| Rnf130 | OK | 5.00E−05 | 0.000206 | yes | ok |
| Lilrb4 | OK | 0.0007 | 0.002375 | yes | ok |
| Lama5 | OK | 5.00E−05 | 0.000206 | yes | ok |
| Prnp | OK | 5.00E−05 | 0.000206 | yes | ok |
| Pmaip1 | OK | 5.00E−05 | 0.000206 | yes | ok |
| Cd44 | OK | 5.00E−05 | 0.000206 | yes | ok |
| Ptpn3 | OK | 5.00E−05 | 0.000206 | yes | ok |
| Serpinb9 | OK | 5.00E−05 | 0.000206 | yes | ok |
| Prkar2b | OK | 5.00E−05 | 0.000206 | yes | ok |
| Tsc22d1 | OK | 0.0016 | 0.005017 | yes | ok |
| Pdgfb | OK | 0.0002 | 0.000753 | yes | ok |
| Tubb2a | OK | 5.00E−05 | 0.000206 | yes | ok |
| 6720401G13Rik | OK | 5.00E−05 | 0.000206 | yes | ok |
| Ptpla | OK | 5.00E−05 | 0.000206 | yes | ok |
| Tnfsf11 | OK | 5.00E−05 | 0.000206 | yes | ok |
| Tnfsf4 | OK | 5.00E−05 | 0.000206 | yes | ok |
| H1f0 | OK | 5.00E−05 | 0.000206 | yes | ok |
| Slc25a33 | OK | 5.00E−05 | 0.000206 | yes | ok |
| Rhoc | OK | 0.00035 | 0.001262 | yes | ok |
| Hip1 | OK | 5.00E−05 | 0.000206 | yes | ok |
| Tdrkh | OK | 5.00E−05 | 0.000206 | yes | ok |
| Tmbim1 | OK | 0.00025 | 0.000925 | yes | ok |
| Napsa | OK | 5.00E−05 | 0.000206 | yes | ok |
| Cyfip1 | OK | 0.00055 | 0.001907 | yes | ok |
| Hmox1 | OK | 5.00E−05 | 0.000206 | yes | ok |
| Pros1 | OK | 5.00E−05 | 0.000206 | yes | ok |
| Serpinb6a | OK | 5.00E−05 | 0.000206 | yes | ok |
| Trim16 | OK | 5.00E−05 | 0.000206 | yes | ok |
| Luzp1 | OK | 5.00E−05 | 0.000206 | yes | ok |
| Fam213a | OK | 5.00E−05 | 0.000206 | yes | ok |
| Ccbl2 | OK | 0.0001 | 0.000396 | yes | ok |
| Smo | OK | 5.00E−05 | 0.000206 | yes | ok |
| Spire1 | OK | 5.00E−05 | 0.000206 | yes | ok |
| Sccpdh | OK | 5.00E−05 | 0.000206 | yes | ok |
| Scamp1 | OK | 5.00E−05 | 0.000206 | yes | ok |
| Adap1 | OK | 5.00E−05 | 0.000206 | yes | ok |
| Bmi1 | OK | 5.00E−05 | 0.000206 | yes | ok |
| Snx8 | OK | 5.00E−05 | 0.000206 | yes | ok |
| Cenpv | OK | 5.00E−05 | 0.000206 | yes | ok |
| Erdr1 | OK | 5.00E−05 | 0.000206 | yes | ok |
| Eomes | OK | 5.00E−05 | 0.000206 | yes | ok |
| Errfi1 | OK | 5.00E−05 | 0.000206 | yes | ok |
| Hbegf | OK | 5.00E−05 | 0.000206 | yes | ok |
| Serpinf1 | OK | 5.00E−05 | 0.000206 | yes | ok |
| Abcg2 | OK | 5.00E−05 | 0.000206 | yes | ok |
| Dapk2 | OK | 5.00E−05 | 0.000206 | yes | ok |
| Spp1 | OK | 5.00E−05 | 0.000206 | yes | ok |
| H2-Aa | OK | 0.0004 | 0.001426 | yes | ok |
| Tmem40 | OK | 0.0005 | 0.001749 | yes | ok |
| Ccl4 | OK | 5.00E−05 | 0.000206 | yes | ok |
| Swap70 | OK | 5.00E−05 | 0.000206 | yes | ok |
| Ifng | OK | 5.00E−05 | 0.000206 | yes | ok |
| Scn1b | OK | 0.0001 | 0.000396 | yes | ok |
| Apobr | OK | 5.00E−05 | 0.000206 | yes | ok |
| Emilin2 | OK | 5.00E−05 | 0.000206 | yes | ok |
| Vcl | OK | 5.00E−05 | 0.000206 | yes | ok |
| Sgk1 | OK | 5.00E−05 | 0.000206 | yes | ok |
| Tjp2 | OK | 5.00E−05 | 0.000206 | yes | ok |

TABLE 3-continued

Genes differentially expressed in activated Ezh2−/− CD8 T cells versus WT CD8 T cells (fold changes >1.5, or <1.5)

| Gene | | | | | |
|---|---|---|---|---|---|
| Arsb | OK | 5.00E−05 | 0.000206 | yes | ok |
| Dennd3 | OK | 5.00E−05 | 0.000206 | yes | ok |
| Fam129b | OK | 0.003 | 0.008852 | yes | ok |
| Ceacam1 | OK | 0.00025 | 0.000925 | yes | ok |
| Itga3 | OK | 5.00E−05 | 0.000206 | yes | ok |
| Ccl3 | OK | 5.00E−05 | 0.000206 | yes | ok |
| Stard10 | OK | 5.00E−05 | 0.000206 | yes | ok |
| Entpd1 | OK | 5.00E−05 | 0.000206 | yes | ok |
| Mid1 | OK | 5.00E−05 | 0.000206 | yes | ok |
| Efemp2 | OK | 5.00E−05 | 0.000206 | yes | ok |
| Prdm1 | OK | 5.00E−05 | 0.000206 | yes | ok |
| Csrp2 | OK | 5.00E−05 | 0.000206 | yes | ok |
| Spats2 | OK | 5.00E−05 | 0.000206 | yes | ok |
| Myo1e | OK | 5.00E−05 | 0.000206 | yes | ok |
| Ift43 | OK | 0.0001 | 0.000396 | yes | ok |
| Nrgn | OK | 5.00E−05 | 0.000206 | yes | ok |
| Pctp | OK | 5.00E−05 | 0.000206 | yes | ok |
| Bag3 | OK | 5.00E−05 | 0.000206 | yes | ok |
| Ryk | OK | 5.00E−05 | 0.000206 | yes | ok |
| Gadd45g | OK | 5.00E−05 | 0.000206 | yes | ok |
| Smpdl3b | OK | 5.00E−05 | 0.000206 | yes | ok |
| Adam8 | OK | 5.00E−05 | 0.000206 | yes | ok |
| Runx2 | OK | 5.00E−05 | 0.000206 | yes | ok |
| Cth | OK | 5.00E−05 | 0.000206 | yes | ok |
| Id2 | OK | 5.00E−05 | 0.000206 | yes | ok |
| Tnfsf10 | OK | 5.00E−05 | 0.000206 | yes | ok |
| Cxcr6 | OK | 0.0001 | 0.000396 | yes | ok |
| Crabp2 | OK | 5.00E−05 | 0.000206 | yes | ok |
| S100a6 | OK | 5.00E−05 | 0.000206 | yes | ok |
| Map6 | OK | 5.00E−05 | 0.000206 | yes | ok |
| Pde8a | OK | 5.00E−05 | 0.000206 | yes | ok |
| Ell2 | OK | 5.00E−05 | 0.000206 | yes | ok |
| Srxn1 | OK | 5.00E−05 | 0.000206 | yes | ok |
| Ccl5 | OK | 5.00E−05 | 0.000206 | yes | ok |
| Gpx7 | OK | 5.00E−05 | 0.000206 | yes | ok |
| Selp | OK | 5.00E−05 | 0.000206 | yes | ok |
| Myo10 | OK | 5.00E−05 | 0.000206 | yes | ok |
| Ckap4 | OK | 5.00E−05 | 0.000206 | yes | ok |
| Ifitm2 | OK | 5.00E−05 | 0.000206 | yes | ok |
| Ccr5 | OK | 5.00E−05 | 0.000206 | yes | ok |
| Prf1 | OK | 5.00E−05 | 0.000206 | yes | ok |
| Igf2bp3 | OK | 5.00E−05 | 0.000206 | yes | ok |
| Lgals3 | OK | 5.00E−05 | 0.000206 | yes | ok |
| Ttc39c | OK | 5.00E−05 | 0.000206 | yes | ok |
| Il3 | OK | 5.00E−05 | 0.000206 | yes | ok |
| AA467197 | OK | 5.00E−05 | 0.000206 | yes | ok |
| Myh10 | OK | 5.00E−05 | 0.000206 | yes | ok |
| Lad1 | OK | 5.00E−05 | 0.000206 | yes | ok |
| Havcr2 | OK | 5.00E−05 | 0.000206 | yes | ok |
| Lat2 | OK | 5.00E−05 | 0.000206 | yes | ok |
| S100a4 | OK | 5.00E−05 | 0.000206 | yes | ok |
| H2-Q10 | OK | 5.00E−05 | 0.000206 | yes | ok |
| Upp1 | OK | 5.00E−05 | 0.000206 | yes | ok |
| Calcb | OK | 5.00E−05 | 0.000206 | yes | ok |
| Plcg2 | OK | 5.00E−05 | 0.000206 | yes | ok |
| Lmna | OK | 5.00E−05 | 0.000206 | yes | ok |
| Chit1 | OK | 5.00E−05 | 0.000206 | yes | ok |
| Tmem37 | OK | 5.00E−05 | 0.000206 | yes | ok |
| Sytl2 | OK | 5.00E−05 | 0.000206 | yes | ok |
| Adamts14 | OK | 5.00E−05 | 0.000206 | yes | ok |
| Chst11 | OK | 5.00E−05 | 0.000206 | yes | ok |
| Gem | OK | 5.00E−05 | 0.000206 | yes | ok |
| 2900026A02Rik | OK | 5.00E−05 | 0.000206 | yes | ok |
| Csf2 | OK | 5.00E−05 | 0.000206 | yes | ok |
| Stk32c | OK | 0.0001 | 0.000396 | yes | ok |
| Batf3 | OK | 5.00E−05 | 0.000206 | yes | ok |
| Mt3 | OK | 5.00E−05 | 0.000206 | yes | ok |
| Serpine2 | OK | 5.00E−05 | 0.000206 | yes | ok |
| Prr5 | OK | 5.00E−05 | 0.000206 | yes | ok |
| Rgs8 | OK | 5.00E−05 | 0.000206 | yes | ok |
| Gatm | OK | 5.00E−05 | 0.000206 | yes | ok |
| Ccl1 | OK | 5.00E−05 | 0.000206 | yes | ok |
| Slc16a11 | OK | 5.00E−05 | 0.000206 | yes | ok |
| Cd63 | OK | 5.00E−05 | 0.000206 | yes | ok |
| Ifitm3 | OK | 5.00E−05 | 0.000206 | yes | ok |
| Fkbp11 | OK | 5.00E−05 | 0.000206 | yes | ok |
| Tmem163 | OK | 5.00E−05 | 0.000206 | yes | ok |

TABLE 3-continued

Genes differentially expressed in activated Ezh2-/- CD8 T cells versus WT CD8 T cells (fold changes >1.5, or <1.5)

| | | | | | |
|---|---|---|---|---|---|
| Prkcdbp | OK | 5.00E-05 | 0.000206 | yes | ok |
| 2810025M15Rik | OK | 5.00E-05 | 0.000206 | yes | ok |
| Nkain1 | OK | 5.00E-05 | 0.000206 | yes | ok |
| Lrrk1 | OK | 5.00E-05 | 0.000206 | yes | ok |
| Sdc1 | OK | 5.00E-05 | 0.000206 | yes | ok |
| Il10 | OK | 5.00E-05 | 0.000206 | yes | ok |
| Tnfrsf8 | OK | 5.00E-05 | 0.000206 | yes | ok |
| Gzmk | OK | 5.00E-05 | 0.000206 | yes | ok |
| Ccl9 | OK | 5.00E-05 | 0.000206 | yes | ok |
| Ccr2 | OK | 5.00E-05 | 0.000206 | yes | ok |
| Serpinb9b | OK | 5.00E-05 | 0.000206 | yes | ok |
| Ifitm1 | OK | 5.00E-05 | 0.000206 | yes | ok |
| Filip1 | OK | 5.00E-05 | 0.000206 | yes | ok |
| Atp6v0d2 | OK | 5.00E-05 | 0.000206 | yes | ok |
| Cdkn2a | OK | 5.00E-05 | 0.000206 | yes | ok |
| Gzmc | OK | 5.00E-05 | 0.000206 | yes | ok |
| Gzma | OK | 5.00E-05 | 0.000206 | yes | ok |
| Gzme | OK | 0.00135 | 0.004299 | yes | ok |
| Gzmd | OK | 0.00295 | 0.008719 | yes | ok |
| Mir1199 | OK | 0.00285 | 0.008452 | yes | ok |

To assess the impact of Ezh2 deficiency on TF expression in memory precursor cells, $T_{CMP}$ and $T_{EFF}$ were isolated from WT and Ezh2$^{-/-}$ Pmel-1 cell recipients 4 days after activation. As compared to WT $T_{CMP}$, Ezh2$^{-/-}$ $T_{CMP}$ had lower levels of Id3, but higher expression of Id2 and Eomes (FIG. 10B). In $T_{EFF}$, Ezh2 deficiency led to significantly increased expression of Id2, Eomes and Prdm1 (FIG. 10B). Chromatin immunoprecipitation (ChIP) analysis was performed, and it was observed that Ezh2 bound to the promoter regions of Id3, Id2, Prdm1 and Eomes loci (FIG. 10C). This was confirmed using chromatin from activated Ezh2$^{-/-}$ Pmel-1 cells 3 days after activation as evidenced by decreased amount of Ezh2 and H3K27me3 at the promoter region of these gene loci (FIG. 10D). Ezh2 appeared to have differentially effects on Tbx21 (which encodes T-bet) expression between $T_{CMP}$ versus $T_{EFF}$ via an unknown mechanism (FIG. 10B and FIG. 10C). Since CD8+ T cells that express high levels of Prdm1, Id2 and Tbx21 but low levels of Id3 are reported to undergo accelerated and enhanced terminal differentiation (Chang et al., 2014, Nat Immunol, 15:1104-1115; Kaech and Cui, 2012, Nat Rev Immunol, 12:749-761; Ji et al., 2011, Nat Immunol, 12:1230-1237; Yang et al., 2011, Nat Immunol, 12:1221-1229). These data suggest that Ezh2 orchestrates the expression of TFs that are critical for controlling stepwise effector differentiation and memory formation of antigen-driven CD8+ T cells.

Figures 11A, 11B, 11C, 11D, 11E, 11F, 11G:
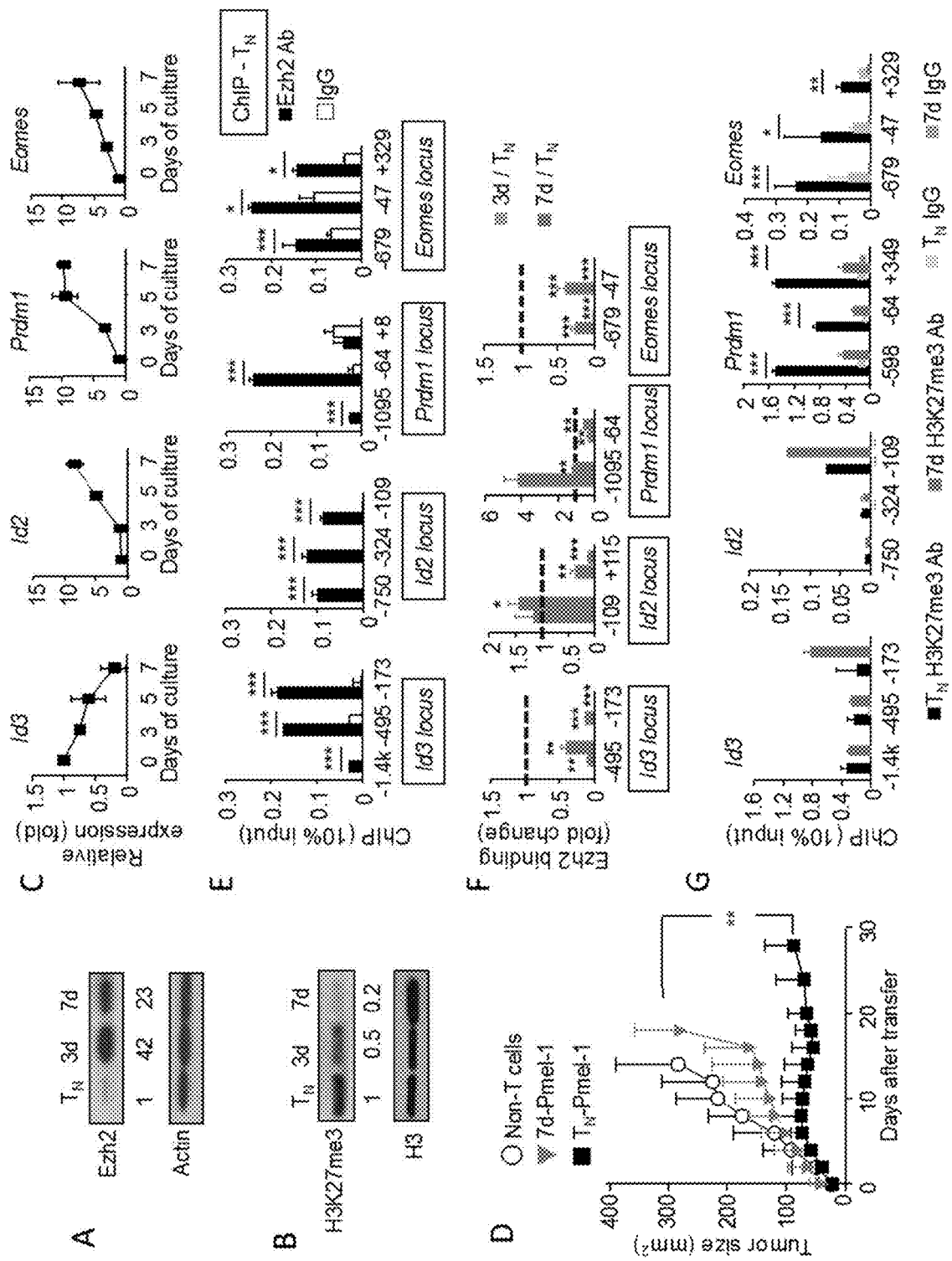
FIG. 11A through FIG. 11G, depicts exemplary experimental results demonstrating Ezh2 is dissociated from the promoter regions of TFs during CD8+ T cell expansion. For FIG. 11A and FIG. 11B WT $T_N$ Pmel-1 cells were stimulated with anti-CD3/CD28 Ab+IL-2.

Akt-Mediated Phosphorylation of Ezh2 Impairs its Capacity to Regulate Memory CD8+ T Cells During immune response, upon antigen activation, normal CD8+ T cells express high levels of Ezh2, however, they still undergo a "programmed" differentiation into terminal $T_{EFF}$. This points to a mechanism that might modify Ezh2 function in T cells. To test it, TCR-activated Pmel-1 cells were evaluated and it was found that they expressed 42- and 23-fold higher cellular Ezh2 protein 3 days and 7 days after culture, respectively, than $T_N$ (FIG. 11A). However, as compared to $T_N$, activated CD8+ T cells showed profoundly decreased Ezh2 function, as evidenced by the fact that 3 day- and 7 day-Pmel-1 cells contained 2- and 5-fold less H3K27me3, respectively (FIG. 11B), higher expression of Ezh2-silenced genes Id2, Eomes and Prdm1 while decreasing Ezh2-activated gene Id3 (FIG. 11C), and impaired antitumor activity compared to $T_N$ Pmel-1 cells upon adoptive transfer (FIG. 11D). The reduction of cellular H3K27me3 is in agreement with others' observation that the deposition of H3K27me3 on the regulatory region of genes (e.g., Tbx21, Eomes, Prdm1) was decreased in activated CD8$^+$ T cells (Russ et al., 2014, Immunity, 41:853-865).

To determine the molecular mechanisms that reduced T cell Ezh2 function during expansion, ChIP analysis was performed. In CD8+ TN, Ezh2 bound to the promoter region of Id3, Id2, Prdm1 and Eomes (FIG. 11E). However, the amount of Ezh2 within these promoter regions was dramatically decreased in these proliferating CD8+ T cells, which occurred 3 days after activation and persisted throughout 7 days (FIG. 11F). This decreased presence of Ezh2 was paralleled by a reduction of H3K27me3 at the Prdm1 and Eomes loci (FIG. 11G). Thus, Ezh2 is dissociated from the promoter regions of these TFs as early as 3 days after activation.

Figures 12A, 12B, 12C, 12D:
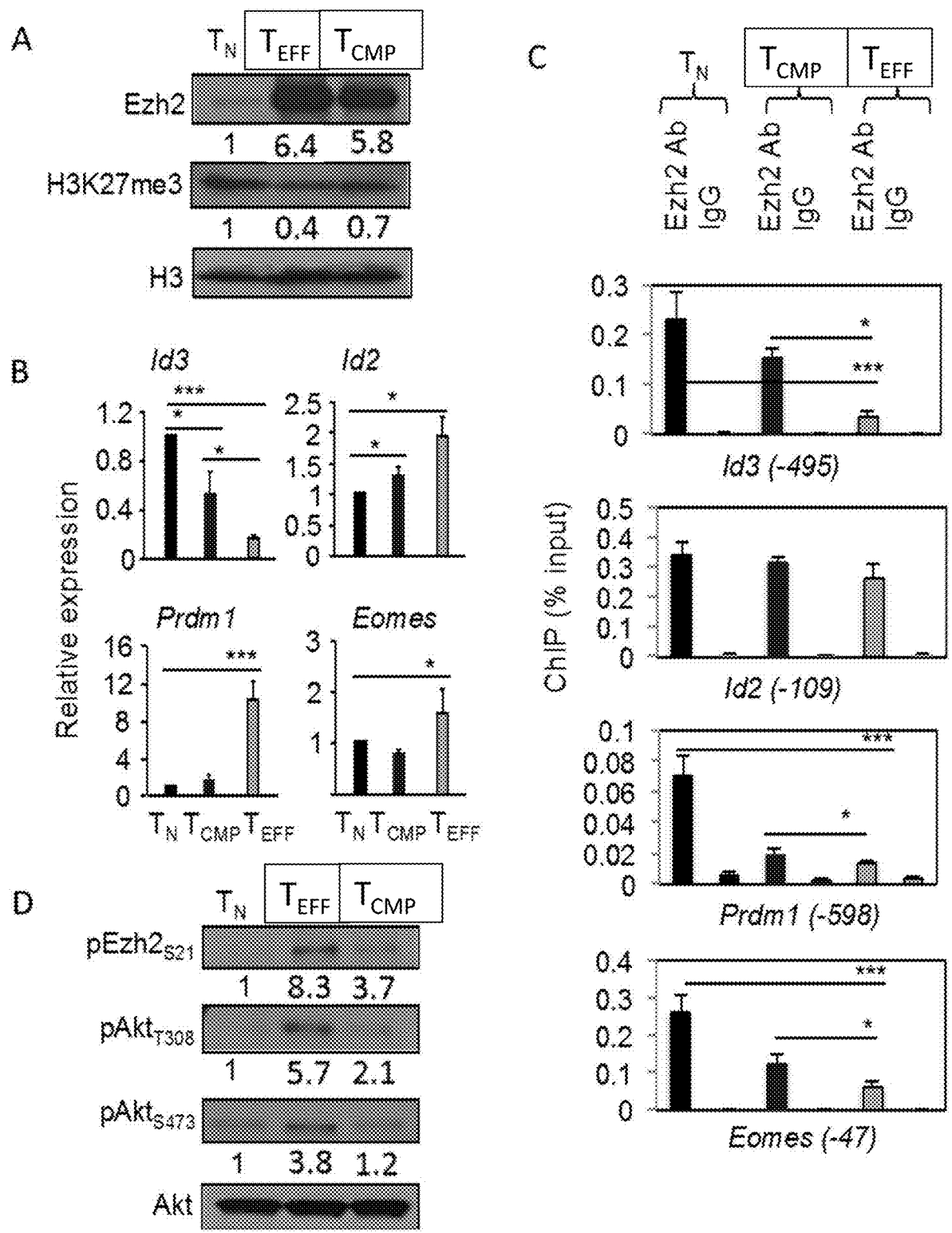
FIG. 12A through FIG. 12D, depicts exemplary experimental results demonstrating that Akt-mediated phosphorylation of Ezh2 reduces Ehz2 function in activated CD8$^+$ T cells. WT and Ezh2$^{-/-}$ naïve Pmel-1 cells (1×10$^6$, Thy1.1$^+$) were transferred into sublethally irradiated B6 mice (Thy1.2$^+$), followed by treatment with IL-2 and gp100/DCs. $T_{CMP}$ and $T_{EFF}$ were highly purified using cell sorter from the spleen of these primary recipients 7 days after transfer.

To determine if $T_{CMP}$ and $T_{EFF}$ differentially modify Ezh2 function, $T_{EFF}$ and $T_{CMP}$ were recovered from WT Pmel-1 cell recipients 7 days after activation. As compared to $T_N$, $T_{EFF}$ expressed higher levels of Ezh2 (FIG. 12A) but upregulated the expression of Id2, Prdm1 and Eomes and decreased Id3 (FIG. 12B). ChIP analysis revealed a reduction of Ezh2 at the regulatory regions of Id3, Prdm1 and Eomes in $T_{EFF}$ (FIG. 12B). These data suggest the dissociation of Ezh2 from the promoters of these genes in $T_{EFF}$. $T_{CMP}$ significantly decreased the amount of Ezh2 within the promoters of Id3, Eomes and Prdm1 compared to $T_N$, but they retained more Ezh2 at the promoter regions of these gene loci than $T_{EFF}$ (FIG. 12C). This correlated with higher levels of Id3 transcripts but lower transcription of Prdm1 and Eomes in $T_{CMP}$ than $T_{EFF}$ (FIG. 12B). Thus, Ezh2 function is altered in both $T_{CMP}$ and $T_{EFF}$, with more dramatic changes in $T_{EFF}$.

Figures 13A, 13B, 13C, 13D:
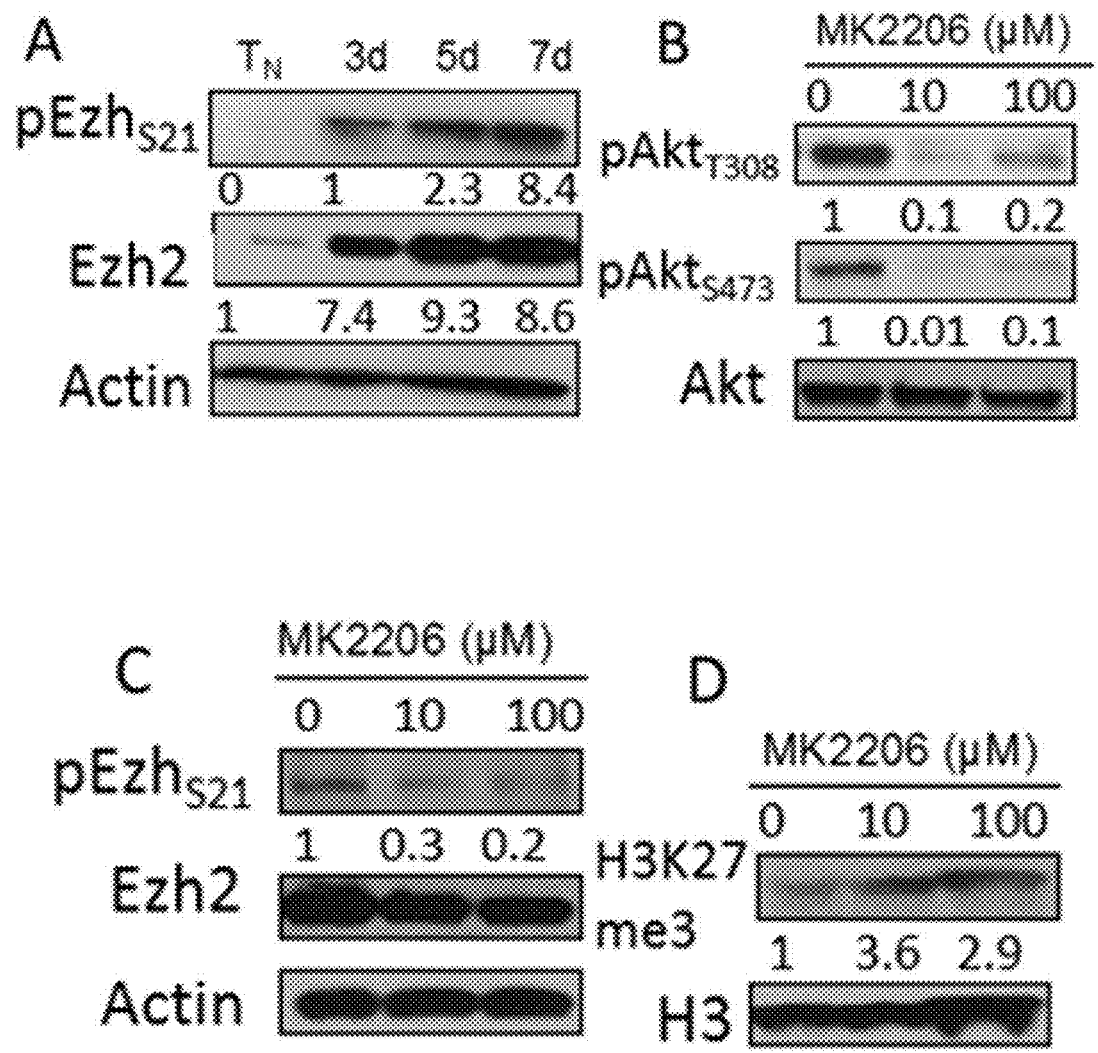
FIG. 13A through FIG. 13K, depicts exemplary experimental results demonstrating phosphorylation of Ezh2 by Akt dissociates Ezh2 from the promoter regions of major TF loci.
Figures 13E, 13F, 13G:
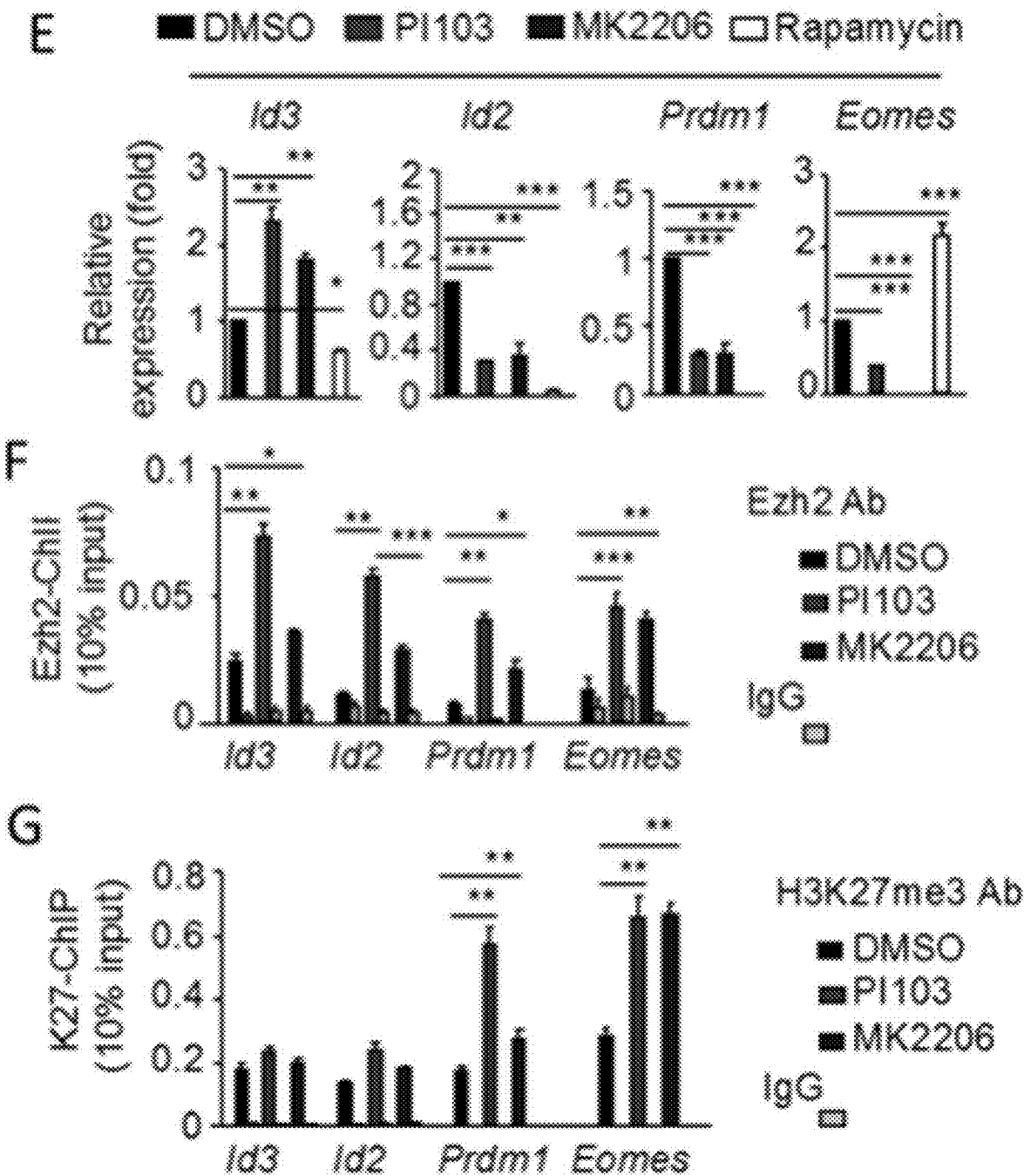

Phosphatidylinositol 3-kinase (PI3K)/Akt promotes the proliferation and differentiation of activated CD8+ T cells (Kim and Suresh, 2014, Front Immunol, 4:20). In cancer cells, Akt is reported to phosphorylate Ezh2 at serine 21 (pEzh2S21), thereby suppressing Ezh2 enzymatic activity in cancer cells (Cha et al., 2005, Science, 310:306-310). To determine if Akt phosphorylation of Ezh2 caused Ezh2 dissociation from these TF loci, highly purified $T_{CMP}$ and $T_{EFF}$ were obtained from B6 mice receiving Pmel-1 cells 7 days after activation, with $T_N$ as controls. $T_{EFF}$ and $T_{CMP}$ had 8.3-fold and 3.7-fold more pEzh2S21, respectively, than $T_N$ (FIG. 12D), which was correlated with lower levels of H3K27me3 and higher levels of pAkt (FIG. 12A and FIG. 12D). Similarly, pEzh2$_{S21}$ occurred in TCR-activated CD8+ T cells 3 days after culture, which further increased over time; by day 5 and day 7, activated cells expressed 2.3-fold and 8.4-fold more pEzh2$_{S21}$ than $T_N$ (FIG. 13A). Treatment with MK2206, an allosteric inhibitor of Akt, led to a marked decrease of pEzh2S21 and increase of H3K27me3 in proliferating CD8+ T cells (FIG. 13B through FIG. 13D). Inhibiting Akt or its upstream activator PI3K by PI103 likewise upregulated Id3 expression while reducing Id2, Eomes and Prdm1 (FIG. 13E), affirming an orchestrated regulatory pathway across these TFs. ChIP assay demonstrated that inhibiting Akt activity significantly increased the amount of Ezh2 and H3K27me3 at the promoter regions of Id3, Id2, Eomes and Prdm1 loci (FIG. 13F and FIG. 13G). Rapamycin inhibition of mTOR, a down-stream effector of Akt pathway (Kim and Suresh, 2014, Front Immunol, 4:20; Inoki et al., 2006, Cell, 126:955-968), increased Eomes expression and reduced Id3 (FIG. 13E), suggesting that the mechanism of Ezh2 inhibition by Akt likely differs from mTOR-dependent effects.

Figures 13H, 13I, 13J, 13K:
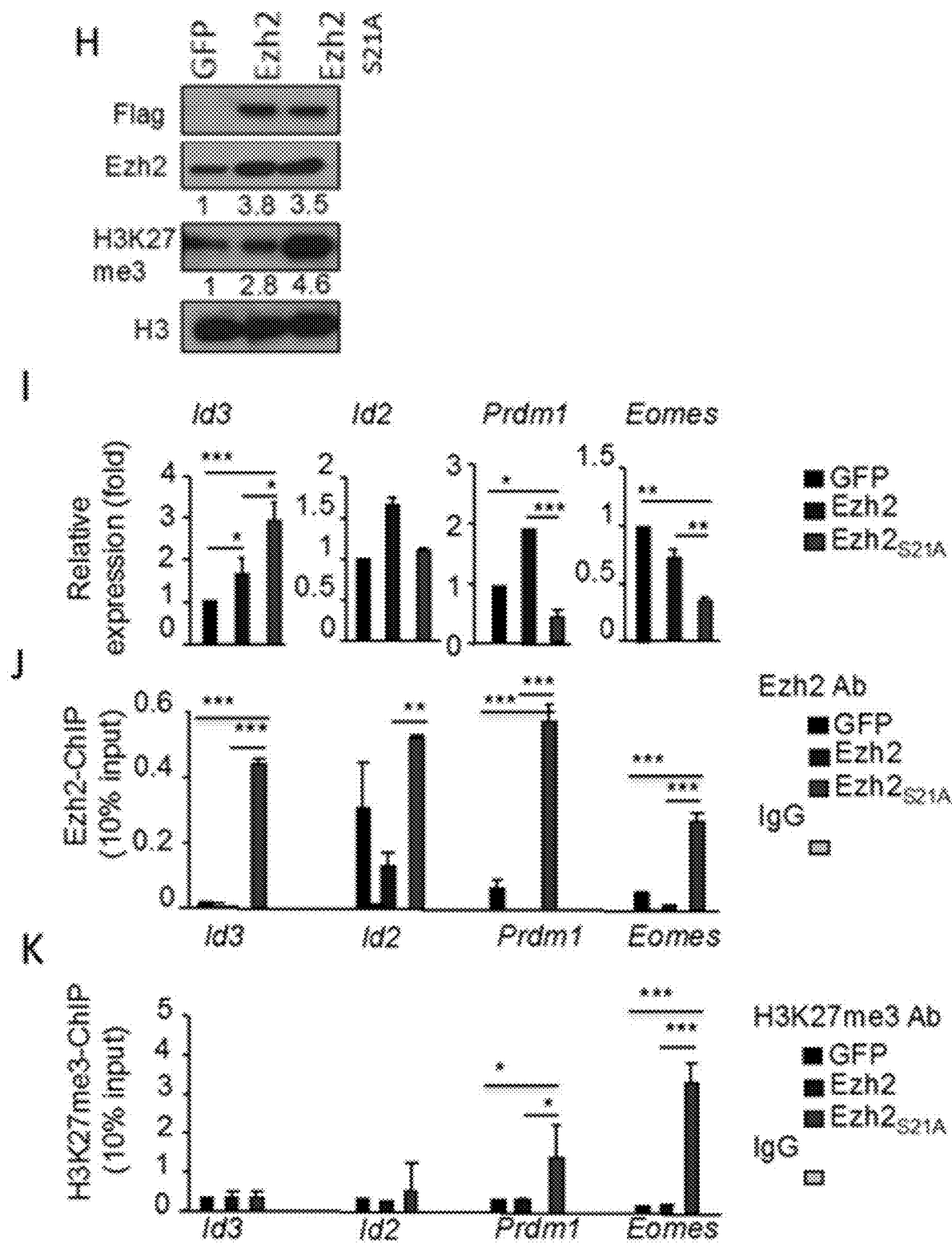
Figures 14A, 14B, 14C:
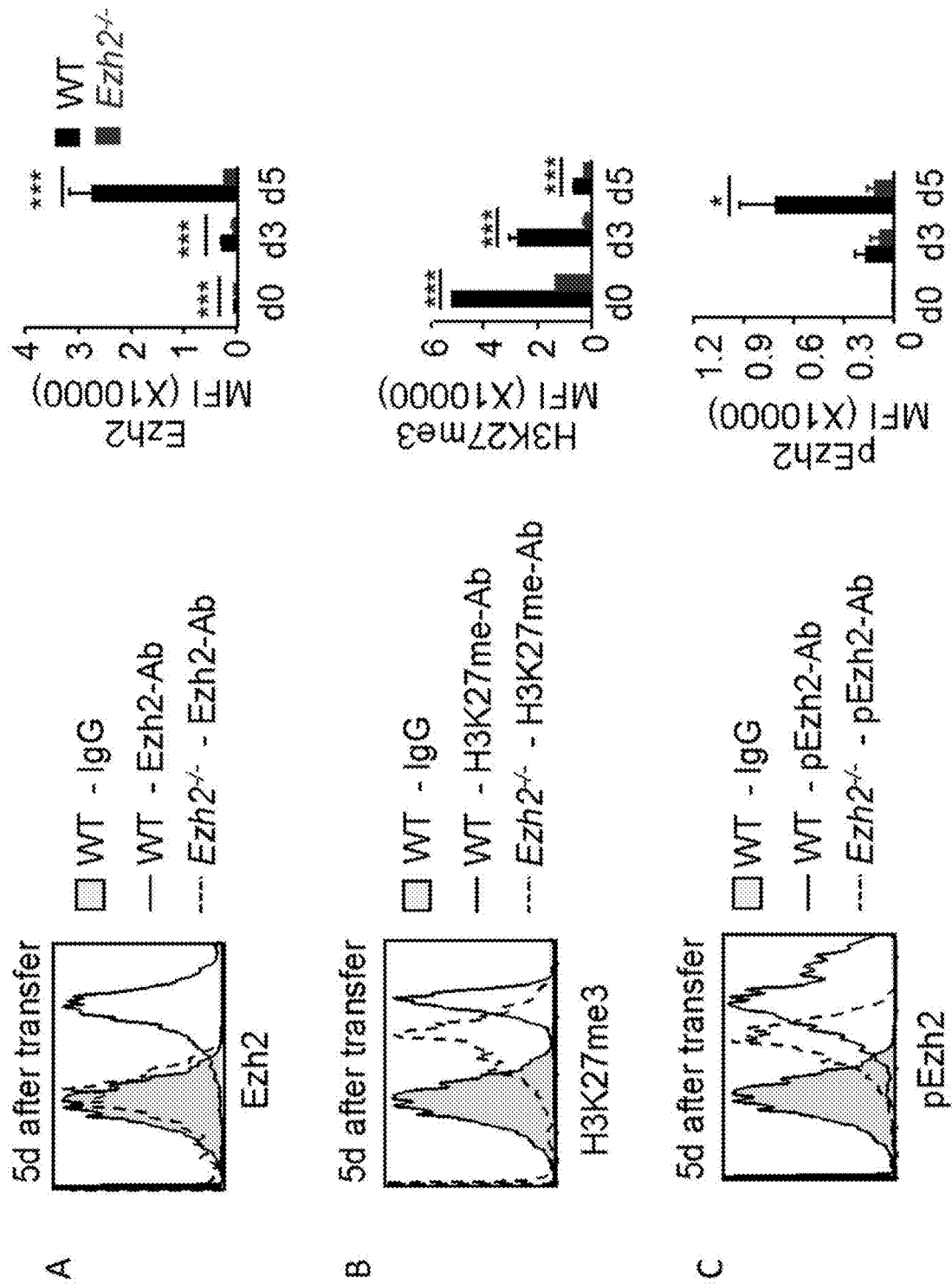
FIG. 14A through FIG. 14C, depicts exemplary experimental results demonstrating Ezh2 is progressively phosphorylated by Akt in activated CD8$^+$ T cells in vivo. WT (CD45.2$^+$Thy1.1$^+$) and Ezh2$^{-/-}$ (CD45.2$^+$ Thy1.1$^-$) $T_N$ Pmel-1 cells were co-transferred into B6/SJL mice (CD45.1$^+$Thy1.1$^-$), followed with VVA-gp100 infection.

To establish a specific effect of Akt-mediated phosphorylation of Ezh2 on its function, Pmel-1 cells were infected with retrovirus encoding Akt-phosphorylation resistant Ezh2 in which the serine at amino acid 21 was replaced by alanine (named Ezh2S21A). After 7 days, Pmel-1 cells expressing Ezh2S21A significantly increased H3K27me3 compared to GFP control (FIG. 13H). Expressing Ezh2S21A also upregulated Id3 transcript and repressed Eomes and Prdm1 expression (FIG. 13I), and increased the amount of Ezh2 at the Id3, Id2, Eomes and Prdm1 loci (FIG. 13J). Notably, introduction of Ezh2S21A increased the H3K27me3 level within the Eomes and Prdm1 loci but not the Id3 and Id2 loci (FIG. 13K), suggesting that epigenetic regulation of these loci occurs via a different mechanism. Using lymporeplete hosts infected by VVA-gp100, it was confirmed that WT Pmel-1 cells, rather than Ezh2−/− Pmel-1 cells, induced Ezh2 and pEzh2S21 3 days after activation and markedly increased by day 5 (FIG. 14A and FIG. 14B), which was inversely correlated to the decreased cellular H3K27me3 (FIG. 14C). In aggregate, Akt activation profoundly reduces Ezh2 function in activated CD8+ T cells.

Figures 15A, 15B, 15C:
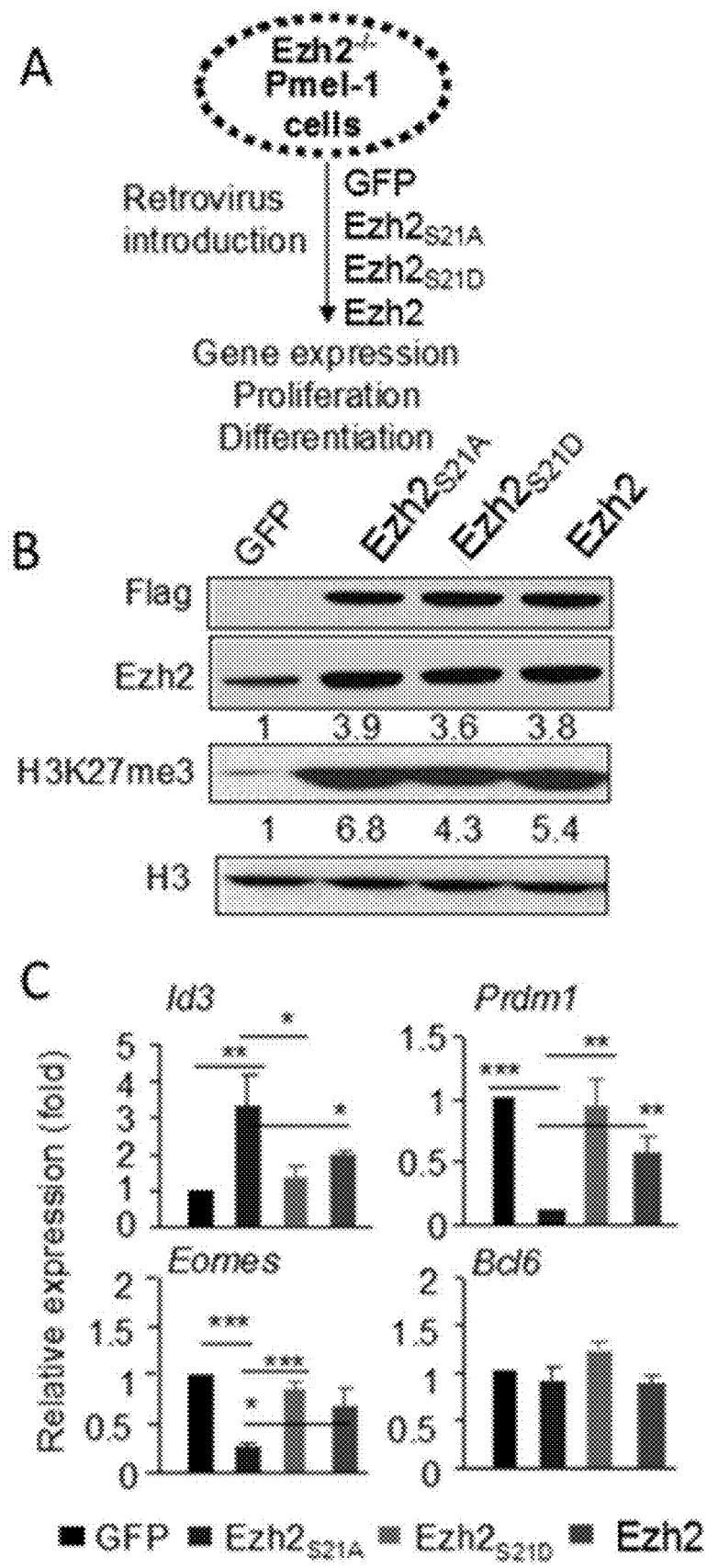
FIG. 15A through FIG. 15E, depicts exemplary experimental results demonstrating that inhibiting Akt-mediated phosphorylation of Ezh2 enhances the generation of $T_{CMP}$. Ezh2$^{-/-}$ mel-1 cells (Thy1.1$^+$) were stimulated with anti-CD3/CD28 Ab+IL-2 for 36 hours, followed by infection with MigR1 retrovirus encoding GFP, Ezh2, Ezh2s21D and Ezh2$_{S21A}$, respectively. At day 7 after stimulation, these infected T cells were collected.
Figures 15D, 15E:
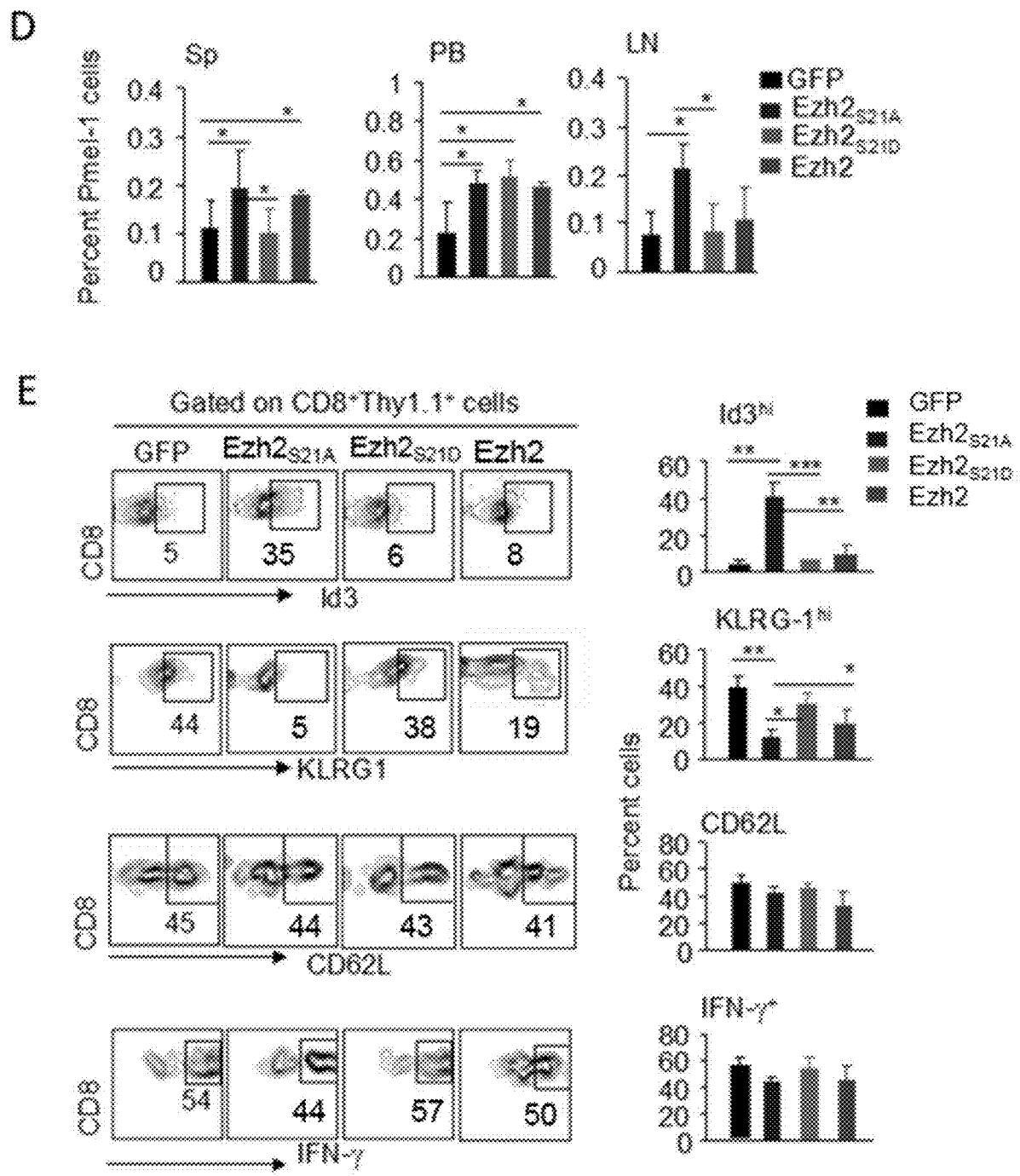

To examine the impact of Ezh2 phosphorylation by Akt on CD8+ T cell differentiation, retrovirus encoding a phosphor-mimetic Ezh2 were made in which serine 21 was replaced by aspartate (named Ezh2S21D) (Cha et al., 2005, Science, 310:306-310), and introduced both Ezh2S21A and Ezh2S21D into activated Ezh2$^{-/-}$ Pmel-1 cells (FIG. 15A). This allowed the assessment of the specific effects of phosphor-resistant Ezh2 and phosphor-mimetic Ezh2 on the expression of these defined TFs in the absence of endogenous Ezh2. As compared to Ezh2S21D, Ezh2S21A increased the amount of H3K27me3 in activated CD8+ T cells (FIG. 15B), and induced high levels of Id3 but reduced Eomes and Prdm1 transcripts in these T cells in cultures 7 days after activation (FIG. 15C). Upon transfer into sublethally irradiated B6 mice and treatment with IL-2 and gp100/DCs, Ezh2−/− Pmel-1 cells overexpressing Ezh2S21A produced more donor T cells (FIG. 15D) and 6-fold more Id3hi donor cells, compared to Ezh2S21D 6 d after transfer (FIG. 15E). Overexpressing Ezh2S21A caused 3-fold smaller in frequency of KLRG1hi T cells than Ezh2S21D, without significantly changing the fraction of CD62Lhi T cells and IFN-γ-producing cells (FIG. 15E). Notably, as compared to Ezh2S21A, overexpressing WT Ezh2 in Ezh2−/− Pmel-1 cells was able to rescue their survival in vivo (FIG. 15D), but less effective in modifying the expression Id3, Prdm1 and Eomes (FIG. 15C) and unable to sustain Id3hi T cells (FIG. 15E). Therefore, these investigations reveal critical contributions of Ezh2 phosphorylation for control of T memory cell differentiation, beyond T cell survival. Furthermore, they identify Akt-mediated phosphorylation of Ezh2 as a novel and important mechanism regulating effector differentiation and memory formation.

Figures 16A, 16B:
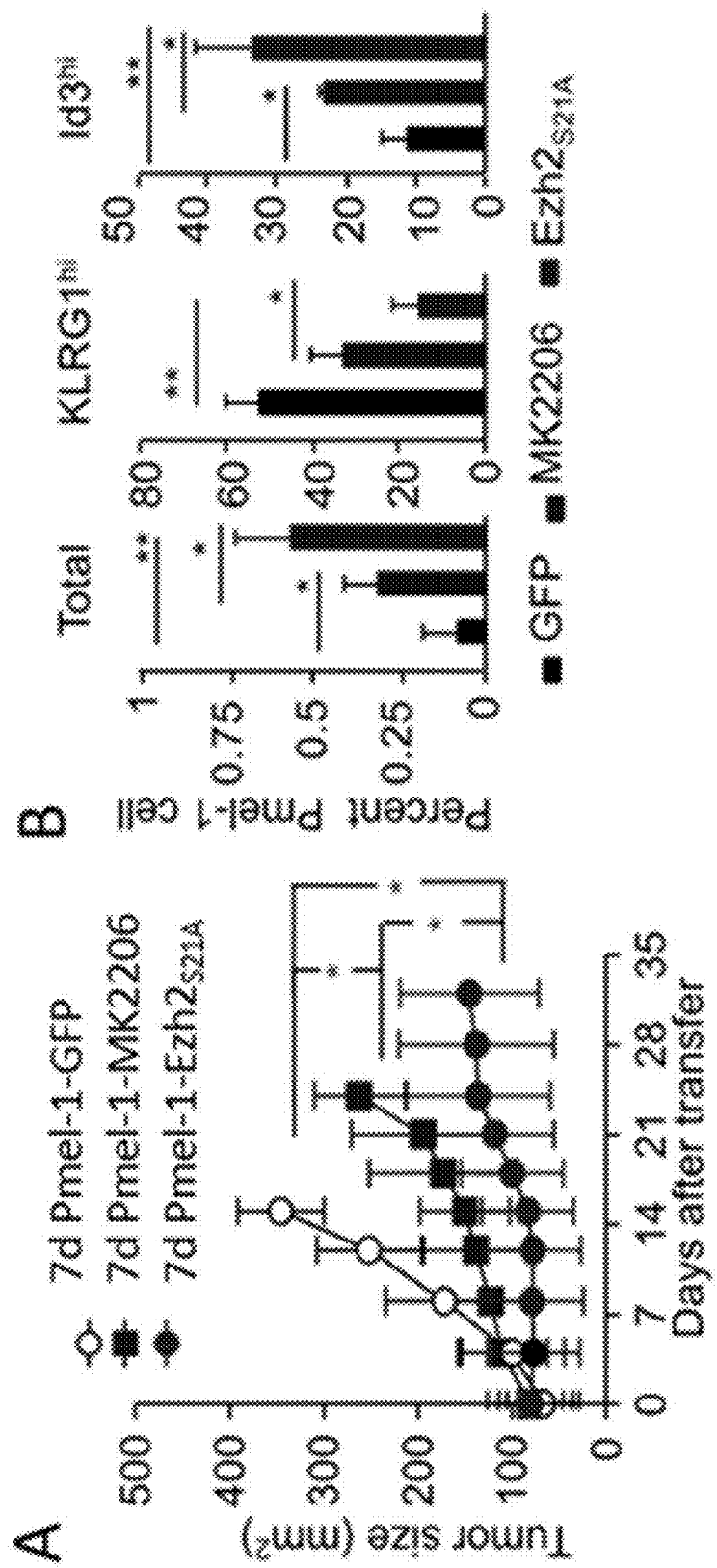
FIG. 16A through FIG. 16H, depicts exemplary experimental results demonstrating that inhibiting Akt-mmdiated Ezh2 phosphorylation improves CD8$^+$ T cell-mediated antitumor immunity. For FIG. 16A and FIG. 16B, ex vivo expanded 7 day Pmel-1 cells (Thy1.1$^+$), MK2206-treated 7 day Pmel-1 cells (Thy1.1$^-$), or 7 day Pmel-1 cells infected with MigR1 retrovirus encoding Ezh2$_{S21A}$ (Thy1.1$^-$, 5×10$^5$ T cells/mouse) were transferred into sublethally irradiated B6 mice that had pre-established B16 melanoma, followed by treatment with IL-2 and gp100/DCs from day 0-day 3 and repeated once more from day 18-day 20.

Akt-Insensitive Ezh2 Augments T Cell Memory Recall Response and Antitumor Efficacy Adoptive immunotherapy for cancer requires sufficient amplification and persistence of tumor-specific T cells to eradicate the tumor (Rosenberg and Restifo, 2015, Science, 348:62-68; Restifo et al., 2012, Nat Rev Immunol, 12:269-281; Jensen and Riddell, 2014, Immunol Rev, 257:127-144; Vonderheide and June, 2014, Immunol Rev, 257:7-13). However, current in vitro methods to expand cells to sufficient numbers impair the maintenance of memory properties in these ex vivo cultured T cells (Restifo et al., 2012, Nat Rev Immunol, 12:269-281; Jensen and Riddell, 2014, Immunol Rev, 257:127-144). Akt activation occurs in activated T cells not only during ex vivo expansion but also during in vivo replication after transfer (Kim and Suresh, 2014, Front Immunol, 4:20). Data from recent studies indicate that ex vivo treatment of expanding CD8+ T cells with an Akt inhibitor led to an increased frequency of memory phenotype cells and improved antitumor immunity in vivo (Crompton et al., 2015, Cancer Res, 75, 296-305; van der Waart et al., 2014, Blood, 124:3490-3500). Indeed, transfer of Pmel-1 cells treated by MK2206 during ex vivo culture induced greater anti-tumor activity than untreated Pmel-1 cells, but was less potent than Ezh2$_{S21A}$-transduced Pmel-1 cells for controlling tumor growth (FIG. 16A). Mechanistic analysis revealed that as compared to MK2206-treated Pmel-1 cell recipients, Ezh2S21A- and GFP-Pmel-1 cell recipients had similar amounts of donor T cells in the circulating PB within 7 days after transfer, however, when donor T cells were followed in PB, Ezh2S21A-Pmel-1 cell recipients generated significantly higher frequency of total Pmel-1 cells and Id3$^{hi}$ Pmel-1 cells, but a lower frequency of KLRG1$^{hi}$ cells in the spleen 9 days after transfer (FIG. 16B). These data suggest that MK2206-treated CD8+ T cells likely reactivate Akt in vivo after transfer to reduce their Ezh2 function.

Figures 16C, 16D, 16E:
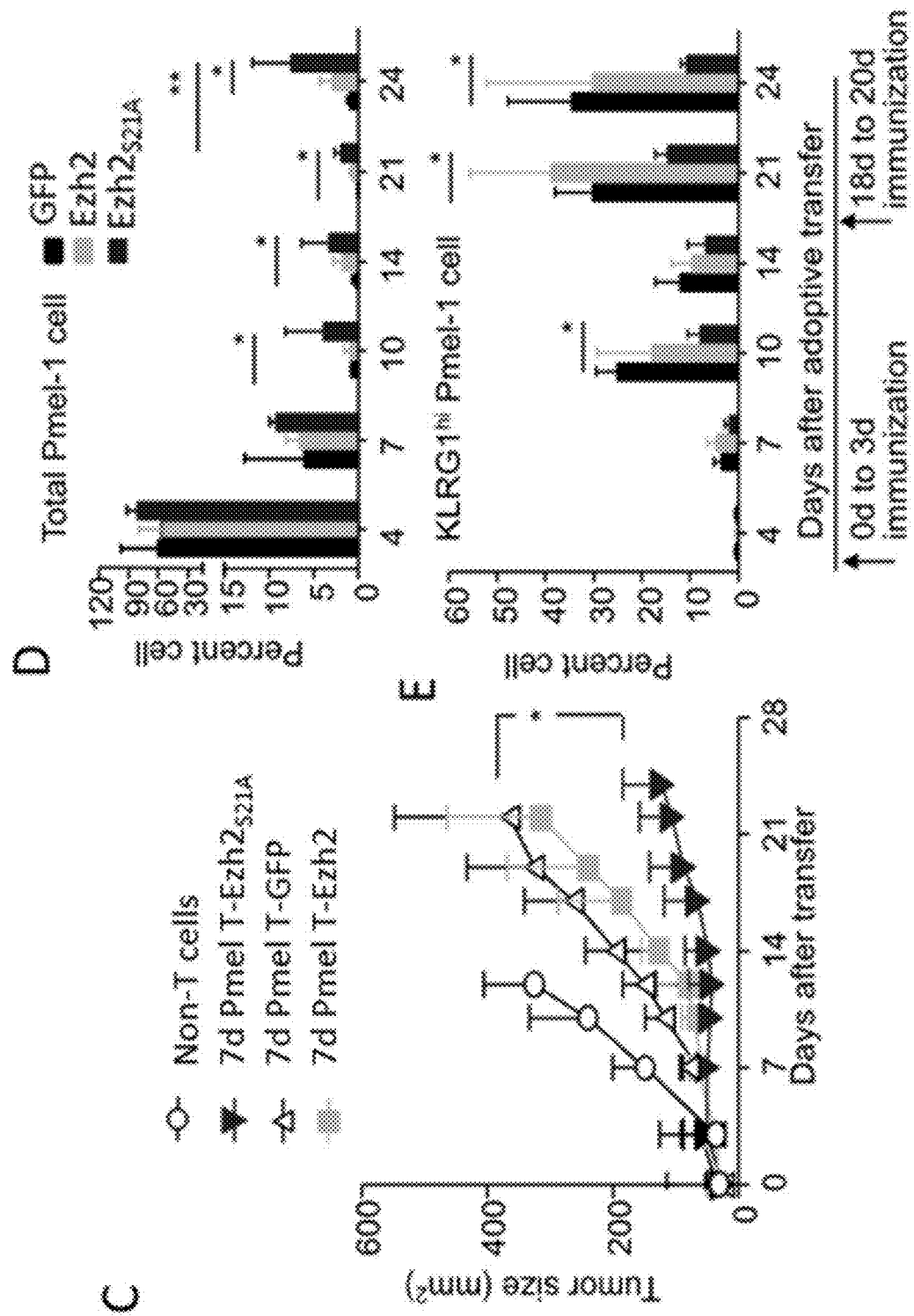
Figures 16F, 16G, 16H:
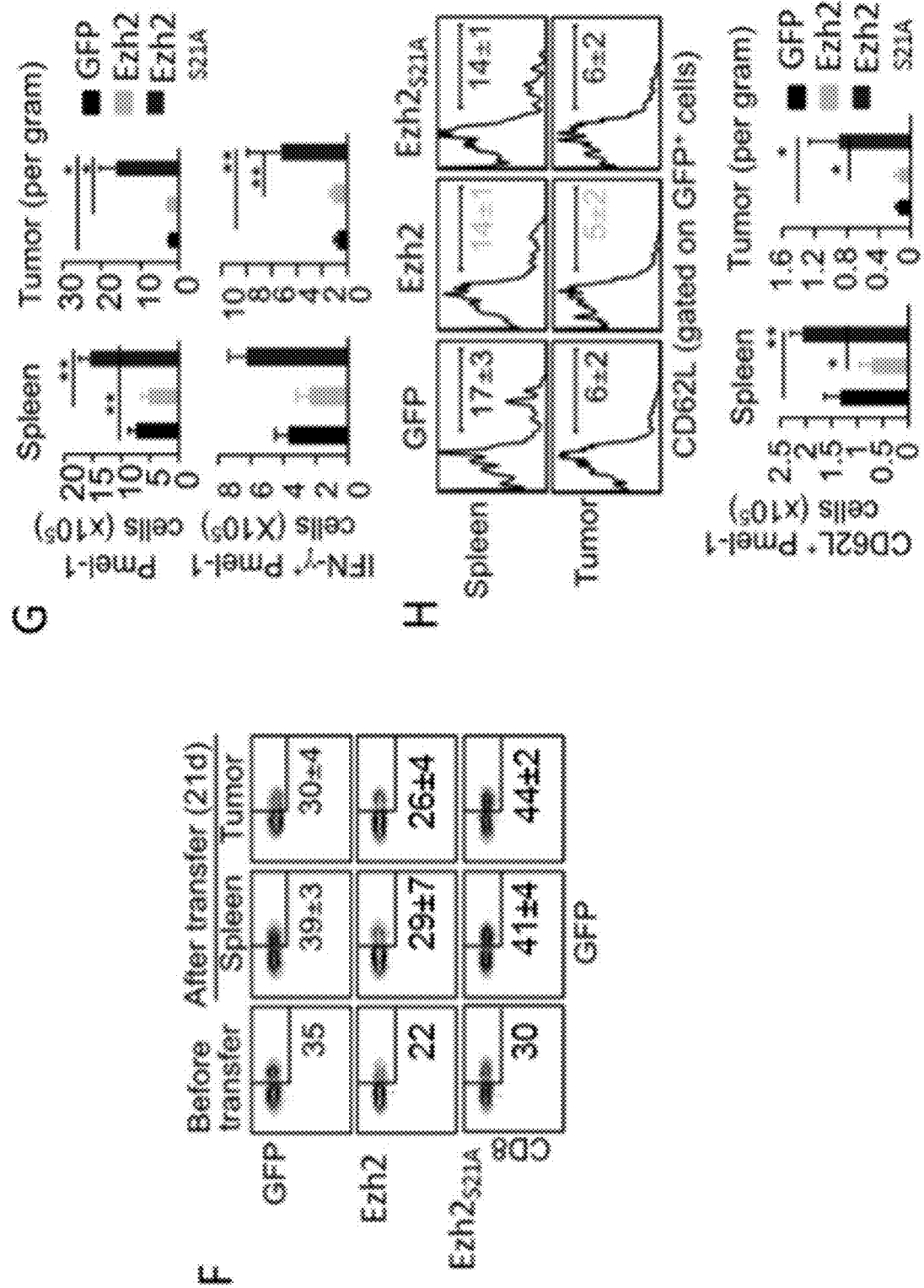

Enhanced tumor immunity by Ezh2S21A-Pmel-1 cells could result from increased expression of overall Ezh2 protein. To test it, it was assessed whether overexpressing normal Ezh2 in Pmel-1 cells, which is susceptible to Akt phosphorylation, may influence their antitumor activity. Transfer of Pmel-1 cells expressing Ezh2S21A had dramatically enhanced capacity to inhibit tumor growth compared to either Ezh2 or GFP control (FIG. 16C). Ezh2S21A-, Ezh2- and GFP-Pmel-1 cell recipients of B16 melanoma had similar amounts of donor T cells in the circulating PB within 7 days after transfer, but surprisingly, over time Ezh2S21A-Pmel-1 cell recipients produced approximately 10-fold more in frequency of donor T cells than either Ezh2- or GFP-Pmel-1 cell recipients between day 10 and day 14 (FIG. 16D). Furthermore, upon rechallenge with gp100/DCs 18 days after transfer, Ezh2S21A-Pmel-1 cell recipients had approximately 4-fold more circulating Pmel-1 cells than Ezh2- and GFP-Pmel-1 cell recipients by 24 days (FIG. 16D), demonstrating an enhanced recall response. It was also found that ectopic expression of Ezh2S21A induced a lower frequency of KLRG1hi cells in vivo 10 days after transfer compared to Ezh2 and GFP controls (FIG. 16E). Further analysis of tumor infiltrating lymphocytes (TILs) showed that as compared to GFP- and Ezh2-Pmel-1 cell recipients, Ezh2S21A-Pmel-1 cell recipients had 1.5-fold higher frequency of TILs (FIG. 16F), 5-fold more total GFP+ TILs and 4-fold more IFN-γ-producing GFP+ TILs (FIG. 16G). Overexpression of Ezh2S21A did not prevent Pmel-1 cells from differentiating into CD62Llo $T_{EFF}$ in vivo (FIG. 16H). However, there were 2-fold and 4-fold more CD62Lhi CD8+ T cells in the spleen and tumor, respectively, from Ezh2S21A Pmel-1 cell recipients than GFP- and Ezh2-Pmel-1 cell recipients (FIG. 16H). Thus, overexpression of Ezh2S21A dramatically improves the persistence of tumor-reactive CD8+ T cells in vivo upon chronic exposure to tumor antigen.

Critical Role of Id3 in Ezh2-Regulated Memory Recall Response

Figures 17A, 17B:
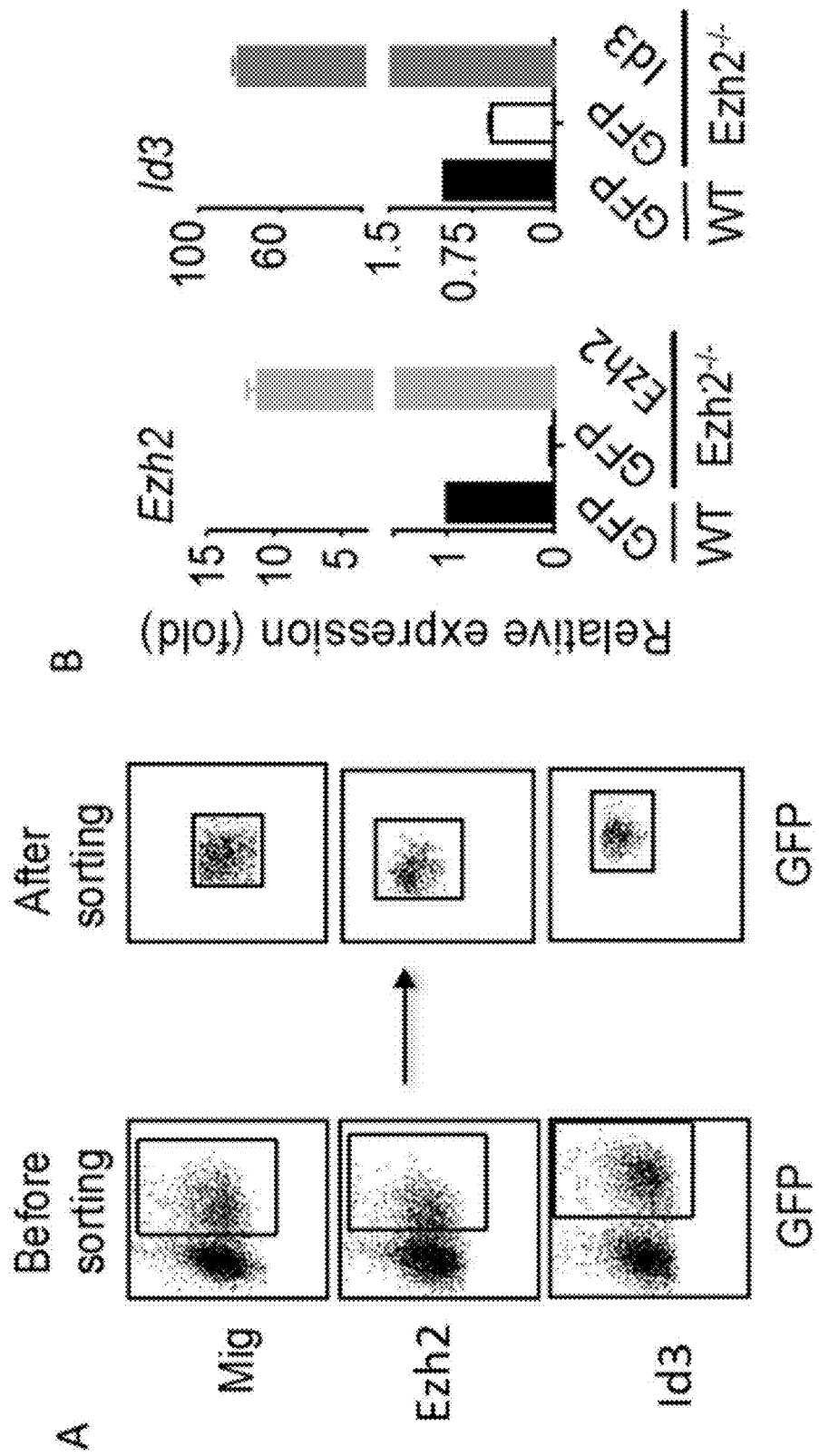
FIG. 17A through FIG. 17B, depicts exemplary experimental results demonstrating retroviral introduction of Id3 into CD8$^+$ T cells. Ezh2$^{-/-}$ Pmel-1 cells (Thy1.1$^+$) were stimulated with anti-CD3/CD28 Ab+IL-2 for 36 hours, infected with MigR1 retrovirus encoding GFP, Ezh2, and Id3, respectively, and FACS sorted at 7 d after culture based on the expression of GFP.
Figures 18A, 18B, 18C:
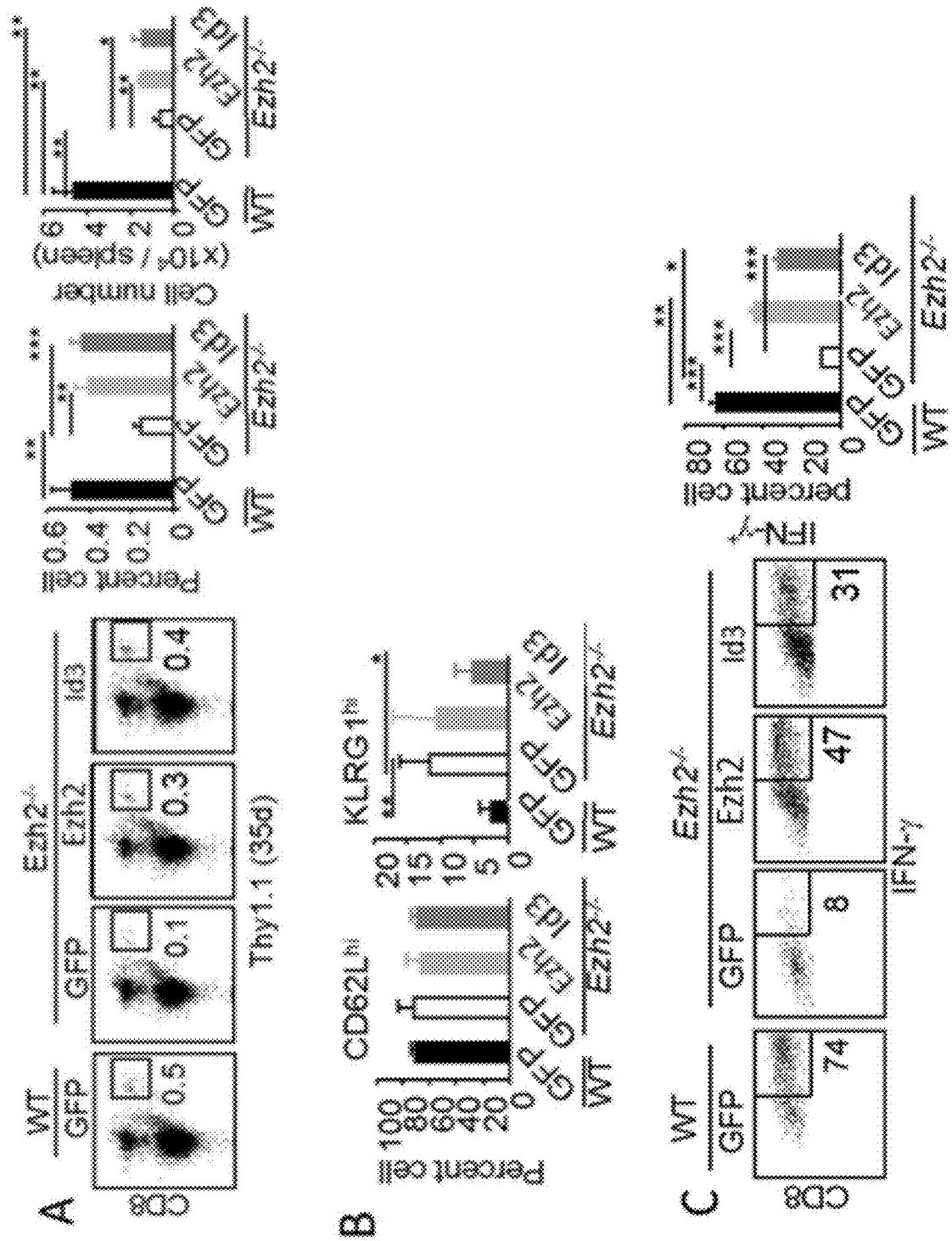
FIG. 18A through FIG. 18I, depicts exemplary experimental results demonstrating that Id3 is a down-stream effector of Akt-unphosphorylated Ezh2 in CD8$^+$ T cells. For FIG. 18A through FIG. 18C, WT and Ezh2$^{-/-}$ T$_N$ Pmel-1 cells (Thy1.1$^+$) were activated and infected with MigR1 encoding GFP, Ezh2, and Id3, respectively. By day 7, GFP$^+$ T cells were sorted and transferred into sublethally irradiated B6 mice (Thy1.2$^+$) (5×10$^5$ cells/mouse). IL-2 and gp100/DCs were administered to these mice for 3 days after the transfer.

Previous studies suggested that the phenotype of Id3-deficient T cells resemble that of Ezh2 inhibition (Tong et al., 2014, J Immunol, 192:5012-5022; He et al., 2013, Blood, 122:4119-4128; He et al., 2012, Blood, 119:1274-1282). Id3 is not required for the initial proliferation of antigen-driven T cells. However, Id3 deficiency leads to the impairment of forming CD8+ memory T cells (Ji et al., 2011, Nat Immunol, 12:1230-1237; Yang et al., 2011, Nat Immunol, 12:1221-1229). To understand whether Id3 mediates regulation of the memory recall response by Ezh2, Id3 was retrovirally introduced into Ezh2−/− Pmel-1 cells (FIG. 17). Adoptive transfer experiments showed that as compared to control GFP-transduction, overexpressing Id3 significantly improved the survival and persistence of Ezh2−/− Pmel-1 cells in vivo 35 days after immunization (FIG. 18A), decreased the fraction of KLRG1hi cells (FIG. 18B) and significantly restored IFN-γ production of these memory Ezh2−/− Pmel-1 cells upon gp100 rechallenging ex vivo (FIG. 18C). Id3-overexpression rescued memory Ezh2−/− Pmel-1 cells to a comparable level of Ezh2-overexpression (FIG. 18A through FIG. 18C). However, neither Id3- nor Ezh2-overexpression completely restored the capability of Ezh2−/− Pmel-1 cells to produce memory cells like GFP-transduced WT Pmel-1 controls (FIG. 18A through FIG. 18C). Since Ezh2 was critical for generating memory precursor cells within 5 d of activation (FIG. 4 and FIG. 5), and since retrovirally introduced genes did not reach peak expression by day 5 after T cell activation, one plausible explanation for the partial rescue effect of Id3 is its delayed expression in Ezh2−/− Pmel-1 cells. This agrees with previous studies showing that overexpression of Id3 in WT Pmel-1 dramatically improved their persistence in vivo (Ji et al., 2011, Nat Immunol, 12:1230-1237).

Figures 18D, 18E, 18F:
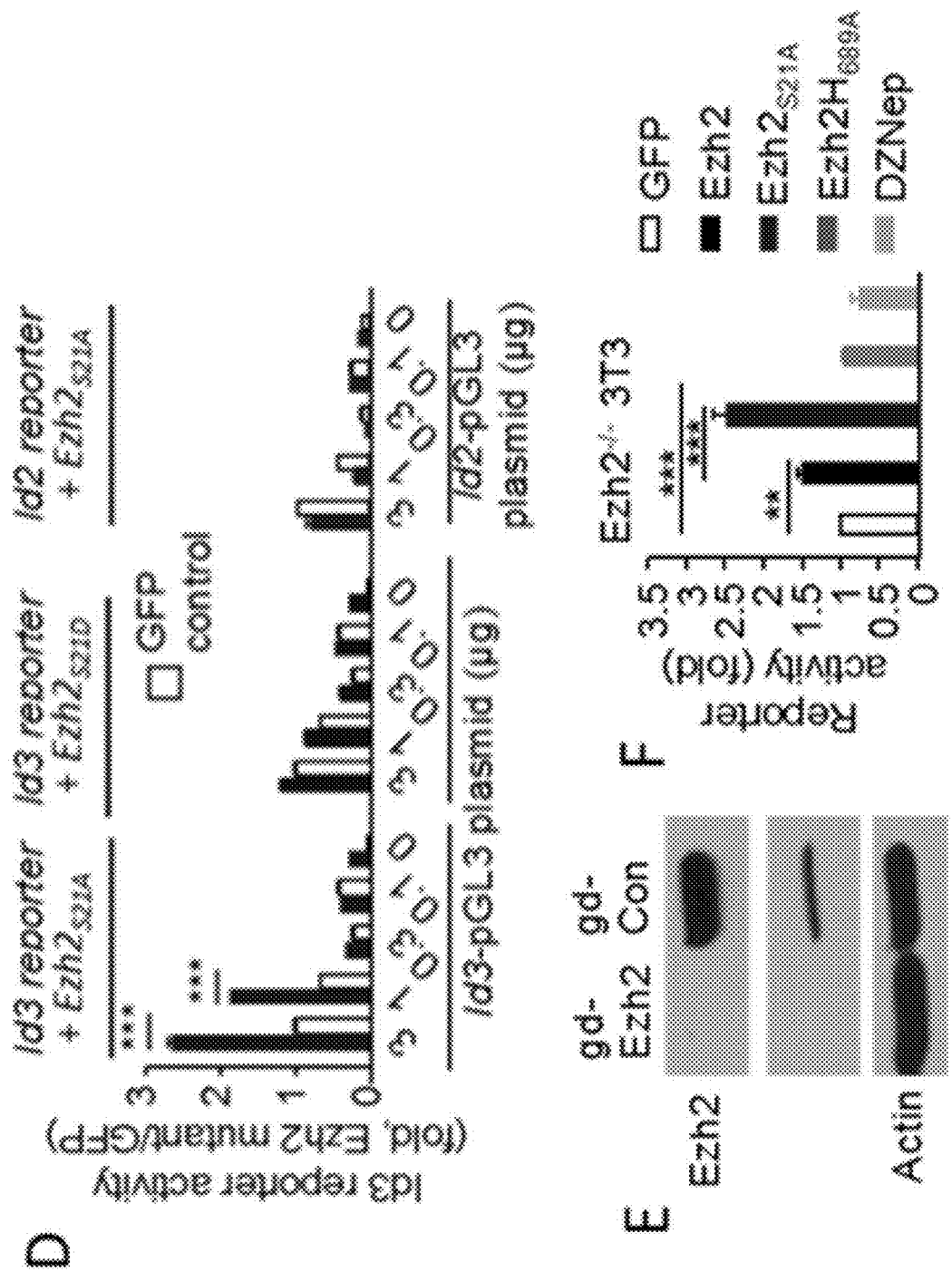

To assess the direct impact of Ezh2 on Id3 activation, the promoter region of the Id3-gene (ranging from −1.5kb upstream of the transcription start site (TSS) to +0.5 Kb down-stream of the TSS) was cloned into the pGL3 luciferase reporter vector and constructed an Id3-specific pGL3 reporter (Id3-pGL). While overexpressing Ezh2S21A activated Id3 rather than Id2 transcription, phosphomimetic Ezh2S21D was unable to activate Id3 (FIG. 18D). To precisely evaluate if Ezh2 enzymatic activity is required to activate Id3 transcription, endogenous Ezh2 was deleted in 3T3 cells using CRISPR (FIG. 18E), followed by viral transduction of various Ezh2 mutants. Mutant Ezh2S21A had a greater capacity than Ezh2 to activate Id3, whereas the loss-of-function mutant Ezh2H689A42 failed to activate Id3 (FIG. 18F). Thus, Ezh2 requires its methyltranferase activity to activate Id3 transcription and loses this activity upon Akt-phosphorylation.

Figures 18G, 18H:
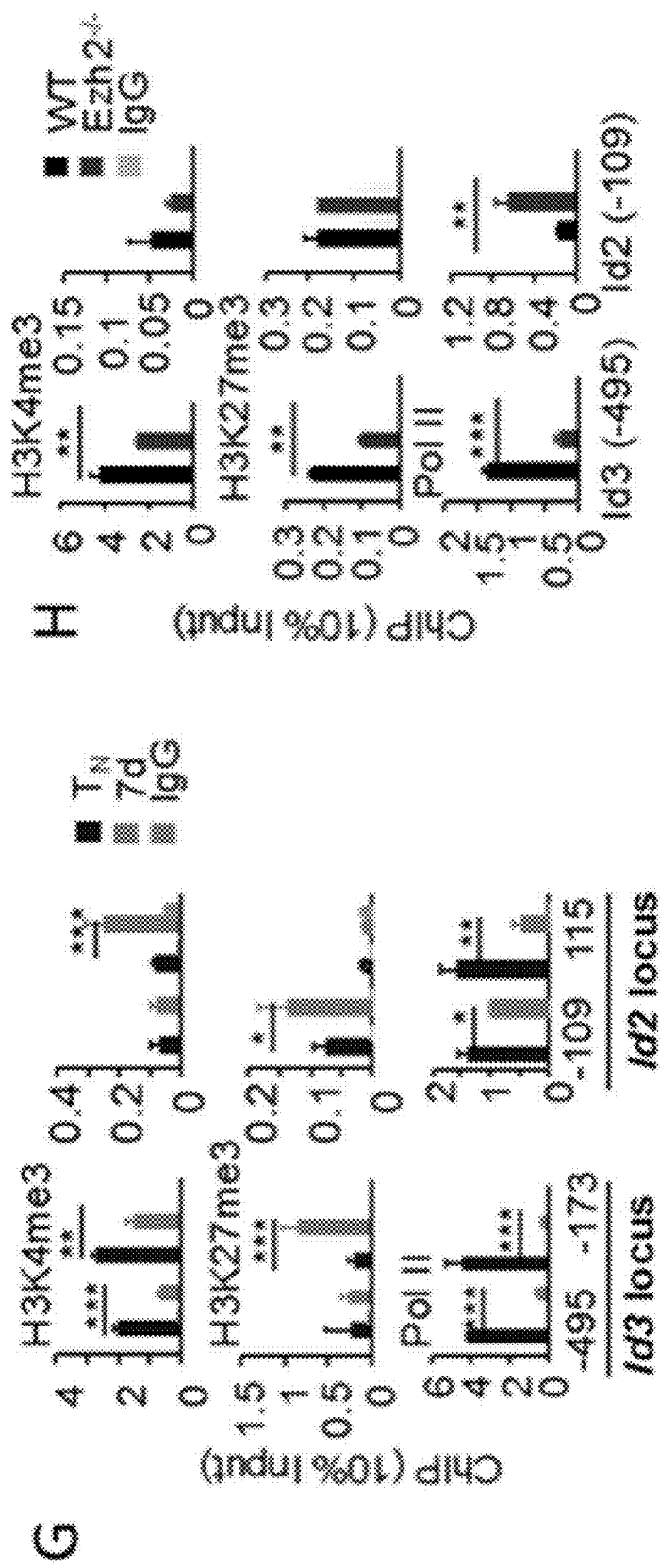

To better understand the mechanism by which Ezh2 stimulated Id3 transcription, the influence of Ezh2 on histone modification states was assessed at the promoter region of Id3. H3K4me3 and RNA polymerase II (Pol II) binding are known to be associated with gene activation. The Id3 locus was marked by both H3K27me3 and H3K4me3 in CD8+ $T_N$. This is agreement with a recent study showing that TFs (e.g., Tbx21, Prdm1, Eomes and Irf4) known to play key roles in effector and memory differentiation are bivalent for both H3K27me3+ and H3K4me3+ histone methylation under naive state (Russ et al., 2014, Immunity, 41:853-865). The amount of Ezh2 at Id3 locus in CD8+ $T_N$ was associated with high levels of H3K4me3 and Pol II (FIG. 18G). TCR-activated CD8+ T cells significantly reduced H3K4me3 and Pol II at Id3 locus upon differentiation (FIG. 18G). Loss of Ezh2 led to decreased deposition of H3K4me3 and PolI II at Id3 locus, but not Id2 locus (FIG. 18H). Thus, Ezh2 activation of Id3 transcription in T cells likely involves the enzyme(s) that catalyzes H3K4me3. Akt phosphorylation of Ezh2 leads to dissociation of pEzh2S21 from the Id3 locus and subsequent resolution into non-permissive state. This is in sharp contrast to the observation by Xu et al. that in prostate cancer cells, Akt-induced pEzh2S21 was recruited by the androgen receptor to gene loci that are marked by H3K4me3 rather than H3K27me3 (Xu et al., 2012, Science, 338:1465-1469). Through binding pEzh2S21, AR activates transcription of these genes lacking H3K27me3 (Xu et al., 2012, Science, 338:1465-1469).

Figure 18I:
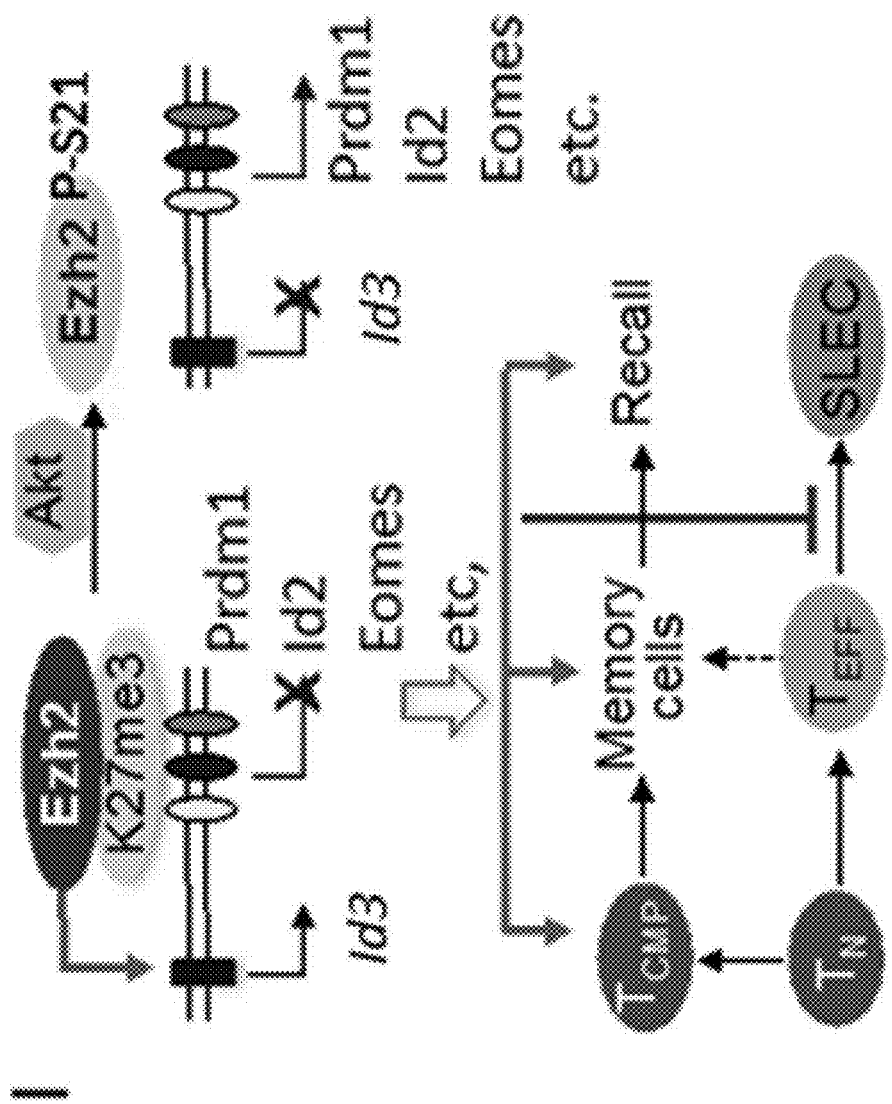

In conclusion, the experimental results presented demonstrate that Ezh2 functions as a key molecular gatekeeper for generating memory CD8 T cells, restraining terminal differentiation and maintaining recall response capability (FIG. 18I). Ezh2 activates Id3 to regulate memory cell formation and the function of CD8+ T cells. Ezh2 also silences Id2, Prdm1 and Eomes in antigen-driven CD8+ T cells to temper effector differentiation. They have further shown that Ezh2 itself is functionally modified by Akt phosphorylation, which diminishes the capacity for Ezh2 to stimulate Id3 and silence Id2, Prdm1 and Eomes, thereby driving effector differentiation and reducing memory potential.

Memory T cells are under active investigation in the context of inhibitory checkpoint blockade therapy and vaccination (Rosenberg and Restifo, 2015, Science, 348:62-68; Jensen and Riddell, 2014, Immunol Rev, 257:127-144; Sadelain, 2009, Cancer J, 15:451-455; Vonderheide and June, 2014, Immunol Rev, 257:7-13; Wherry et al., 2007, Immunity, 27:670-684; Scholler et al., 2012, Sci Transl Med, 4:132ra153; Gattinoni et al., 2011, Nat Med, 17:1290-1297; Hinrichs, 2016, Clin Cancer Res, 22:1559-1564). In ACT it appears that minimally differentiated CD8+ T cells, including naïve and central memory T cells, exhibit superior persistence and enhanced antitumor activity compared with highly differentiated effector T cells (Rosenberg and Restifo, 2015, Science, 348:62-68; Restifo et al., 2012, Nat Rev Immunol, 12:269-281; Crompton et al., 2014, Immunol Rev, 257:264-276; Klebanoff et al., 2016, J Clin Invest, 126:318-334). The goal therefore would be to generate cellular products rich in less-differentiated memory cells, however, the mechanisms that restrain effector differentiation and maintain memory potential of T cells remains poorly understood. Epigenetic alterations appear to play an important role in T cell fate decisions. In addition, T cell signal strength, which determines the quantity and quality of T cell response and includes signals from the TCR, costimulatory molecules and cytokines, is also believed to be epigenetically controlled. However, the epigenetic regulator(s), responsible for the conversion of these signals into the transcriptional programs that generate and maintain memory T cells, has not been fully identified (Fearon, 2007, Adv Immunol, 96:103-139; Gattinoni et al., 2009, Nat Med, 15:808-813; Gerlach et al., 2013, Science, 340:635-639; Buchholz et al., 2013, Science, 340:630-635; Ahmed et al., 2009, Nat Rev Immunol, 9:662-668; Kaech et al., 2002, Nat Rev Immunol, 2:251-262; Zhang et al., 2002, The Journal of clinical investigation, 109:1335-1344). The observation that Ezh2 regulates both precursor and mature memory cells has profound implications towards the development of new strategies to optimize the expansion and quality of therapeutic T cells for ACT. Further, these investigations reveal that Ezh2 activity augments the capacity of transferred T cells to continually produce tumor-destroying $T_{EFF}$ in vivo.

Histone modifications occur in T cells early after antigen priming (Araki et al., 2009, Immunity, 30:912-925; Russ et al., 2014, Immunity, 41:853-865; Wei et al., 2009, Immunity, 30:155-167). Recent studies suggested that CD8$^+$ T cells significantly decreased the amount of H3K27me3 at the promoter regions of genes associated with cell proliferation, differentiation and survival within 24 hours (Russ et al., 2014, Immunity, 41:853-865). It was found that 3 days after TCR engagement Ezh2 was highly induced in CD8$^+$ T cells, however, its function on activating Id3 and repressing Id2, Eomes and Prdm1 was markedly decreased. It has been shown that low expression of Id3 and high levels of Id2, Blimp-1, Eomes and T-bet are associated with enhanced effector differentiation but decreased memory potential (Chang et al., 2014, Nat Immunol, 15:1104-1115; Kaech and Cui, 2012, Nat Rev Immunol, 12:749-761; Paley et al., 2012, Science, 338:1220-1225; Ji et al., 2011, Nat Immunol, 12:1230-1237; Yang et al., 2011, Nat Immunol, 12:1221-1229; Masson et al., 2013, J Immunol 190, 4585-4594; Pearce et al., 2003, Science 302, 1041-1043). In line with these observations, the data suggest that through coordinating the expression of these major TFs in activated CD8$^+$ T cells Ezh2 plays essential roles in preserving $T_{CMP}$ and preventing precocious effector differentiation. To further investigate the mechanism by which unphosphorylated Ezh2 maintained the recall response capacity in memory CD8$^+$ T cells, the data demonstrate that Ezh2 directly bound to the promoter region of Id3 and activated Id3 transcription in a dose-dependent manner. Furthermore, introduction of Id3 into activated CD8$^+$ T cells lacking Ezh2 rescued the generation of memory T cells with improved recall response capacity for producing effector cells upon antigen reencounter. These data agree with other groups' findings that high expression of Id3 preferentially guides the memory development.[33, 34] Thus, Ezh2 targets Id3 to regulate memory formation and function of CD8$^+$ T cells. How the Ezh2-Id3 pathway cooperates with Ezh2 repression of other major TFs to regulate memory cells is a subject of future work.

Given that the phosphorylation state of Ezh2 determines its capacity to maintain CD8$^+$ T cell memory, it is essential to identify when and at which differentiation stage(s) activated CD8$^+$ T cells modify Ezh2 function by Akt-mediated phosphorylation. Antigen-driven CD8$^+$ T cells undergo "progressive" differentiation from $T_N$ to $T_{CMP}$ and $T_{EFF}$ (Rosenberg and Restifo, 2015, Science, 348:62-68; Jensen and Riddell, 2014, Immunol Rev, 257:127-144; Sadelain, 2009, Cancer J, 15:451-455; Vonderheide and June, 2014, Immunol Rev, 257:7-13; Wherry et al., 2007, Immunity, 27:670-684; Scholler et al., 2012, Sci Transl Med, 4:132ra153; Gattinoni et al., 2011, Nat Med, 17:1290-1297; Hinrichs, 2016, Clin Cancer Res, 22:1559-1564). It was observed that Ezh2 was phosphorylated as T cells differentiated and showed decreased function in the context of regulating these major TFs. Notably, $T_{CMP}$ showed intermediate grades in the expression of phosphorylated Ezh2 and Ezh2-targeted TFs between $T_{EFF}$ and $T_N$. This suggests that phosphorylation of Ezh2 initially occurs in the $T_{CMP}$ stage and is further increased upon effector differentiation. Furthermore, the data revealed that similar expression patterns of phosphorylated Ezh2 and its-targeted TFs occurred in ex vivo expanding CD8$^+$ T cells 3 days after activation and peaked by 7 days when full-fledged $T_{EFF}$ developed. Consequently, T cells expressing high levels of phosphorylated Ezh2 displayed significantly impaired capacity to produce $T_{CMP}$ in vivo after transfer and to inhibit tumor growth. These changes were consistent with Akt activity in $T_N$, $T_{CMP}$ and $T_{EFF}$. The data provide molecular insights into the mechanism how the quantity and quality of T cell memory is epigenetically programmed during initial expansion phase (Gattinoni et al., 2009, Nat Med, 15:808-813; Gerlach et al., 2013, Science, 340:635-639; Buchholz et al., 2013, Science, 340:630-635).

This study has significant implications in optimizing the expansion and quality of therapeutic T cells used for treating cancer and chronic infections. The capability of tumor-reactive T cells to replicate and persist in vivo is crucial for effectively controlling tumor growth and eliminating virus-infected cells (Rosenberg and Restifo, 2015, Science, 348: 62-68; Jensen and Riddell, 2014, Immunol Rev, 257:127-144; Sadelain, 2009, Cancer J, 15:451-455; Vonderheide and June, 2014, Immunol Rev, 257:7-13; Wherry et al., 2007, Immunity, 27:670-684; Scholler et al., 2012, Sci Transl Med, 4:132ra153; Gattinoni et al., 2011, Nat Med, 17:1290-1297; Hinrichs, 2016, Clin Cancer Res, 22:1559-1564). In support of this, the data demonstrate that Akt-unphosphorylated Ezh2 mediated epigenetic effects are critically involved in regulating both the quantity and quality of memory precursor cells and their differentiation into mature memory cells. These data support the observation that ex vivo treatment of expanding CD8$^+$ T cells with certain Akt inhibitors led to increased frequency of memory precursor cells and improved antitumor immunity in vivo after infusion (Crompton et al., 2015, Cancer Res, 75, 296-305; van der Waart et al., 2014, Blood, 124:3490-3500). However, ex vivo Akt inhibitor treatment resulted in a transient effect and did not prevent reactivation of Akt in CD8$^+$ T cells in vivo upon antigen rechallenge. These findings suggest that the prolonged presence of Akt-insensitive Ezh2 in tumor-reactive CD8$^+$ T cells is required for them to preserve their memory properties in vivo when signals activating Akt persist. It is reasonable to assume that continual treatment with Akt inhibitors might extend its effect on promoting memory T cells in vivo. However, effective cancer immunotherapy requires collective efforts of both effector and memory T cells (Rosenberg and Restifo, 2015, Science, 348:62-68; Restifo et al., 2012, Nat Rev Immunol, 12:269-281; Vonderheide and June, 2014, Immunol Rev, 257:7-13). Systemic administration of Akt inhibitors may reduce the production of effector T cells and cause adverse effects. T cell-specific expression of Akt-insensitive EZH2 or a molecule specifically blocking the Ezh2 and Akt interaction could be a wise option to improve the antitumor efficacy of tumor-reactive T cells. It will be interesting to investigate whether an inducible system able to conditionally express functional Ezh2 in T cells would selectively prolong and enhance the Ezh2 effect in tumor-reactive T cells in vivo.

These findings together with Kakaradov's studies (Kakaradov et al., 2017, Nature immunology 18, 422-432) indicate that the impact of Ezh2 on antigen-driven CD8$^+$ T cells may vary at different activation state and differentiation stage. Ezh2 was crucial for the survival and expansion of activated CD8+ T cells later after antigen priming. By day 5 after activation, Ezh2 deficiency selectively increased apoptosis in effector T cells rather than $T_{CM}$-like cells (Kakaradov et al., 2017, Nature immunology 18, 422-432). However, early after antigen priming (e.g., by day 3) Ezh2 was dispensable for survival of antigen-primed CD8+ T cells (Kakaradov et al., 2017, Nature immunology 18, 422-432). Importantly, it was also identified that loss of Ezh2 caused preferential decrease of $T_{CMP}$ pool independent of cell apoptosis early during expansion, while markedly increasing the fraction of terminal $T_{EFF}$. Since both the first division of activated CD8+ T cells and their subsequent differentiation early after antigen priming may influence the ratio of $T_{CMP}$ and $T_{EFF}$ (Gerlach et al., 2013, Science, 340:635-639; Buchholz et al., 2013, Science, 340:630-635; Kakaradov et al., 2017, Nature immunology, 18:422-432; Chang et al., 2007, Science, 315:1687-1691), without being bound by a particular theory, it is proposed that Ezh2 is important for preserving the $T_{CMP}$ pool and restraining precocious terminal differentiation. Interestingly, Kakaradov's studies showed that Ezh2 deficiency caused no difference in the production of terminal KLRG1$^{hi}$ cells. They observed that despite the presence of Ezh2, as many as 75% of P14 CD8+ T cells had undergone terminal differentiation (e.g. expression of KLRG1$^{hi}$) at day 4 after LCMV infection and only 1% of activated P14 CD8+ T cells were $T_{CMP}$-like phenotype 7 days after infection (Kakaradov et al., 2017, Nature immunology, 18:422-432). In contrast, the data herein dempnstrate that WT Pmel-1 cells consisted of less than 10% KLRG1$^{hi}$ cells and approximately 50% $T_{CMP}$ at the peak of effector response. Loss of Ezh2 led to production of 4-fold more terminal KLRG1$^{hi}$ cells, accompanied with increased expression of 370-fold more p19$^{Arf}$ transcript.

In conclusion, Ezh2 is the epigenetic regulator essential for the development and maintenance of memory T cells and associated antitumor immunity. Ezh2 targets Id3 to regulate memory cell formation and function of CD8+ T cells. Ezh2 also silences Id2, Prdm1 and Eomes in antigen-driven CD8+ T cells to temper effector differentiation. Akt mediates phosphorylation of Ezh2, which in turn eases Ezh2 transcriptional control, causing enhanced effector differentiation at the expense of memory T cells. In a preclinical mouse model, T cell-specific expression of an Akt-insensitive Ezh2 mutant markedly prolonged the in vivo persistence of T cells with memory potential, augmenting their ability to inhibit tumor growth. As such, Akt-mediated Ezh2 phosphorylation serves as a critical target to potentiate anti-tumor immunotherapeutic strategies, and, more broadly, an enhanced understanding of biology of T cell responses.

Example 2: A Method to Produce Multipotent CAR Cells

EZH2, which catalyzes trimethylation of histone H3 at lysine 27 (H3K27me3) and acts primarily as a gene silencer, is essential for the development and maintenance of memory T cells and their-mediated antitumor immunity. EZH2 silences transcription factors (TFs) ID2, PRDM1, TBX21 and EOMES while activating ID3, guiding the population expansion and differentiation of naïve T cells into memory cells, including $T_{SCM}$ and TCM. Ezh2 also controls the recall response capability of memory T cells upon antigen encounter. Unexpectedly, despite highly expressing EZH2, activated T cells decrease these EZH2 functions along a progressive differentiation path through a mechanism of phosphorylating EZH2 by active AKT. Engineering of T cells with AKT-insensitive EZH2 dramatically improves the generation of functional memory T cells and their antitumor effects. Thus, EZH2 controls memory T cell development and maintenance, whereas signals mediating T cell expansion taper EZH2 function to drive effector differentiation.

Figures 19A, 19B, 19C:
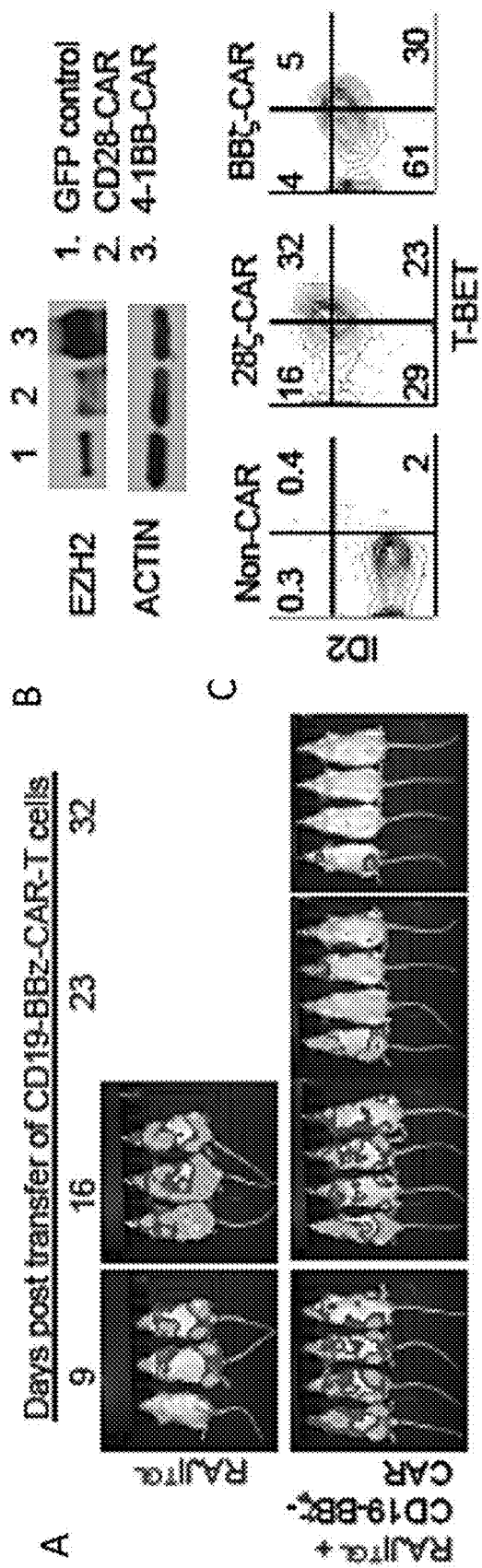
FIG. 19A through FIG. 19C, depicts exemplary experimental results demonstrating engineered human T cells with lentivrial vector encoding CD19-specific chimeric antigen receptor (CAR).

To translate these findings into adoptive cell immunotherapy, human T cells were engineered with lentivrial vector encoding CD19-specific chimeric antigen receptor (CAR) with 4-1BB and CD3ζ (named BBζ) signals (FIG. 19).

Further, the effect of combined pharmacologic compounds on producing tumor-resistant CAR $T_{SCM}$ cells is examined based on modifying EZH2 function in preclinical models of human lymphoma xenografts. Results from these experiments establish a novel culture system for production of long-lasting and cost-effective memory CAR T cells that may be translated into patients with solid tumors in a broad context.

Figure 20:
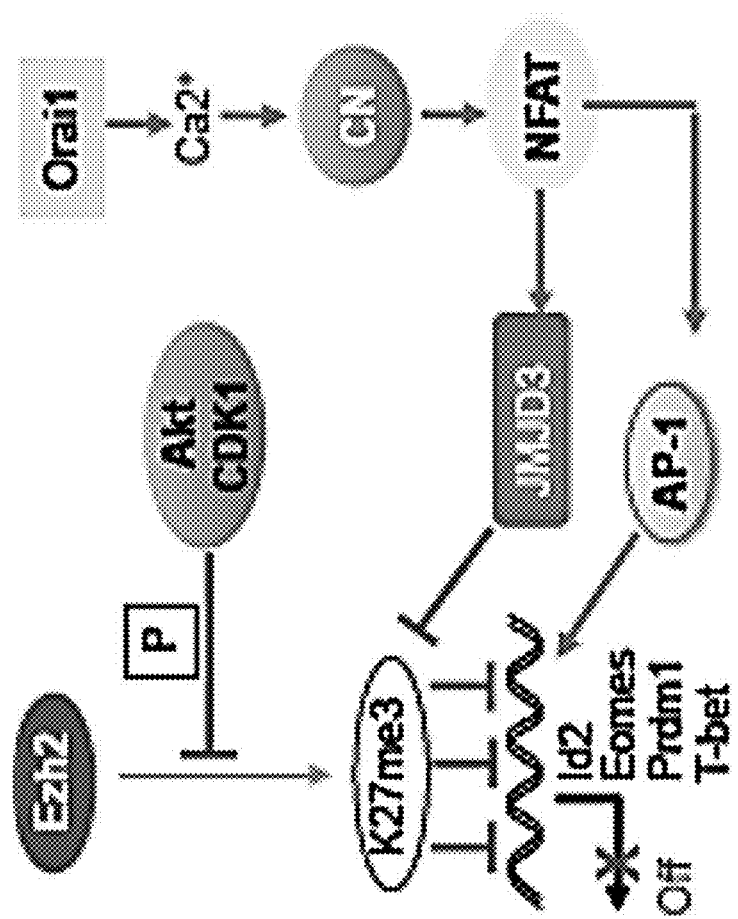
FIG. 20 depicts a schematic diagram of pathways regulating the transcriptional plasticity and stability of human memory CAR T cells.

To establish a novel and clinically relevant pharmacological approach to induce CAR i$T_{SCM}$, it was evaluated whether a combined inhibition, including blocking calcinurin regulated Ca2+ signaling, inhibiting demethylation by JMJD3, reducing EZH2 phosphorylation by AKT and inhibiting AP-1-driven differentiation, may facilitate the preservation of i$T_{SCM}$ upon exposure to persistent and high-dose antigen. To test this possibility, chemical probes are used that selectively inhibit calcinurin (CsA), JMJD3 (GSK-J4), AKT (MEK2206) and AP-1 (TanIIA) to see if each may lead to down-regulation of pro-differentiation TFs and upregulation of pro-memory TFs (FIG. 20). The combination of these probes may have superior capacity of inducing and sustaining CAR i$T_{SCM}$. The combined probes are referred to herein as ACJA, which refers to the combination of inhibitors for AKT, Calcinurin, JMJD3 and AP-1.

To assess if ACJA augments the production of less-differentiated CD19-CAR T cells and further facilitates the expansion and enrichment of CD19-CAR i$T_{SCM}$, pro-memory cytokines (e.g., IL-21, IL-15 and IL-7, etc.) are added to the culture to determine: A) whether ACJA may improve the capacity of CD19-CAR i$T_{SCM}$ to acquire the ability to resist high tumor burden; B) the optimal time of adding ACJA to cultures for inducing maximal production and preservation of CD19-CAR i$T_{SCM}$ in reaction to high-dose antigen (i.e., the optimal dose of each probe and time and duration of ACJA treatment for expanding and sustaining CAR i$T_{SCM}$); and C) characterize the biological properties of ACJA-induced CD19-CAR i$T_{SCM}$, in particularly their metabolic profiles. Emerging evidence indicate that BBζ-CAR signaling is able to promote metabolic features associated with T cell proliferation, differentiation and memory development. This is critical for the generation of long-lived memory T cells efficient for eliminating tumor cells or chronic infection in vivo.

Wishing not to be bound by theory, it is believed that results from these experiments: 1) identify how EZH2 orchestrates the development and maintenance of weakly-differentiated memory CAR T cells in concert with co-signals and Ca2+ signals; 2) establish a novel culture system able to produce long-lasting and cost-effective memory CAR T cells for clinical application; and 3) illuminate a novel epigenetic mechanism by which EZH2 regulates the transcriptional plasticity and stability of human memory CAR T cells. Molecular insights into the fundamentals of human T cells may lead to new strategies to improve adoptive cell immunotherapy for chronic infections and advanced tumors in a broad context. Successful outcome of developing a clinical relevant pharmacological approach and cellular product enriched with CAR iT$_{SCM}$ will enable the translation of the basic science of into patients, leading to new strategies to improve therapeutic efficacy for lymphoma and other type of solid tumor in a broad context.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising an improved T-cell, wherein the T cell has increased EZH2 activity;
   wherein the improved T cell has at least about a 5-fold decrease in phosphorylated EZH2 and about a 4-fold increase in H3K27me3;
   wherein the T cell has been contacted with an inhibitor of a regulator of at least one of the level and activity of EZH2; and
   wherein the regulator of EZH2 is selected from the group consisting of phosphatidylinositol 3-kinase (PI3K), calcineurin, JMJD3, AKT, AP-1, CDK1, CDK4/6, DNA-PK, and a combination thereof;
   wherein the inhibitor is selected from the group consisting of CsA, Tacrolimus, GSK-J4, 5-Carboxy-8-hydroxyquinoline, MEK2206, SB203580, MK2206, SC79, AZD5363, LM22B-10, GDC-0068, GSK-690693, Afuersertib, AKT inhibitor VIII, A-443654, TIC10, Honokiol, Triciribine, A-674563, Prifosine, Miltefosine, SR11302, SP100030, c-JUN peptide, TanIIA, E3330, NNGH, Sulfaphenoazole, U0126 monoethanolate, IQ-1S, SM-7368, NIN-43, MEK inhibitor VII, TNAP inhibitor, FR180204, APE1 inhibitor III, (S)-AR-TURMERONE, 4-O-METHYLHONOKIOL, 5-(9-ISOPROPYL-2-MORPHOLINO-9H-PURIN-6-YL)PYRMIDIN-2-AMINE, A66, Arenobufagin, Bay80-6946, Benidipine Hydrochloride, BEX235, BKM120, BYL719, CAL-101, CH5132799, CUDC-907, GDC-0980, GSK-2126458, GSK-2334470, GSK-2636771, IPI-145, Ly-294002, PF-04691502 Dihydrate, Piceatanol, PKI-402, PP-121, PX-866, R547, Dinaciclib, BMS-265246, JNJ-7706621, AZD5438, Alvociclib, SU9516, PHA-793887, P276-00, AT7519, PHA-7677491, Milciclib (PHA-848125), SNS-032, NU6027, LDC000067, Palbociclib, Everolimus, Ly3023414, KU-57788, NU 7026, PIK-75, LTURM34, CC-115, Compound 401 and a combination thereof.

2. A composition comprising an improved T cell, wherein the T cell has increased EZH2 activity;
   wherein the improved T cell has at least about a 5-fold decrease in phosphorylated EZH2 and about a 4-fold increase in H3K27me3; and,
   wherein the T cell expresses an EZH2S21A protein.

3. The composition of claim 1, wherein the inhibitor is an inhibitory RNA molecule targeting PI3K.

4. The composition of claim 1, wherein the T cell is an anti-tumor T cell selected from the group consisting of a CART cell, a TCR-transgenic T cell, a Tumor infiltrating T cell (TIL), an autologous T cell, and an allogeneic T cell.

5. The composition of claim 1, wherein the T cell is an anti-tumor CART cell comprising a chimeric antigen receptor (CAR) comprising at least one sequence selected from the group consisting of a binding domain, a co-stimulatory signaling domain, a cytoplasmic signaling sequence and a combination thereof.

6. The composition of claim 5, wherein the CAR comprises at least one selected from the group consisting of a CD19 binding domain, a 4-1BB co-stimulatory signaling domain, and a CD3ζ cytoplasmic signaling sequence.

7. A composition comprising an improved T cell, wherein the T cell has increased EZH2 activity;
   wherein the improved T cell has at least about a 5-fold decrease in phosphorylated EZH2 and about a 4-fold increase in H3K27me3; and
   wherein the cell comprises an mRNA molecule encoding a variant of EZH2 or a mimetic of EZH2 that does not get phosphorylated by AKT.

8. The composition of claim 7, wherein the cell is an anti-tumor T cell selected from the group consisting of a CART cell, a TCR-transgenic T cell, a TIL, an autologous T cell, and an allogeneic T cell.

9. The composition of claim 2, wherein the T cell further expresses a modulator of at least one of the level and activity of Ezh2, wherein the modulator increases the amount of polypeptide of EZH2, increases the amount of mRNA of EZH2, increases the activity of EZH2, modulates the phosphorylation state of EZH2, decreases the level or activity of a negative regulator of EZH2, or any combination thereof.

* * * * *